US011608518B2

(12) United States Patent
Balasubramanian et al.

(10) Patent No.: US 11,608,518 B2
(45) Date of Patent: Mar. 21, 2023

(54) METHODS FOR ANALYZING NUCLEIC ACIDS

(71) Applicant: Cambridge Epigenetix Limited, Saffron Walden (GB)

(72) Inventors: Shankar Balasubramanian, Cambridge (GB); Jens Fullgrabe, Great Chesterford (GB); Walraj Singh Gosal, Cambridge (GB); Joanna Dawn Holbrook, London (GB); Sidong Liu, Saffron Walden (GB); David Morley, St. Albans (GB); Oliver Nentwich, Cambridge (GB); Tobias Ost, Ely (GB); Michael Steward, Royston (GB); Albert Vilella, Cambridge (GB); Nicolas James Walker, Cambridge (GB); Shirong Yu, Cambridge (GB); Helen Rachel Bignell, Cambridge (GB); Rita Santo San-Bento, Lyons (FR)

(73) Assignee: Cambridge Epigenetix Limited, Saffron Walden (GB)

( * ) Notice: Subject to any disclaimer, the term of this patent is extended or adjusted under 35 U.S.C. 154(b) by 0 days.

(21) Appl. No.: 17/700,257

(22) Filed: Mar. 21, 2022

(65) Prior Publication Data

US 2022/0290215 A1 Sep. 15, 2022

Related U.S. Application Data

(63) Continuation of application No. PCT/GB2021/051957, filed on Jul. 29, 2021.

(60) Provisional application No. 63/215,752, filed on Jun. 28, 2021, provisional application No. 63/213,626, filed on Jun. 22, 2021, provisional application No. 63/212,500, filed on Jun. 18, 2021, provisional application No. 63/210,927, filed on Jun. 15, 2021, provisional application No. 63/178,386, filed on Apr. 22, 2021, provisional application No. 63/152,976, filed on Feb. 24, 2021, provisional application No. 63/106,566, filed on Oct. 28, 2020, provisional application No. 63/105,860, filed on Oct. 26, 2020, provisional application No. 63/061,093, filed on Aug. 4, 2020, provisional application No. 63/058,712, filed on Jul. 30, 2020.

(51) Int. Cl.
| | | |
|---|---|---|
| *C12Q 1/6827* | (2018.01) | |
| *C12Q 1/6806* | (2018.01) | |
| *C12Q 1/6869* | (2018.01) | |
| *C12N 15/10* | (2006.01) | |
| *C12N 15/52* | (2006.01) | |
| *C12Q 1/6811* | (2018.01) | |
| *C12Q 1/686* | (2018.01) | |

(52) U.S. Cl.
CPC ....... *C12Q 1/6827* (2013.01); *C12N 15/1058* (2013.01); *C12N 15/52* (2013.01); *C12Q 1/686* (2013.01); *C12Q 1/6806* (2013.01); *C12Q 1/6811* (2013.01); *C12Q 1/6869* (2013.01)

(58) Field of Classification Search
CPC ............... C12Q 1/6827; C12Q 1/6806; C12Q 1/6869
See application file for complete search history.

(56) References Cited

U.S. PATENT DOCUMENTS

| | | |
|---|---|---|
| 8,653,007 B2 | 2/2014 | Zheng et al. |
| 8,679,745 B2 | 3/2014 | Ballhause et al. |
| 8,741,567 B2 | 6/2014 | He et al. |
| 8,771,939 B2 | 7/2014 | Tetzner et al. |
| 8,822,146 B2 | 9/2014 | Klimasauskas et al. |
| 8,889,352 B2 | 11/2014 | Klimasauskas et al. |
| 8,895,268 B2 | 11/2014 | Kester |
| 8,951,736 B2 | 2/2015 | Schmidt |
| 8,962,246 B2 | 2/2015 | Ballhause et al. |
| 8,969,061 B2 | 3/2015 | Zhu et al. |
| 9,029,087 B2 | 5/2015 | Zheng et al. |
| 9,034,597 B2 | 5/2015 | Bitinaite et al. |
| 9,040,239 B1 | 5/2015 | Zheng et al. |
| 9,115,386 B2 | 8/2015 | Rao et al. |
| 9,121,061 B2 | 9/2015 | Vaisvila et al. |
| 9,145,580 B2 | 9/2015 | Feehery et al. |
| 9,150,918 B2 | 10/2015 | Turner et al. |
| 9,175,338 B2 | 11/2015 | Flusberg et al. |
| 9,175,341 B2 | 11/2015 | Flusberg et al. |

(Continued)

FOREIGN PATENT DOCUMENTS

| | | |
|---|---|---|
| EP | 1568786 A2 | 8/2005 |
| EP | 2376632 A1 | 10/2011 |

(Continued)

OTHER PUBLICATIONS

Berney, et al. Methods for detection of cytosine and thymine modifications in DNA. Nature Reviews Chemistry. Oct. 12, 2018. (2):332-348 https://doi.org/10.1038/s41570-018-0044-4.
Chen, et al. "Single-cell whole-genome analyses by Linear Amplification via Transposon Insertion (LIANTI)." Science 356.6334 (2017): 189-194.
Co-pending U.S. Appl. No. 17/675,502, filed Feb. 18, 2022.
Co-pending U.S. Appl. No. 17/863,689, filed Jul. 13, 2022.

(Continued)

*Primary Examiner* — Cynthia B Wilder
(74) *Attorney, Agent, or Firm* — Wilson Sonsini Goodrich & Rosati

(57) ABSTRACT

Provided herein are methods, systems, and compositions for determining a base in a polynucleotide. In various aspects, the methods, systems, and compositions presented herein are useful for performing 4-base, 5-base, or 6-base sequencing of polynucleotide molecules, for example, from liquid biopsy samples or wherein the base is a low frequency mutation.

27 Claims, 67 Drawing Sheets

(56) References Cited

U.S. PATENT DOCUMENTS

| | | | |
|---|---|---|---|
| 9,175,348 B2 | 11/2015 | Korlach et al. | |
| 9,200,260 B2 | 12/2015 | Correa, Jr. et al. | |
| 9,200,316 B2 | 12/2015 | Zheng et al. | |
| 9,238,836 B2 | 1/2016 | Korlach et al. | |
| 9,243,233 B2 | 1/2016 | Rim et al. | |
| 9,267,117 B2 | 2/2016 | Guan et al. | |
| 9,347,093 B2 | 5/2016 | Klimasauskas et al. | |
| 9,447,452 B2 | 9/2016 | Rao et al. | |
| 9,464,277 B2 | 10/2016 | Zheng et al. | |
| 9,505,797 B2 | 11/2016 | Klimasauskas et al. | |
| 9,546,400 B2 | 1/2017 | Turner et al. | |
| 9,567,633 B2 | 2/2017 | Gao et al. | |
| 9,611,510 B2 | 4/2017 | He et al. | |
| 9,650,675 B2 | 5/2017 | Rimseliene et al. | |
| 9,677,128 B2 | 6/2017 | Robertson et al. | |
| 9,816,986 B2 | 11/2017 | Rao et al. | |
| 9,879,315 B2 | 1/2018 | Summerer et al. | |
| 9,896,726 B2 | 2/2018 | Vaisvila et al. | |
| 9,915,655 B2 | 3/2018 | Bensimon et al. | |
| 9,988,673 B2 | 6/2018 | Klimasauskas et al. | |
| 10,023,909 B2 | 7/2018 | Dahl et al. | |
| 10,031,131 B2 | 7/2018 | Rao et al. | |
| 10,041,938 B2 | 8/2018 | Rao et al. | |
| 10,081,827 B2 | 9/2018 | Guan et al. | |
| 10,155,939 B1 | 12/2018 | Vaisvila et al. | |
| 10,227,646 B2 | 3/2019 | Vaisvila et al. | |
| 10,260,087 B2 | 4/2019 | Coll et al. | |
| 10,260,088 B2 | 4/2019 | Vaisvila et al. | |
| 10,323,269 B2 | 6/2019 | Rao et al. | |
| 10,337,053 B2 | 7/2019 | Rao et al. | |
| 10,443,091 B2 | 10/2019 | Rao et al. | |
| 10,465,234 B2 | 11/2019 | Rao et al. | |
| 10,508,301 B2 | 12/2019 | Rao et al. | |
| 10,533,213 B2 | 1/2020 | Rao et al. | |
| 10,612,076 B2 | 4/2020 | Rao et al. | |
| 10,619,200 B2 | 4/2020 | Vaisvila et al. | |
| 10,640,811 B2 | 5/2020 | Edelman | |
| 10,706,957 B2 | 7/2020 | Lo et al. | |
| 10,731,204 B2 | 8/2020 | Rao et al. | |
| 10,767,216 B2 | 9/2020 | Rao et al. | |
| 10,774,373 B2 | 9/2020 | Rao et al. | |
| 10,793,899 B2 | 10/2020 | Rao et al. | |
| 11,001,976 B2 | 5/2021 | Baratta et al. | |
| 11,072,818 B2 | 7/2021 | Rao et al. | |
| 11,078,529 B2 | 8/2021 | Dahl et al. | |
| 11,124,825 B2 | 9/2021 | Vaisvila et al. | |
| 11,168,363 B2 | 11/2021 | Brown et al. | |
| 11,208,683 B2 | 12/2021 | Rao et al. | |
| 11,274,335 B2 | 3/2022 | Arensdorf et al. | |
| 11,306,355 B2 | 4/2022 | Song et al. | |
| 2004/0048279 A1 | 3/2004 | Olek et al. | |
| 2004/0054162 A1 | 3/2004 | Hanna | |
| 2005/0153296 A1 | 7/2005 | Berlin et al. | |
| 2006/0257905 A1 | 11/2006 | Freije et al. | |
| 2007/0026393 A1 | 2/2007 | Berlin et al. | |
| 2007/0238117 A1 | 10/2007 | Rajeevan et al. | |
| 2007/0269824 A1 | 11/2007 | Albrecht et al. | |
| 2008/0096206 A1 | 4/2008 | Densham | |
| 2008/0206772 A1* | 8/2008 | Kajita | C12Q 1/6827 435/6.12 |
| 2010/0167942 A1 | 7/2010 | Zheng et al. | |
| 2010/0197510 A1 | 8/2010 | Spain et al. | |
| 2011/0059432 A1 | 3/2011 | Ballhause et al. | |
| 2011/0301045 A1 | 12/2011 | He et al. | |
| 2012/0064521 A1 | 3/2012 | Yen et al. | |
| 2013/0230856 A1 | 9/2013 | Schneider et al. | |
| 2013/0244237 A1* | 9/2013 | Vaisvila | C12Q 1/6827 435/227 |
| 2013/0323728 A1 | 12/2013 | Robertson et al. | |
| 2014/0004511 A1 | 1/2014 | Korlach et al. | |
| 2014/0178873 A1 | 6/2014 | Brachmann et al. | |
| 2014/0179564 A1 | 6/2014 | Korlach et al. | |
| 2014/0272970 A1 | 9/2014 | Zegzouti et al. | |
| 2014/0322707 A1 | 10/2014 | He et al. | |
| 2015/0004596 A1 | 1/2015 | Zhu et al. | |
| 2015/0011403 A1 | 1/2015 | Lo et al. | |
| 2015/0056616 A1 | 2/2015 | He et al. | |
| 2015/0240310 A1 | 8/2015 | Bitinaite et al. | |
| 2015/0285807 A1 | 10/2015 | Shi et al. | |
| 2015/0307542 A1 | 10/2015 | Roy et al. | |
| 2016/0046981 A1 | 2/2016 | Correa, Jr. et al. | |
| 2016/0115525 A1 | 4/2016 | Ebenstein et al. | |
| 2016/0194696 A1 | 7/2016 | Guan et al. | |
| 2016/0258014 A1 | 9/2016 | Booth et al. | |
| 2016/0304552 A1 | 10/2016 | Roy et al. | |
| 2017/0051354 A1 | 2/2017 | Davis et al. | |
| 2017/0067093 A1 | 3/2017 | Klimasauskas et al. | |
| 2017/0175085 A1 | 6/2017 | Rao et al. | |
| 2017/0175129 A1 | 6/2017 | Roy et al. | |
| 2017/0176420 A1 | 6/2017 | Rao et al. | |
| 2017/0198344 A1 | 7/2017 | Vaisvila et al. | |
| 2017/0219589 A1 | 8/2017 | Rao et al. | |
| 2017/0253924 A1 | 9/2017 | Lu et al. | |
| 2017/0283863 A1 | 10/2017 | Robertson et al. | |
| 2017/0298422 A1 | 10/2017 | Song et al. | |
| 2017/0335297 A1* | 11/2017 | Ha | C12N 9/14 |
| 2018/0044632 A1 | 2/2018 | Rao et al. | |
| 2018/0044633 A1 | 2/2018 | Rao et al. | |
| 2018/0044731 A1 | 2/2018 | Valouev et al. | |
| 2018/0105884 A1 | 4/2018 | Lo et al. | |
| 2018/0112206 A1 | 4/2018 | Forsyth | |
| 2018/0119225 A1 | 5/2018 | Rao et al. | |
| 2018/0170984 A1 | 6/2018 | Harris et al. | |
| 2018/0171397 A1 | 6/2018 | Vaisvila et al. | |
| 2018/0179587 A1 | 6/2018 | Rao et al. | |
| 2018/0201993 A1 | 7/2018 | Turner et al. | |
| 2018/0237839 A1 | 8/2018 | Rao et al. | |
| 2018/0245128 A1 | 8/2018 | He et al. | |
| 2018/0251815 A1 | 9/2018 | Okamoto et al. | |
| 2018/0258149 A1 | 9/2018 | Motz et al. | |
| 2018/0258474 A1 | 9/2018 | Jain et al. | |
| 2018/0312914 A1 | 11/2018 | Vaisvila et al. | |
| 2018/0327855 A1 | 11/2018 | Ebenstein et al. | |
| 2019/0017109 A1 | 1/2019 | Song et al. | |
| 2019/0048407 A1 | 2/2019 | Rao et al. | |
| 2019/0055593 A1 | 2/2019 | Rao et al. | |
| 2020/0002760 A1 | 1/2020 | Rand | |
| 2020/0040381 A1 | 2/2020 | Rao et al. | |
| 2020/0063194 A1 | 2/2020 | Ju et al. | |
| 2020/0063213 A1 | 2/2020 | Cao et al. | |
| 2020/0087715 A1 | 3/2020 | Rao et al. | |
| 2020/0087716 A1 | 3/2020 | Rao et al. | |
| 2020/0102616 A1 | 4/2020 | He et al. | |
| 2020/0224190 A1 | 7/2020 | Song et al. | |
| 2020/0283826 A1* | 9/2020 | Wu | C12Y 201/01037 |
| 2020/0388349 A1 | 12/2020 | Lo et al. | |
| 2021/0095351 A1 | 4/2021 | Das et al. | |
| 2021/0207200 A1 | 7/2021 | Vaisvila et al. | |
| 2021/0214780 A1 | 7/2021 | Jiang et al. | |
| 2021/0214781 A1 | 7/2021 | Patel | |
| 2021/0230679 A1 | 7/2021 | Rao et al. | |
| 2021/0388433 A1 | 12/2021 | Vaisvila et al. | |
| 2022/0090176 A1 | 3/2022 | Rao et al. | |
| 2022/0145386 A1 | 5/2022 | Dahl et al. | |
| 2022/0162675 A1 | 5/2022 | Delatte et al. | |
| 2022/0298551 A1 | 9/2022 | Balasubramanian et al. | |

FOREIGN PATENT DOCUMENTS

| | | |
|---|---|---|
| EP | 2414527 A1 | 2/2012 |
| EP | 2414528 A1 | 2/2012 |
| EP | 2470675 A1 | 7/2012 |
| EP | 2630257 A1 | 8/2013 |
| EP | 2694686 A2 | 2/2014 |
| EP | 2776575 A1 | 9/2014 |
| EP | 2825645 A2 | 1/2015 |
| EP | 2948774 A1 | 12/2015 |
| EP | 3013979 A1 | 5/2016 |
| EP | 3053585 A1 | 8/2016 |
| EP | 3124605 A1 | 2/2017 |
| EP | 3214183 A1 | 9/2017 |
| EP | 3368688 A1 | 9/2018 |
| WO | WO-2009092035 A2 | 7/2009 |
| WO | WO-2009150229 A1 | 12/2009 |

(56) References Cited

FOREIGN PATENT DOCUMENTS

| WO | WO-2010037001 A2 | 4/2010 |
| --- | --- | --- |
| WO | WO-2010048337 A2 | 4/2010 |
| WO | WO-2012138973 A2 | 10/2012 |
| WO | WO-2013017853 A2 | 2/2013 |
| WO | WO-2013090588 A1 | 6/2013 |
| WO | WO-2013138644 A2 | 9/2013 |
| WO | WO-2013163207 A1 | 10/2013 |
| WO | WO-2014165549 A1 | 10/2014 |
| WO | WO-2016183289 A1 | 11/2016 |
| WO | WO-2017081689 A1 | 5/2017 |
| WO | WO-2018129120 A1 | 7/2018 |
| WO | WO-2018165459 A1 | 9/2018 |
| WO | WO-2019013613 A2 | 1/2019 |
| WO | WO-2019099081 A1 | 5/2019 |
| WO | WO-2020223250 A1 | 11/2020 |
| WO | WO-2021028682 A1 | 2/2021 |
| WO | WO-2021178893 A2 | 9/2021 |
| WO | WO-2022023753 A1 | 2/2022 |

OTHER PUBLICATIONS

European search report and opinion dated Oct. 10, 2018 for EP Application No. 18174572.0.

Field, et al. Accurate measurement of 5-methylcytosine and 5-hydroxymethylcytosine in human cerebellum DNA by oxidative bisulfite on an array (OxBS-array). PLoS One. Feb. 2, 20153;10(2):e0118202. doi: 10.1371/journal.pone.0118202. eCollection 2015.

Flusberg, et al. Direct Detection of DNA Methylation During Single-molecule, Real-time Sequencing. Nature Methods 7 (2010): 461-465.

GenBank Accession No. AAI44094 Version No. AAI44094.1 DNA (cytosine-5-)-methyltransferase 1 [*Homo sapiens*]. Record created Jan. 8, 2009. 3 pages. Retrieved online at URL: https://www.ncbi.nlm.nih.gov/protein/AAI44094.1.

GenBank Accession No. P15840 Version No. P15840.3 RecName: Full=Orphan methyltransferase M.SssI; Short=M.SssI; AltName: Full=CpG DNA methylase; AltName: Full=Cytosine-specific methyltransferase SssI. Record created Apr. 24, 1993. 2 pages. Retrieved online at URL: https://www.ncbi.nlm.nih.gov/protein/417325?sat=5&satkey=815549479.

Georgopoulos, et al. Studies with glucosyl transferase mutants of the T-even bacteriophages. Virology. May 1971;44(2):271-285. doi: 10.1016/0042-6822(71)90259-5.

Holmes, et al. Performance Evaluation of Kits for Bisulfite-Conversion of DNA from Tissues, Cell Lines, FFPE Tissues, Aspirates, Lavages, Effusions, Plasma, Serum, and Urine. PLoS One. 2014; 9(4): e93933. Published online Apr. 3, 2014. doi: 10.1371/journal.pone.0093933.

Huang, et al. The behaviour of 5-hydroxymethylcytosine in bisulfite sequencing. PLoS One. Jan. 26, 2010;5(1):e8888. doi: 10.1371/journal.pone.0008888.

International search report with written opinion dated Jan. 14, 2022 for PCT/GB2021/051957.

International search report with written opinion dated Feb. 28, 2013 for PCT/US2012/069525.

Ivanov, et al. Single base resolution analysis of 5-hydroxymethylcytosine in 188 human genes: implications for hepatic gene expression. Nucleic Acids Res.Aug. 19, 2016;44(14):6756-6769. doi: 10.1093/nar/gkw316. Epub Apr. 29, 2016.

Liu, et al. Bisulfite-free direct detection of 5-methylcytosine and 5-hydroxymethylcytosine at base resolution. Nat Biotechnol. Apr. 2019;37(4):424-429. doi: 10.1038/s41587-019-0041-2. Epub Feb. 25, 2019. (with Supplementary information).

McInroy, et al. Enhanced Methylation Analysis by Recovery of Unsequenceable Fragments. PLoS One. Mar. 31, 2016;11(3):e0152322. doi: 10.1371/journal.pone.0152322. eCollection 2016.

Münzel, et al. 5-Hydroxymethylcytosine, the sixth base of the genome. Angew Chem Int Ed Engl. Jul. 11, 2011;50(29):6460-6468. doi: 10.1002/anie.201101547. Epub Jun. 17, 2011.

Mok, et al. A bacterial cytidine deaminase toxin enables CRISPR-free mitochondrial base editing. Nature. Jul. 2020;583(7817):631-637. doi: 10.1038/s41586-020-2477-4. Epub Jul. 8, 2020.

Nestor, et al. Enzymatic Approaches and Bisulfite Sequencing Cannot Distinguish Between 5-Methylcytosine and 5-Hydroxymethylcytosine in DNA. Biotechniques 48 (2010): 317-319.

Office action dated Jun. 24, 2022 for U.S. Appl. No. 17/700,226.

Raine, et al. SPlinted Ligation Adapter Tagging (SPLAT), a novel library preparation method for whole genome bisulphite sequencing. Nucleic Acids Research, vol. 45, No. 6 e36 (2017). Published online Nov. 29, 2016. 15 pages.

Regier, et al. Functional equivalence of genome sequencing analysis pipelines enables harmonized variant calling across human genetics projects. Nat Commun. Oct. 2, 2018;9(1):4038. doi: 10.1038/S41467-018-06159-4.

Robertson, et al. A novel method for the efficient and selective identification of 5-hydroxymethylcytosine in genomic DNA. Nucleic Acids Res. Apr. 2011;39(8):e55. doi: 10.1093/nar/gkr051. Epub Feb. 7, 2011.

Runnberg, et al. Either Rap1 or Cdc13 can protect telomeric single-stranded 3' overhangs from degradation in vitro. Sci Rep. 2019; 9: 19181. Published online Dec. 16, 2019. doi: 10.1038/S41598-019-55482-3.

Sabatini, et al. Recognition of base J in duplex DNA by J-binding protein. J Biol Chem. Jan. 11, 2002;277(2):958-966. doi: 10.1074/jbc.M109000200. Epub Nov. 7, 2001.

Schüler, et al. Sequencing the sixth base (5-hydroxymethylcytosine): selective DNA oxidation enables base-pair resolution. Angew Chem Int Ed Engl. Oct. 22, 2012;51(43):10704-10707. doi: 10.1002/anie.201204768. Epub Sep. 26, 2012.

Schutsky et al. Nondestructive, Base-Resolution Sequencing of 5-Hydroxymethylcytosine Using a DNA Deaminase. Nature Biotechnology 36(11):1083-1090 (2018).

Shen, et al. Mechanism and function of oxidative reversal of DNA and RNA methylation. Annu Rev Biochem. 2014;83:585-614. doi: 10.1146/annurev-biochem-060713-035513.

Song, et al. Detection of 5-hydroxymethylcytosine in a combined glycosylation restriction analysis (CGRA) using restriction enzyme Taq($\alpha$)I. Bioorg Med Chem Lett. Sep. 1, 2011;21(17):5075-5077. doi: 10.1016/j.bmcl.2011.03.118. Epub Apr. 9, 2011.

Song, et al. Detection of 5-hydroxymethylcytosine in DNA by transferring a keto-glucose by using T4 phage Plucosyltransferase, Chembiochem 12.11 (2011): 1682-1685.

Song, et al. Selective chemical labeling reveals the genome-wide distribution of 5-hydroxymethylcytosine. Nature Biotechnology 29 (2011): 68-72.

Song, et al. The hunt for 5-hydroxymethylcytosine: the sixth base. Epigenomics. Oct. 2011;3(5):521-523. doi: 10.2217/epi.11.74.

Sun, et al. Nondestructive enzymatic deamination enables single-molecule long-read amplicon sequencing for the determination of 5-methylcytosine and 5-hydroxymethylcytosine at singlebase resolution. Genome Res. Jan. 19, 2021;31(2):291-300. doi: 10.1101/gr.265306.120. Online ahead of print.

Takahashi, et al. A novel method to analyze 5-hydroxymethylcytosine in CpG sequences using maintenance DNA methyltransferase, DNMT1. FEBS Open Bio. Sep. 8, 2015;5:741-747. doi: 10.1016/j.fob.2015.09.003. eCollection 2015.

Tan, et al. Mirror Bisulfite Sequencing: A Method for Single-Base Resolution of Hydroxymethylcytosine. Anal Chem. Nov. 20, 2018;90(22):13200-13206. doi: 10.1021/acs.analchem.8b02832. Epub Nov. 2, 2018.

Valinluck, et al. Endogenous cytosine damage products alter the site selectivity of human DNA maintenance methyltransferase DNMT1. Cancer Research 67.3 (2007): 946-950.

Wang et al. Variant association tools for Quality control and analysis of large-scale sequence and genotyping array data. The American Journal of Human Genetics 9:770-783 (2014).

Wilson, et al. High-Fidelity Nanopore Sequencing of Ultra-Short DNA Targets. Anal Chem. May 21, 2019; 91(10): 6783-6789. Published online Apr. 30, 2019. doi: 10.1021/acs.analchem.9b00856.

(56) References Cited

OTHER PUBLICATIONS

Yu, et al. Base-resolution analysis of 5-hydroxymethylcytosine in the mammalian genome. Cell. Jun. 8, 2012;149(6):1368-80. doi: 10.1016/j.cell.2012.04.027. Epub May 17, 2012.

Yu, et al. Tet-assisted bisulfite sequencing of 5-hydroxymethylcytosine. Nat Protoc. Dec. 2012;7(12):2159-70. doi: 10.1038/nprot.2012.137. Epub Nov. 29, 2012.

European search report and opinion dated Sep. 27, 2022 for EP Application No. 22170290.5.

Boreal Genomics. Pro-Seq: A high fidelity and cost-effective duplex sequencing method for ctDNA detection. AGBT Conference, Boreal Genomics. Published Feb. 2018, see https://borealgenomics.com/about-boreal/newspress/.

Buermans et al.: Next Generation sequencing technology: Advances and applications, Biochimica et Biophysica Acta (BBA)—Molecular Basis of Disease, 1842:1931-1941 (2014).

Giehr, et al. Two are better than one: HPoxBS—hairpin oxidative bisulfite sequencing. Nucleic Acids Res. Sep. 6, 2018;46(15):e88. doi: 10.1093/nar/gky422.

Karamitros, et al. A novel method for the multiplexed target enrichment of MinION next generation sequencing libraries using PCR-generated baits. Nucleic Acids Res. Dec. 15, 2015;43(22):e152. doi: 10.1093/nar/gkv773. Epub Aug. 3, 2015.

Office action dated Jan. 17, 2023 for U.S. Appl. No. 17/700,226.

Pel, et al. Duplex Proximity Sequencing (Pro-Seq): A method to improve DNA sequencing accuracy without the cost of molecular barcoding redundancy. PLoS One. Oct. 2, 2018;13(10):e0204265. doi: 10.1371/journal.pone.0204265. eCollection 2018.

Salk, Jesse J. et al. Enhancing the accuracy of next-generation sequencing for detecting rare and subclonal mutations. Nature Reviews Genetics 19 (2018): 269-285.

Ståhlberg, et al. Simple, multiplexed, PCR-based barcoding of DNA enables sensitive mutation detection in liquid biopsies using sequencing. Nucleic Acids Res. Jun. 20, 2016;44(11):e105. doi: 10.1093/nar/gkw224. Epub Apr 7, 2016.

Sun, et al. HBS-Tools for Hairpin Bisulfite Sequencing Data Processing and Analysis. Adv Bioinformatics. 2015;2015:760423. doi: 10.1155/2015/760423. Epub Dec. 20, 2015.

Third party observation dated Feb. 3, 2023 for EP Application No. 21755018.5.

\* cited by examiner

FIG. 13

| True base | F strand | F' strand |
|---|---|---|
| A | A | T |
| C | C | G |
| G | G | C |
| T | T | A |
| Error (F/F') | A/A, A/C, A/G, C/A, C/C, C/T, G/A, G/G, G/T, T/C, T/G, T/T | |

*FIG. 20A*

| True base | F strand | F' strand |
|---|---|---|
| A | A | T |
| C | T | G |
| G | G | T |
| T | T | A |
| Methylated C | C | G |
| Error (F/F') | A/A, A/C, A/G, C/A, C/C, C/T, G/A, G/C, G/G, T/C, T/T | |

FIG. 20B

| True base | F strand | F' strand |
|---|---|---|
| A | A | T |
| C or 5hmC | T | G |
| G | G | T |
| T | T | A |
| 5mC | C | G |
| Error (F/F') | A/A, A/C, A/G, C/A, C/C, C/T, G/A, G/C, G/G, T/C, T/T | |

*FIG. 20C*

| True base | F strand | F strand |
|---|---|---|
| A | A | T |
| C | C | G |
| G | G | C |
| T | T | A |
| 5mCpG | T | G |
| 5hmCpG | G | T |
| 5hmCpG | T | G |
| | G | C |
| Error (F/F) | A/A, A/C, A/G, C/A, C/C, C/T, G/A, G/G, T/C, T/T + G/T or T/G in non-CpG context | |

*FIG. 20D*

| True base | F strand | F' strand |
|---|---|---|
| A | A | T |
| C | T | G |
| G | G | T |
| T | T | A |
| 5mCpG | C | G |
| 5hmCpG | G | C |
| 5hmCpG | C | G |
| | G | T |
| Error (F/F') | A/A, A/C, A/G, C/A, C/C, C/T, G/A, G/G, T/C, T/T + C/G or G/C in non-CpG context | |

| True base | F strand | F' strand |
|---|---|---|
| A | A | T |
| C | T | G |
| G | G | T |
| T | T | A |
| 5mCpG / 5hmCpG | C | G |
| Error (F/F') | A/A, A/C, A/G, C/A, C/C, C/T, G/A, G/G, T/C, T/T, G/C, C/G in non-CpG context | |

*FIG. 25*

| True base | F strand | F' strand |
|---|---|---|
| A | A | T |
| C | U | G |
| G | G | T |
| T | T | A |
| Error (F/F') | A/A, A/C, A/G, C/A, C/C, C/T, C/G, G/A, G/G, G/C, T/C T/T, T/G | |

*FIG. 26*

|  | NA24385 | NA24631 |
|---|---|---|
| # Reads Aligned | 2.19 billion | 2.42 billion |
| # Bases Aligned | 241 billion | 266 billion |
| Strand Balance | 0.50 | 0.50 |
| Unfiltered Coverage | 82.5x | 91.2x |
| Duplication Rate | 63.5% | 67.6% |
| De-duplicated Coverage | 30.1x | 29.6x |

*FIG. 28*

|  | NA24385 | NA24631 |
|---|---|---|
| Total SNPs | 3.35 million | 3.32 million |
| % in dbSNP (SNPs) | 97.1% | 97.2% |
| dbSNP Ti/Tv | 2.074 | 2.069 |
| Novel Ti/Tv | 1.98 | 2.01 |
| Total Indels | 642K | 639K |
| % in dbSNP (Indels) | 93.9% | 94.2% |
| Ins/Del (known, novel) | 0.90, 0.93 | 0.90, 0.96 |

*FIG. 29*

|  | NA24385 | NA24631 |
|---|---|---|
| SNP het/hom sensitivity | 91.9%, 92.0% | 94.2%, 94.7% |
| SNP het/hom PPV | 99.0%, 99.9% | 98.9%, 99.9% |
| SNP genotype concordance | 99.9% | 99.9% |
| SNP non-ref GC | 91.4% | 93.8% |
| Indel het/hom sensitivity | 84.9%, 84.3% | 88.6%, 90.2% |
| Indel het/hom PPV | 96.7%, 99.4% | 97.4%, 99.3% |
| Indel genotype concordance | 99.9% | 99.9% |
| Indel non-ref GC | 82.5% | 87.5% |

*FIG. 30*

|  | SS NA24385 | NIST NA24385 | SS NA24631 | NIST NA24631 |
|---|---|---|---|---|
| Total SNPs | 3.35 million | 3.5 million | 3.32 million | 3.57 million |
| % in dbSNP (SNPs) | 97.1% | 90.3% | 97.2% | 91.6% |
| dbSNP Ti/Tv | 2.074 | 2.066 | 2.069 | 2.06 |
| Novel Ti/Tv | 1.93 | 0.709 | 2.01 | 0.76 |
| Total Indels | 642K | 1.25 million | 639K | 1.12 million |
| % in dbSNP (indels) | 93.9% | 47.5% | 94.2% | 51.6% |
| Ins/Del (known, novel) | 0.90, 0.93 | 0.91, 2.63 | 0.90, 0.96 | 0.91, 3.36 |

*FIG. 31*

|  | NA24385 | NIST NA24385 | NA24631 | NIST NA24631 |
|---|---|---|---|---|
| SNP het/hom sensitivity | 91.9%, 92.0% | 87.6%, 90.9% | 94.2%, 94.7% | 93.1%, 95.7% |
| SNP het/hom PPV | 99.0%, 99.9% | 87.5%, 98.7% | 98.9%, 99.9% | 89.6%, 99.1% |
| SNP genotype concordance | 99.9% | 99.9% | 99.9% | 99.9% |
| SNP non-ref GC | 91.4% | 82.2% | 93.8% | 88.5% |
| Indel het/hom sensitivity | 84.9%, 84.3% | 81.2%, 89.4% | 88.6%, 90.2% | 86.1%, 93.2% |
| Indel het/hom PPV | 96.7%, 99.4% | 30.7%, 97.5% | 97.4%, 99.3% | 32.1%, 97.3% |
| Indel genotype concordance | 99.9% | 99.9% | 99.9% | 99.9% |
| Indel non-ref GC | 82.5% | 38.3% | 87.5% | 41.1% |

*FIG. 32*

|  | Sample | Chunks |
|---|---|---|
| Lane 01 | NA24385 | 119 |
| Lane 02 | NA24385 | 121 |
| Lane 03 | NA24631 | 131 |
| Lane 04 | NA24631 | 134 |

*FIG. 33A*

|  | NA24385 | NA24631 | 1% Mixin |
|---|---|---|---|
| # Reads Aligned | 2.19 billion | 2.43 billion | 2.45 billion |
| # Bases Aligned | 241 billion | 266 billion | 270 billion |
| Strand Balance | 0.50 | 0.50 | 0.50 |
| Unfiltered Coverage | 82.5x | 91.2x | 92.3x |
| Duplication Rate | 63.5% | 67.6% | N/A |
| De-duplicated Coverage | 30.1x | 29.6x | N/A |

*FIG. 33B*

|  | 6x dups removed | 6x no dup marking |
|---|---|---|
| # Reads Aligned | 156 million | 156 million |
| # Bases Aligned | 17.3 billion | 17.3 billion |
| Strand Balance | 0.5005 | 0.5005 |
| Unfiltered Coverage | 5.9x | 5.9x |
| Duplication Rate | 14.5% | 0% |
| De-duplicated Coverage | 5.0x | 5.9x |

*FIG. 34*

|  | NA24385 original | NA24385 5x | NA24385 6x |
|---|---|---|---|
| Total SNPs | 3.35 million | 2.43 million | 3.29 million |
| % in dbSNP (SNPs) | 97.1% | 96.3% | 72.1% |
| dbSNP Ti/Tv | 2.074 | 2.056 | 2.070 |
| Novel Ti/Tv | 1.93 | 3.06 | 26.6 |
| Total Indels | 642K | 328K | 340K |
| % in dbSNP (Indels) | 93.9% | 95.7% | 95.1% |
| Ins/Del (known, novel) | 0.90, 0.93 | 0.90, 0.86 | 0.89, 0.85 |

14/18 possible single nucleotide variants require 2 changes in the SingleShot code, precluding false positive mutation calls caused by ILMN seq errors Of 18 possible single nucleotide variants(including mutation from m/hmC and G in a CpG context)

Extremely low risk of false positives due to substitution error with Single Shot 14 would require 2 substitution errors on the hairpin to be false positives caused by substitution errors. This is vanishingly unlikely.

4 would require one substitution, either A->G or G->A.

REFERENCE
GENOME:  C-G-T-A-A-C-C-G-T-A-C-C-G-G

HAIRPIN FOR GENOMIC:
F 5'  T-G-T-A-A-T-G-T-T-A-C-C-G-G
F 3'  G-T-A-T-G-G-T-A-A-T-G-G-C-C

MUTATION
5'  T-A-C-G-T-A-G-C-T-A-G-T

HAIRPIN FOR MUTATION:
F 5'  T-A-T-G-A-G-U-T-A-G-U-T-G-A-T
F 3'  G-A-T-A-T-U-G-A-U-T-G-A-T

◌ = mismatch between reference genome and sample (due to mutation, polymorphism or error)
⊘ = error that would have to occur in SingleShot hairpin base to cause a false positive for that mutation

FIG. 37

Standard pre-deamination workflow involving the use of enzyme digestion to generate a nick on hairpin adapter (that contains uridines)

Pre-deamination workflow involving no enzyme digestion and a new hairpin lacking uridines (with 3' phosphate) and the use of template DNA lacking 5' phosphate

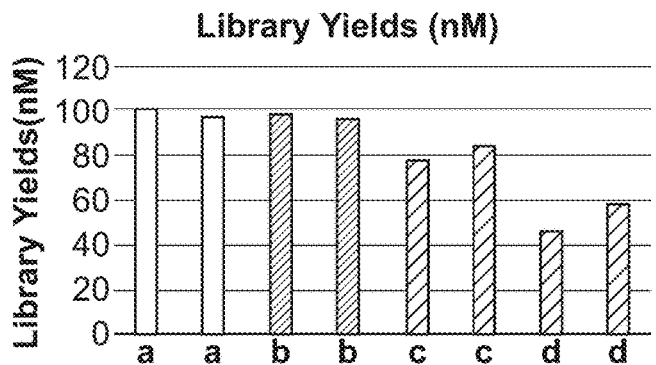

FIG. 42A

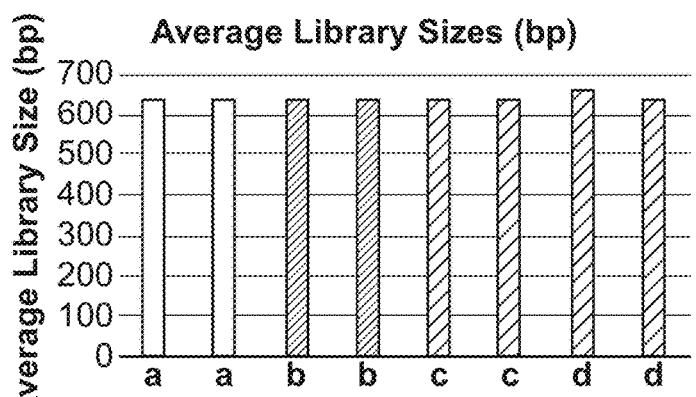

FIG. 42B a) Standard workflow with U hairpin + Digest
   Ligation to 5' and 3' end of hairpin adapter. Can include digestion (e.g., with a mixture of Uracil DNA Glycosylase (UDG) and Endonuclease VIII) before extension step
b) 3'phosphate hairpin
   Blocked ligation by 3'phosphate on hairpin
c) 3'phosphate hairpin + PNK exchange reaction
   Blocked ligation by 3'phosphate on hairpin and by removing 5' phosphate on gDNA in presence of ADP and PNK
d) 3'phosphate hairpin + rSAP phosphatase
   Blocked ligation by 3'phosphate on hairpin and by removing 5' phosphate on gDNA with rSAP phosphatase

Step 3: Epigenetic code quantification

| sequence id | start pos | 5mC | 5hmC | C | total |
|---|---|---|---|---|---|
| chr1 | 10469 | 0 | 1 | 1 | 2 |
| chr1 | 10471 | 0 | 1 | 1 | 2 |
| chr1 | 10484 | 2 | 0 | 0 | 2 |
| chr1 | 10489 | 2 | 0 | 0 | 2 |
| chr1 | 10493 | 1 | 0 | 1 | 2 |
| chr1 | 10497 | 1 | 0 | 0 | 1 |
| chr1 | 10525 | 1 | 0 | 0 | 1 |
| chr1 | 10542 | 1 | 0 | 2 | 3 |
| chr1 | 10563 | 0 | 0 | 3 | 5 |
| chr1 | 10571 | 0 | 1 | 4 | 5 |
| chr1 | 10577 | 1 | 0 | 4 | 6 |
| chr1 | 10579 | 0 | 0 | 6 | 6 |
| chr1 | 10589 | 0 | 0 | 6 | 7 |
| chr1 | 10609 | 0 | 1 | 6 | 7 |
| chr1 | 10617 | 0 | 0 | 7 | 7 |
| chr1 | 10620 | 0 | 0 | 6 | 7 |
| chr1 | 10631 | 2 | 0 | 0 | 9 |
| chr1 | 10633 | 0 | 1 | 8 | 9 |
| chr1 | 10636 | 2 | 2 | 6 | 10 |
| chr1 | 10638 | 3 | 1 | 6 | 10 |
| chr1 | 10641 | 3 | 1 | 7 | 11 |
| chr1 | 10644 | 3 | 0 | 6 | 11 |
| chr1 | 10650 | 5 | 1 | 4 | 11 |
| chr1 | 10660 | 5 | 1 | 6 | 14 |
| chr1 | 10662 | 1 | 1 | 8 | 14 |
| chr1 | 10665 | 8 | 0 | 3 | 14 |
| chr1 | 10667 | 6 | 3 | 5 | 16 |
| chr1 | 10670 | 10 | 1 | 4 | 17 |
| chr1 | 10673 | 12 | 0 | 7 | 21 |

Note: total inculdes error

Step 2: Intermediate Representation

| | | | | | |
|---|---|---|---|---|---|
| chr1 | 16141 | TG | 0 | 14 | + |
| chr1 | 16243 | 12 | 23 | 26 | + |
| chr1 | 16243 | 12 | 57 | 24 | - |
| chr1 | 16243 | 12 | 59 | 23 | - |
| chr1 | 16243 | 12 | 75 | 19 | + |
| chr1 | 16243 | 1G | 103 | 13 | + |
| chr1 | 16243 | 1G | 50 | 25 | + |
| chr1 | 16243 | 1G | 59 | 22 | + |
| chr1 | 16243 | 1G | 92 | 16 | + |
| chr1 | 16243 | CG | 102 | 14 | + |
| chr1 | 16243 | CG | 63 | 21 | + |
| chr1 | 16243 | CG | 65 | 20 | + |
| chr1 | 16243 | CG | 76 | 18 | + |
| chr1 | 16243 | CG | 86 | 17 | - |
| chr1 | 16243 | CG | 93 | 15 | + |
| chr1 | 16822 | 12 | 46 | 29 | + |
| chr1 | 16822 | 12 | 54 | 27 | - |

To Identity stranded reads we add in a "stranded" column

FIG. 47 (Cont.)

METHODS FOR ANALYZING NUCLEIC ACIDS

SUMMARY

In various embodiments, a method comprises: providing a forward polynucleotide and a cognate polynucleotide; determining a first identity of a first base at a locus of the forward polynucleotide and a second identity of a second base at or proximal to a corresponding locus of the cognate polynucleotide using sequencing; and using a computer comprising a processor, a memory, and instructions stored thereupon that, when executed, determine a value of a true base at a locus of an original polynucleotide corresponding to the locus of the forward polynucleotide based at least in part on the first identity of the first base and the second identity of the second base. In some cases, the second base is at the corresponding locus of the cognate polynucleotide. In some cases, the second base is proximal to the corresponding locus of the cognate polynucleotide. In some cases, the forward polynucleotide and cognate polynucleotide are linked. In some embodiments of the method, at any time point prior to sequencing, the forward polynucleotide and the cognate polynucleotide are (i) covalently linked via a hairpin; (ii) linked as a double-stranded polynucleotide via Watson-Crick base pairing; (iii) each coupled to a barcode; or (iv) any combination thereof. In some cases, the forward polynucleotide comprises a complementary deoxyribonucleic acid (cDNA) molecule or an amplicon thereof. In some cases, the method further comprises contacting an RNA nucleotide with a reverse transcriptase, biologically active fragment thereof, or derivative thereof to generate the forward polynucleotide. In some cases, the original polynucleotide comprises a deoxyribonucleic acid (DNA) polynucleotide isolated from a sample obtained from a subject. In some cases, the original polynucleotide comprises a cell free DNA (cfDNA) polynucleotide. In some cases, the forward polynucleotide is the original polynucleotide or a portion thereof. In some cases, the forward polynucleotide is an amplicon copy of the original polynucleotide. the value of the true base is determined to be a miscall if the first identity of the first base and the second identity of the second base, respectively, are determined to be any of the following combinations: adenine and adenine, adenine and cytosine, adenine and guanine, cytosine and adenine, cytosine and cytosine, cytosine and thymine, guanine and adenine, guanine and guanine, guanine and thymine, thymine and cytosine, thymine and guanine, or thymine and thymine. In some cases, the value of the true base is adenine if the first identity of the first base and the second identity of the second base are determined to be adenine and thymine, respectively. In some cases, the value of the true base is cytosine if the first identity of the first base and the second identity of the second base are determined to be cytosine and guanine, respectively. In some cases, the value of the true base is guanine if the first identity of the first base and the second identity of the second base are determined to be guanine and cytosine, respectively. In some cases, the value of the true base is thymine if the first identity of the first base and the second identity of the second base are determined to be thymine and adenine, respectively. In some cases, a false positive rate for determining the identity of the true base at the locus of the original polynucleotide is no higher than 1 in 100. In some cases, a false positive rate for determining the identity of the true base at the locus of the original polynucleotide is no higher than 1 in 1,000. In some cases, a false positive rate for determining the identity of the true base at the locus of the original polynucleotide is no higher than 1 in 10,000. In some cases, the false positive rate for determining the identity of the true base at the locus of the original polynucleotide is no higher than 1 in 100,000. In some cases, the false positive rate for determining the identity of the true base at the locus of the original polynucleotide is no higher than 1 in 1,000,000. In some cases, determining the second identity of the second base comprises sequencing a read polynucleotide, wherein the read polynucleotide is a cognate amplicon of the cognate polynucleotide. In some cases, the value of the true base is determined before aligning data generated during the sequencing to a reference nucleic acid sequence. In some cases, a mutation having a frequency of no more than 0.1% in a population comprising a subject from which the sample was obtained is detected at the locus of the original polynucleotide with a sensitivity of at least 90% using a locus coverage of no more than 450-fold, no more than 500-fold, no more than 700-fold, or no more than 1000-fold. In some cases, the method further comprises, generating the forward polynucleotide and cognate polynucleotide by conducting one or more chemical reactions or enzymatic reactions on the original polynucleotide or derivative thereof. In some cases, the method further comprises, generating the forward polynucleotide and cognate polynucleotide by conducting a deamination reaction. In some cases, the deamination reaction is conducted with a deaminase. In some cases, the deaminase is APOBEC or a fragment thereof. In some cases, the deamination reaction is conducted in a presence of a helicase or fragment thereof.

In various embodiments, a method comprises: (a) providing a forward polynucleotide and a cognate polynucleotide; (b) contacting the forward polynucleotide and, optionally, the cognate polynucleotide with bisulfite; (c) determining a first identity of a first base at a locus of the forward polynucleotide and a second identity of a second base at or proximal to a corresponding locus of the cognate polynucleotide using sequencing; and (d) using a computer comprising a processor, a memory, and instructions stored thereupon that, when executed, determine a value of a true base at a locus of an original polynucleotide corresponding to the locus of the forward polynucleotide based at least in part on the identity of the first base and the identity of the second base. In some cases, the second base is at the corresponding locus of the cognate polynucleotide. In some cases, the second base is proximal to the corresponding locus of the cognate polynucleotide. In some cases, the method further comprises contacting the forward polynucleotide and the cognate polynucleotide with an entity having DNA methyltransferase activity. In some cases, the contacting the forward polynucleotide and the cognate polynucleotide with the entity having DNA methyltransferase activity is performed before the contacting the forward polynucleotide and, optionally, the cognate polynucleotide with bisulfite. In some cases, the entity having DNA methyltransferase activity is DNA (cytosine-5)-methyltransferase 1 (DNMT1) or DNMT5. In some cases, the forward polynucleotide comprises a 5-methylcytosine, a 5-hydroxymethylcytosine, or both. In some cases, the forward polynucleotide and the cognate polynucleotide are linked by Watson-Crick basing pairing. In some cases, the forward polynucleotide and the cognate polynucleotide are further linked by a hairpin, a barcode, or both. In some cases, after the contacting with the entity having DNA methyltransferase activity, the cognate polynucleotide optionally comprises a 5-methylcytosine. In some cases, the value of the true base is determined to be a miscall if the first identity of the first base and the second identity of the second base, respectively, is determined to be any of the following combinations: adenine and adenine, adenine and cytosine, adenine and guanine, cytosine and adenine, cytosine and cytosine, cytosine and thymine, guanine and adenine, guanine and guanine, guanine and cytosine, thymine and cytosine, or thymine and thymine. In some cases, the value of the true base is adenine if the first identity of the first base and the second identity of the second bases are determined to be adenine and thymine, respectively. In some cases, the value of the true base is cytosine if the first identity of the first base and the second identity of the second base are determined to be thymine and guanine, respectively. In some cases, the value of the true base is guanine if the first identity of the first base and the second identity of the second bases are determined to be guanine and thymine, respectively. In some cases, the value of the true base is thymine if the first identity of the first base and the second identity of the second base are determined to be thymine and adenine, respectively. In some cases, the value of the true base is a methylated cytosine if the first identity of the first base and the second identity of the second base are determined to be cytosine and guanine, respectively. In some cases, the value of the true base is determined before aligning data generated during the sequencing to a reference nucleic acid sequence. In some cases, the method further comprises conducting a chemical or enzymatic reaction using said forward polynucleotide and said cognate polynucleotide.

In various embodiments, a method, comprises: (a) providing a forward polynucleotide and a cognate polynucleotide; (b) contacting the forward polynucleotide and, optionally, the cognate polynucleotide with an oxidizing agent; (c) determining a first identity of a first base at a locus of the forward polynucleotide and a second identity of a second base at or proximal to a corresponding locus of the cognate polynucleotide using sequencing; and (d) using a computer comprising a processor, a memory, and instructions stored thereupon that, when executed, determine a value of a true base at a locus of an original polynucleotide corresponding to the locus of the forward polynucleotide based at least in part on the identity of the first base and the identity of the second base. In some cases, the second base is at the corresponding locus of the cognate polynucleotide. In some cases, the second base is proximal to the corresponding locus of the cognate polynucleotide. In some cases, the oxidizing agent is a metal oxide. In some cases, the oxidizing agent is a ruthenate. In some cases, the oxidizing agent is potassium ruthenate. In some cases, the oxidizing agent is a methylcytosine dioxygenase. In some cases, the forward polynucleotide comprises a 5-methylcytosine, a 5-hydroxymethylcytosine, or both. In some cases, the forward polynucleotide and the cognate polynucleotide are linked by Watson-Crick basing pairing. In some cases, the forward polynucleotide and the cognate polynucleotide are further linked by a hairpin, a barcode, or both. In some cases, a method further comprises contacting the forward polynucleotide and the cognate polynucleotide with an entity having DNA methyltransferase activity. In some cases, the entity having DNA methyltransferase activity is selected from DNA (cytosine-5)-methyltransferase 1 (DNMT1) or DNA (cytosine-5)-methyltransferase 5 (DNMT5). In some cases, the method comprises contacting the forward polynucleotide and the cognate polynucleotide with an entity having DNA methyltransferase activity is performed after the contacting the forward polynucleotide and, optionally, the cognate polynucleotide with the oxidizing agent. In some cases, the method further comprises contacting the forward polynucleotide and optionally the cognate polynucleotide with a deamination agent. In some cases, the deamination agent is a deaminase. In some cases, the deaminase is APOBEC, or a fragment thereof. In some cases, the method further comprises contacting the forward polynucleotide and optionally the cognate polynucleotide with a helicase. In some cases, the deamination agent is bisulfite. In some cases, the value of the true base is determined to be a miscall if the first identity of the first base and the second identity of the second base, respectively, are determined to be any of the following combinations: adenine and adenine, adenine and cytosine, adenine and guanine, cytosine and adenine, cytosine and cytosine, cytosine and thymine, guanine and adenine, guanine and guanine, guanine and cytosine, thymine and cytosine, or thymine and thymine. In some cases, the value of the true base is adenine if the first identity of the first base and the second identity of the second base are determined to be adenine and thymine, respectively. In some cases, the value of the true base is cytosine or 5-hydroxymethylcytosine (5hmC) if the first identity of the first base and the second identity of the second base are determined to be thymine and guanine, respectively. In some cases, the value of the true base is guanine if the first identity of the first base and the second identity of the second base are determined to be guanine and thymine, respectively. In some cases, the value of the true base is thymine if the first identity of the first base and the second identity of the second base are determined to be thymine and adenine, respectively. In some cases, the value of the true base is a 5-methylcytosine (5mC) if the first identity of the first base and the second identity of the second base are determined to be cytosine and guanine, respectively. In some cases, the value of the true base is determined before aligning data generated during the sequencing to a reference nucleic acid sequence. In some cases, a false positive rate for determining the identity of the true base at the locus of the original polynucleotide is no higher than 1 in 100. In some cases, a false positive rate for determining the identity of the true base at the locus of the original polynucleotide is no higher than 1 in 1,000. In some cases, a false positive rate for determining the identity of the true base at the locus of the original polynucleotide is no higher than 1 in 10,000. In some cases, the false positive rate for determining the identity of the true base at the locus of the original polynucleotide is no higher than 1 in 100,000. In some cases, the false positive rate for determining the identity of the true base at the locus of the original polynucleotide is no higher than 1 in 1,000,000. In some cases, the method comprises, generating the forward polynucleotide and cognate polynucleotide, by conducting one or more chemical reactions or enzymatic reactions on the original polynucleotide or derivative thereof.

In various embodiments, a method, comprises: (a) providing a forward polynucleotide and a cognate polynucleotide; (b) contacting the forward polynucleotide and, optionally, the cognate polynucleotide with an agent that specifically glycosylates 5-hydroxymethylcytosine (5hmC); (c) determining a first identity of a first base at a locus of the forward polynucleotide and a second identity of a second base at or proximal to a corresponding locus of the cognate polynucleotide using sequencing; and (d) using a computer comprising a processor, a memory, and instructions stored thereupon that, when executed, determine a value of a true base at a locus of an original polynucleotide corresponding to the locus of the forward polynucleotide based at least in part on the identity of the first base and the identity of the second base. In some cases, the second base is at the corresponding locus of the cognate polynucleotide. In some cases, the second base is proximal to the corresponding locus of the cognate polynucleotide. In some cases, the method further comprises contacting the forward polynucleotide and the cognate polynucleotide with an entity having DNA methyltransferase activity. In some cases, the entity having DNA methyltransferase activity is selected from DNA (cytosine-5)-methyltransferase 1 (DNMT1) or DNA (cytosine-5)-methyltransferase 5 (DNMT5). In some cases, the contacting the forward polynucleotide and the cognate polynucleotide with the entity having DNA methyltransferase activity is performed after the contacting the forward polynucleotide and, optionally, the cognate polynucleotide with the agent that specifically glycosylates 5-hydroxymethylcytosine (5hmC). In some cases, the method further comprises contacting the forward polynucleotide and optionally the cognate polynucleotide with a deamination agent. In some cases, the deamination agent is a deaminase. In some cases, the deamination agent is APOBEC, or a fragment thereof. In some cases, the method further comprises, contacting the forward polynucleotide and optionally the cognate polynucleotide with a helicase. In some cases, the deamination agent is bisulfite. In some cases, the method further comprises contacting the forward polynucleotide and optionally the cognate polynucleotide with an oxidizing agent. In some cases, the oxidizing agent is a methylcytosine dioxygenase. In some cases, the methylcytosine dioxygenase is a ten-eleven translocation (TET) enzyme, or a derivative thereof. In some cases, the contacting the forward polynucleotide and, optionally, the cognate polynucleotide with the oxidizing agent is performed after the contacting the forward polynucleotide and the cognate polynucleotide with the entity having DNA methyltransferase activity. In some cases, the entity having DNA methyltransferase activity is selected from DNA (cytosine-5)-methyltransferase 1 (DNMT1) or DNA (cytosine-5)-methyltransferase 5 (DNMT5). In some cases, the method further comprises contacting the forward polynucleotide and the cognate polynucleotide with the agent that specifically glycosylates 5-hydroxymethylcytosine (5hmC). In some cases, the agent that specifically glycosylates 5hmC is β-glucosyltransferase. In some cases, the contacting the forward polynucleotide and the cognate polynucleotide with the agent that specifically glycosylates 5hmC is performed after the contacting the forward polynucleotide and, optionally, the cognate polynucleotide with the oxidizing agent. In some cases, the method further comprises contacting the forward polynucleotide and, optionally, the cognate polynucleotide with a deaminase. In some cases, the deaminase is selected from apolipoprotein B mRNA editing enzyme (APOBEC), a double-stranded DNA deaminase, or a fragment thereof. In some cases, the method comprises, prior to said contacting the forward polynucleotide and, optionally, the cognate polynucleotide with APOBEC, treating the forward polynucleotide and the cognate polynucleotide so that one or more loci of the forward polynucleotide and the cognate polynucleotide are not linked. In some cases, the treating comprises separating the first polynucleotide or a portion thereof from the second polynucleotide or a portion thereof. In some cases, said separating comprises contacting the forward polynucleotide and the cognate polynucleotide with a helicase. In some cases, said treating comprises contacting the forward polynucleotide and the cognate polynucleotide with a single-strand DNA-binding protein (SSB). In some cases, the value of the true base is determined to be a miscall if the first identity of the first base and the second identity of the second base, respectively, is determined to be any of the following combinations: adenine and adenine, adenine and cytosine, adenine and guanine, cytosine and adenine, cytosine and cytosine, cytosine and thymine, guanine and adenine, guanine and guanine, thymine and cytosine, thymine and thymine, guanine and cytosine if not preceded by cytosine and guanine, cytosine and guanine if not followed by guanine and cytosine, respectively, or cytosine and guanine if not followed by guanine and thymine, respectively. In some cases, the value of the true base is adenine if the first identity of the first base and the second identity of the second base are determined to be adenine and thymine, respectively. In some cases, the value of the true base is cytosine if the first identity of the first base and the second identity of the second bases are determined to be thymine and guanine, respectively. In some cases, the value of the true base is guanine if the first identity of the first base and the second identity of the second base are determined to be guanine and thymine, respectively. In some cases, the value of the true base is thymine if the first identity of the first base and the second identity of the second base are determined to be thymine and adenine, respectively. In some cases, the value of the true base is 5-methylcytosine (5mC) if the first identity of the first base and the second identity of the second base are determined to be cytosine and guanine, followed by guanine and cytosine, respectively, in a CpG context. In some cases, the value of the true base is 5-hydroxymethylcytosine (5hmC) if the first identity of the first base and the second identity of the second base are determined to be cytosine and guanine, respectively, followed by guanine and thymine, respectively, in a CpG context. In some cases, the value of the true base is determined before aligning data generated during the sequencing to a reference nucleic acid sequence. In some cases, the method further comprises contacting the forward polynucleotide and the cognate polynucleotide with a reducing agent. In some cases, said reducing agent is a borane or a derivative of a borane. In some cases, said reducing agent is selected from pyridine borane, 2-picoline borane (pic-borane), borane, diborane, tert-butylamine borane, ammonia borane, sodium borohydride (NaBH4), sodium cyanoborohydride (NaBH3CN), ethylenediamine borane, dimethylamine borane, sodium triacetoxyborohydride, morpholine borane, 4-methylmorpholine borane, trimethylamine borane, dicyclohexylamine borane, or lithium borohydride (LiBH4), or a salt thereof. In some cases, said reducing agent is pyridine borane. In some cases, said reducing agent comprises lithium aluminum hydride, sodium amalgam, amalgam, sulfur dioxide, dithionate, thiosulfate, iodide, hydrogen peroxide, hydrazine, diisobutylaluminum hydride, oxalic acid, carbon monoxide, cyanide, ascorbic acid, formic acid, dithiothreitol, beta-mercaptoethanol, or any combination thereof. In some cases, the value of the true base is determined to be a miscall if the first identity of the first base and the second identity of the second base, respectively, is determined to be any of the following combinations: adenine and adenine, adenine and cytosine, adenine and guanine, cytosine and adenine, cytosine and cytosine, cytosine and thymine, guanine and adenine, guanine and guanine, thymine and cytosine, thymine and thymine, guanine and thymine if not preceded by thymine and guanine, thymine and guanine if not followed by guanine and cytosine, respectively, or thymine and guanine if not followed by guanine and thymine, respectively. In some cases, the value of the true base is adenine if the first identity of the first base and the second identity of the second base are determined to be adenine and thymine, respectively. In some cases, the value of the true base is cytosine if the first identity of the first base and the second identity of the second base are determined to be thymine and guanine, respectively. In some cases, the value of the true base is guanine if the first identity of the first base and the second identity of the second base are determined to be guanine and thymine, respectively. In some cases, the value of the true base is thymine if the first identity of the first base and the second identity of the second base are determined to be thymine and adenine, respectively. In some cases, the value of the true base is 5-methylcytosine (5mC) if the first identity of the first base and the second identity of the second base are determined to be cytosine and guanine, followed by guanine and cytosine, respectively, in a CpG context. In some cases, the value of the true base is 5-hydroxymethyl-cytosine (5hmC) if the first identity of the first base and the second identity of the second base are determined to be cytosine and guanine, respectively, followed by guanine and thymine, respectively, in a CpG context. In some cases, a false positive rate for determining the identity of the true base at the locus of the original polynucleotide is no higher than 1 in 100. In some cases, a false positive rate for determining the identity of the true base at the locus of the original polynucleotide is no higher than 1 in 1,000. In some cases, a false positive rate for determining the identity of the true base at the locus of the original polynucleotide is no higher than 1 in 10,000. In some cases, the false positive rate for determining the identity of the true base at the locus of the original polynucleotide is no higher than 1 in 100,000. In some cases, the false positive rate for determining the identity of the true base at the locus of the original polynucleotide is no higher than 1 in 1,000,000. In some cases, the method further comprises, prior to (a), generating the forward polynucleotide and cognate polynucleotide by conducting one or more chemical reactions or enzymatic reactions on the original polynucleotide or derivative thereof. In some cases, at any time point prior to sequencing, the forward polynucleotide and the cognate polynucleotide are (i) covalently linked via a hairpin; (ii) linked as a double-stranded polynucleotide via Watson-Crick base pairing; (iii) each coupled to a barcode; or (iv) any combination thereof. In some cases, the method further comprises diagnosing a condition in the subject based at least in part on the value of the true base variant at the locus. In some cases, the condition is a cancer. In some cases, the cancer is selected from a sarcoma, a glioma, an adenoma, leukemia, bladder cancer, breast cancer, colorectal cancer, endometrial cancer, kidney cancer, liver cancer, lung cancer, melanoma, non-Hodgkin lymphoma, pancreatic cancer, prostate cancer, thyroid cancer. In some cases, the condition is a neurodegenerative condition. In some cases, the neurodegenerative condition is selected from Alzheimer's disease, frontotemporal dementia, amyotrophic lateral sclerosis, Parkinson's disease, spinocerebellar ataxia, spinal muscle atrophy, Lewy body dementia, or Huntington's disease. In some cases, the sequencing comprises Maxam-Gilbert sequencing, Sanger sequencing, or high-throughput sequencing. In some cases, the high-throughput sequencing comprises next generation sequencing or third-generation sequencing. In some cases, the third-generation sequencing is long-read sequencing.

In various embodiments, a method comprises: (a) deaminating a cytosine base of a double-stranded polynucleotide in a presence of a helicase to yield a deaminated cytosine base; (b) sequencing at least a portion of said double-stranded polynucleotide comprising said deaminated cytosine base or double-stranded derivative thereof to obtain sequencing data; and (c) processing said sequencing data to identify said cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said sequencing comprises sequencing at least a portion of both strands of said double-stranded polynucleotide or double-stranded derivative thereof. In some cases, the method comprises processing said sequencing data to identify said cytosine base with an accuracy of at least about 90%, at least about 95%, or at least about 99%. In some cases, the deaminating is performed with a deaminase. In some cases, said deaminase is an apolipoprotein B mRNA editing enzyme, catalytic polypeptide-like (APOBEC) enzyme, or a fragment thereof. In some cases, said helicase comprises an amino acid sequence that is at least about 70%, at least about 75%, at least about 80%, at least about 85%, at least about 90%, at least about 93%, at least about 95%, at least about 97%, or at least about 99% homologous to UvrD helicase, *Geobacillus sterothermophilus* Bad protein, a PcrA helicase, or a fragment thereof, or a fragment thereof. In some cases, said helicase is UvrD helicase, *Geobacillus sterothermophilus* Bad protein, PcrA helicase, or a fragment thereof. In some cases, the method further comprises, subjecting said double-stranded polynucleotide comprising said deaminated cytosine base to one or more reactions to generate said double-stranded derivative thereof, and comprises sequencing at least a portion of said double-stranded derivative thereof to obtain said sequencing data. In some cases, the method further comprises, providing a sample double-stranded polynucleotide comprising a forward strand and a reverse strand. In some cases, the method further comprises, separating said forward strand from said reverse strand. In some cases, the method further comprises using said forward strand in a nucleic acid extension reaction to generate said double-stranded polynucleotide. In some cases, said deaminating is performed with a deaminase. In some cases, said deaminase is an apolipoprotein B mRNA editing enzyme, catalytic polypeptide-like (APOBEC) enzyme, or a fragment thereof. In some cases, said helicase comprises an amino acid sequence that is at least about 70%, at least about 75%, at least about 80%, at least about 85%, at least about 90%, at least about 93%, at least about 95%, at least about 97%, or at least about 99% homologous to UvrD helicase, *Geobacillus sterothermophilus* Bad protein, a PcrA helicase, or a fragment thereof, or a fragment thereof. In some cases, said helicase is a UvrD helicase, *Geobacillus sterothermophilus* Bad protein, a PcrA helicase, or a fragment thereof. In some cases, said cytosine base is a methylcytosine base or a hydroxymethyl cytosine base. In some cases, the method further comprises, subjecting said double-stranded polynucleotide comprising said deaminated cytosine base to one or more reactions to generate said double-stranded derivative thereof, and comprises sequencing at least a portion of said double-stranded derivative thereof to obtain said sequencing data and processing said sequencing data to identify said cytosine base as a cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said forward strand comprises a methylated cytosine base and said method further comprises using said forward strand in a nucleic acid extension reaction that generates a modified double-stranded polynucleotide comprising (i) said forward strand comprising said methylated cytosine base and (ii) an additional reverse strand comprising said cytosine base. In some cases, the method further comprises, converting said methylated cytosine base to glucosylated hydroxymethylcystosine. In some cases, said methylated cytosine base is a methylcytosine base and said converting comprises subjecting said methylcytosine base to oxidation conditions to generate a hydroxymethylcytosine base and subjecting said hydroxymethylcytosine base to glucosylation conditions to generate said glucosylated hydroxymethylcytosine. In some cases, said methylated cytosine base is hydoxymethylcytosine and said converting comprises subjecting said hydroxymethylcytosine base to glucosylation conditions to generate said glucosylated hydroxymethylcytosine. In some cases, said deaminating is performed with a deaminase. In some cases, said deaminase is an apolipoprotein B mRNA editing enzyme, catalytic polypeptide-like (APOBEC) enzyme. or a fragment thereof. In some cases, said helicase comprises an amino acid sequence that is at least about 70%, at least about 75%, at least about 80%, at least about 85%, at least about 90%, at least about 93%, at least about 95%, at least about 97%, or at least about 99% homologous to UvrD helicase, *Geobacillus sterothermophilus* Bad protein, a PcrA helicase, or a fragment thereof. In some cases, said helicase is a UvrD helicase, *Geobacillus sterothermophilus* Bad protein, a PcrA helicase, or a fragment thereof. In some cases, the method further comprises subjecting said double-stranded polynucleotide comprising said deaminated cytosine base to one or more reactions to generate said double-stranded derivative thereof, and comprises sequencing at least a portion of said double-stranded derivative thereof to obtain said sequencing data. In some cases, the method comprises processing said sequencing data to identify said methylated cytosine base as a methylated cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In various embodiments, a method comprises: (a) deaminating a cytosine base of a double-stranded polynucleotide, in a presence of a helicase, with a deaminase to yield a deaminated cytosine base; (b) sequencing at least a portion of said double-stranded polynucleotide comprising said deaminated cytosine base or double-stranded derivative thereof to obtain sequencing data; and (c) processing said sequencing data to identify said cytosine base. In some cases, the method further comprises sequencing at least a portion of both strands of said double-stranded polynucleotide or double-stranded derivative thereof. In some cases, said deaminase is an apolipoprotein B mRNA editing enzyme, catalytic polypeptide-like (APOBEC) enzyme, or a fragment thereof. In some cases, said helicase comprises an amino acid sequence that is at least 90% homologous to UvrD helicase, *Geobacillus sterothermophilus* Bad protein, a PcrA helicase, or a fragment thereof. In some cases, said helicase is a UvrD helicase, *Geobacillus sterothermophilus* Bad protein, a PcrA helicase, or a fragment thereof. In some cases, the method further comprises, providing a sample double-stranded polynucleotide comprising a forward strand and a reverse strand. In some cases, the method further comprises, separating said forward strand from said reverse strand. In some cases, said separating comprises subjecting said forward strand to a nucleic acid extension reaction that generates said double-stranded polynucleotide. In some cases, said deaminase is an apolipoprotein B mRNA editing enzyme, catalytic polypeptide-like (APOBEC) enzyme, or a fragment thereof. In some cases, said helicase comprises an amino acid sequence that is at least about 70%, at least about 75%, at least about 80%, at least about 85%, at least about 90%, at least about 93%, at least about 95%, at least about 97%, or at least about 99%, homologous to UvrD helicase, *Geobacillus sterothermophilus* Bad protein, a PcrA helicase, or a fragment thereof. In some cases, said helicase is a UvrD helicase, *Geobacillus sterothermophilus* Bad protein, a PcrA helicase, or a fragment thereof. In some cases, said cytosine base is a methylcytosine base or a hydroxymethyl cytosine base. In some cases, the method comprises subjecting said double-stranded polynucleotide comprising said deaminated cytosine base to one or more reactions to generate said double-stranded derivative thereof, and comprises sequencing at least a portion of said double-stranded derivative thereof to obtain said sequencing data. In some cases, said forward strand comprises a methylated cytosine base and said separating comprises using said forward strand in a nucleic acid extension reaction that generates a modified double-stranded polynucleotide comprising (i) said forward strand comprising said methylated cytosine base and (ii) an additional reverse strand comprising said cytosine base. In some cases, the method further comprises converting said methylated cytosine base to glucosylated hydroxymethylcystosine. In some cases, said methylated cytosine base is a methylcytosine base and said converting comprises subjecting said methylcytosine base to oxidation conditions to generate a hydroxymethylcytosine base and subjecting said hydroxymethylcytosine base to glucosylation conditions to generate said glucosylated hydroxymethylcytosine. In some cases, said methylated cytosine base is hydoxymethylcytosine and said converting comprises subjecting said hydroxymethylcytosine base to glucosylation conditions to generate said glucosylated hydroxymethylcytosine. In some cases, said deaminase is an apolipoprotein B mRNA editing enzyme, catalytic polypeptide-like (APOBEC) enzyme, or a fragment thereof. In some cases, said helicase comprises an amino acid sequence that is at least about 70%, at least about 75%, at least about 80%, at least about 85%, at least about 90%, at least about 93%, at least about 95%, at least about 97%, or at least about 99% homologous to UvrD helicase, *Geobacillus sterothermophilus* Bad protein, a PcrA helicase, or a fragment thereof. In some cases, said helicase is a UvrD helicase, *Geobacillus sterothermophilus* Bad protein, a PcrA helicase, or a fragment thereof. In some cases, the method further comprises subjecting said double-stranded polynucleotide comprising said deaminated cytosine base to one or more reactions to generate said double-stranded derivative thereof, and comprises sequencing at least a portion of said double-stranded derivative thereof to obtain said sequencing data.

In various embodiments, provided herein is a kit, comprising: a deaminase; a helicase; and packaging and instructions therein to use said kit. In some cases, said deaminase is an apolipoprotein B mRNA editing enzyme, catalytic polypeptide-like (APOBEC) enzyme, or a fragment thereof. In some cases, the kit further comprises a methylcytosine dioxygenase. In some cases, said methylcytosine dioxygenase comprises a ten eleven translocation (TET) enzyme or fragment thereof. In some cases, the kit further comprises a deoxyribonucleic acid (DNA) glucosyltransferase. In some cases, said DNA glucosyltransferase comprises DNA beta-glucosyltransferase. In some cases, the kit further comprises a DNA methyltransferase. In some cases, said DNA methyltransferase comprises DNA methyltransferase 1 (DNMT1). In some cases, said helicase comprises an amino acid sequence that is at least about 70%, at least about 75%, at least about 80%, at least about 85%, at least about 90%, at least about 93%, at least about 95%, at least about 97%, or at least about 99% homologous to UvrD helicase, *Geobacillus sterothermophilus* Bad protein, a PcrA helicase, or a fragment thereof. In some cases, said helicase is a UvrD helicase, *Geobacillus sterothermophilus* Bad protein, a PcrA helicase, or a fragment thereof.

In various embodiments, a method, comprises: (a) contacting a polynucleotide comprising a base (e.g., a cytosine base) with one or more reagents that collectively transform said base to an altered base derived from said base, thereby generating a modified polynucleotide comprising said altered base; and (b) sequencing at least a portion of said modified polynucleotide comprising said altered base or derivative thereof to obtain sequencing data with a coverage of no more than 30-fold, of no more than 25-fold, of no more than 20-fold, of no more than 15-fold, or no more than 10-fold, of no more than 5-fold, or of no more than 2-fold; and (c) processing said sequencing data to identify said base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said modified polynucleotide or derivative thereof is a double-stranded polynucleotide. In some cases, said sequencing comprises sequencing at least a portion of both strands of said double-stranded polynucleotide. In some cases, the method comprises processing said sequencing data to identify said base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said cytosine base is a methylated cytosine base. In some cases, the method further comprises processing said sequencing data to identify said methylated base as cytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said one or more reagents comprise an oxidating agent. In some cases, said one or more reagents comprise a DNA-glucosyltransferase. In some cases, said one or more reagents comprise a deaminase. In some cases, said one or more reagents comprise a helicase. In some cases, said one or more reagents comprise a DNA methyltransferase. In some cases, the method further comprises, providing a sample double-stranded polynucleotide comprising a forward strand comprising said polynucleotide and a reverse strand. In some cases, the method further comprises separating said forward strand from said reverse strand. In some cases, said separating comprises using said forward strand in a nucleic acid extension reaction that generates a double-stranded polynucleotide comprising said polynucleotide. In some cases, said methylated base is a methylated cytosine base. In some cases, said one or more reagents comprise a deaminase and a helicase. In some cases, said sequencing comprises sequencing at least a portion of both strands of said double-stranded polynucleotide or double-stranded derivative thereof. In some cases, the method further comprises processing said sequencing data to identify said methylated cytosine base as cytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some embodiments, the polynucleotide is derived from a population of polynucleotides, and where a base frequency of the methylated cytosine base in the population of polynucleotides is less than or equal to 75%, less than or equal to 70%, less than or equal to 65%, less than or equal to 60%, less than or equal to 55%, less than or equal to 50%, less than or equal to 45%, less than or equal to 40%, less than or equal to 35%, less than or equal to 30%, less than or equal to 25%, less than or equal to 20%, less than or equal to 15%, less than or equal to 10%, less than or equal to 7%, less than or equal to 5%, less than or equal to 3%, or less than or equal to 1% or lower at a given locus.

In some cases, said methylated cytosine base comprises a methylcytosine base or a hydroxymethylcytosine base. In some cases, said methylated cytosine base comprises a methylcytosine base and said one or more reagents comprise an oxidating agent, a DNA glucosyltransferase, a deaminase and a helicase. In some cases, said methylated cytosine base comprises a hydroxymethylcytosine base and said one or more reagents comprise an oxidating agent, a DNA glucosyltransferase, a methyltransferase, a deaminase and a helicase. In some cases, said sequencing comprises sequencing at least a portion of both strands of said double-stranded polynucleotide or double-stranded derivative thereof. In some cases, the method further comprises processing said sequencing data to identify said methylated cytosine base as methylcytosine or hydroxymethylcytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some cases, said polynucleotide is a double-stranded polynucleotide, with strands covalently linked via a hairpin. In some cases, said forward strand and said reverse strand are covalently linked via a hairpin.

In various embodiments, a method, comprises: (a) providing a forward polynucleotide and a cognate polynucleotide; (b) contacting the forward polynucleotide and the cognate polynucleotide with an entity having DNA methyltransferase activity; (c) contacting the forward polynucleotide and optionally the cognate polynucleotide with an oxidizing agent; (d) determining an identity of a first base variant at a locus of the forward polynucleotide and an identity of a second base variant at a corresponding locus of the cognate polynucleotide using sequencing; and (e) using a computer comprising a processor, a memory, and instructions stored thereupon that, when executed, determine a value of a true base variant at a locus of an original polynucleotide corresponding to the locus of the forward polynucleotide based at least in part on the identity of the first base variant and the identity of the second base variant. In some cases, the method comprises contacting the forward polynucleotide and, optionally, the cognate polynucleotide with the oxidizing agent is performed after the contacting the forward polynucleotide and the cognate polynucleotide with the entity having DNA methyltransferase activity. In some cases, the entity having DNA methyltransferase activity is DNMT1 or DNMT5. In some cases, said oxidizing agent is a ten-eleven translocation (TET) enzyme. In some cases, the method comprises contacting the forward polynucleotide and the cognate polynucleotide with a reducing agent. In some cases, said reducing agent is a borane or a derivative of a borane. In some cases, said reducing agent is selected from pyridine borane, 2-picoline borane (pic-borane), borane, diborane, tert-butylamine borane, ammonia borane, sodium borohydride (NaBH4), sodium cyanoborohydride (NaBH3CN), ethylenediamine borane, dimethylamine borane, sodium triacetoxyborohydride, morpholine borane, 4-methylmorpholine borane, trimethylamine borane, dicyclohexylamine borane, or lithium borohydride (LiBH4), or a salt thereof. In some cases, said reducing agent is pyridine borane. In some cases, said reducing agent comprises lithium aluminum hydride, sodium amalgam, amalgam, sulfur dioxide, dithionate, thiosulfate, iodide, hydrogen peroxide, hydrazine, diisobutylaluminum hydride, oxalic acid, carbon monoxide, cyanide, ascorbic acid, formic acid, dithiothreitol, beta-mercaptoethanol, or any combination thereof. In some cases, the method comprises contacting the forward polynucleotide and, optionally, the cognate polynucleotide with an oxidizing agent before the contacting the forward polynucleotide and the cognate polynucleotide with the entity having DNA methyltransferase activity. In some cases, the oxidizing agent is a ruthenate. In some cases, the oxidizing agent is potassium ruthenate. In some cases, the value of the true base variant is determined to be a miscall if the determined identities of the first base and the second base, respectively, is any of the following combinations: adenine and adenine, adenine and cytosine, adenine and guanine, cytosine and adenine, cytosine and cytosine, cytosine and thymine, guanine and adenine, guanine and guanine, thymine and cytosine, thymine and thymine, guanine and thymine if not preceded by thymine and guanine, thymine and guanine if not followed by either guanine and cytosine, respectively, or guanine and thymine, respectively. In some cases, the value of the true base variant is adenine if the identities of the first and second base variants are adenine and thymine, respectively. In some cases, the value of the true base variant is cytosine if the identities of the first and second base variant are cytosine and guanine, respectively. In some cases, the value of the true base variant is guanine if the identities of the first and second base variants are guanine and cytosine, respectively. In some cases, the value of the true base variant is thymine if the identities of the first and second base variants are thymine and adenine, respectively. In some cases, the value of the true base variant is 5-methylcytosine (5mC) if the identities of the first and second base variants are thymine and guanine, followed by guanine and thymine, respectively, in a CpG context. In some cases, the value of the true base variant is 5-hydroxymethylcytosine (5hmC) if the identities of the first and second base variants are thymine and guanine, respectively, followed by guanine and cytosine, respectively, in a CpG context. In some cases, the method comprises diagnosing a condition in the subject based at least in part on the value of the true base variant at the locus. In some cases, the condition is a cancer. In some cases, the cancer is selected from a sarcoma, a glioma, an adenoma, leukemia, bladder cancer, breast cancer, colorectal cancer, endometrial cancer, kidney cancer, liver cancer, lung cancer, melanoma, non-Hodgkin lymphoma, pancreatic cancer, prostate cancer, thyroid cancer. In some cases, the condition is a neurodegenerative condition. In some cases, the neurodegenerative condition is selected from Alzheimer's disease, frontotemporal dementia, amyotrophic lateral sclerosis, Parkinson's disease, spinocerebellar ataxia, spinal muscle atrophy, Lewy body dementia, or Huntington's disease. In some cases, the sequencing comprises Maxam-Gilbert sequencing, Sanger sequencing, or high-throughput sequencing. In some cases, the high-throughput sequencing comprises next generation sequencing or third-generation sequencing. In some cases, the third-generation sequencing is long-read sequencing.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the compositions and methods are set forth with particularity in the appended claims. A better understanding of the features and advantages of the present compositions and methods will be obtained by reference to the following detailed description that sets forth illustrative embodiments, in which the principles of the compositions and methods are utilized, and the accompanying drawings (also "figure" and "FIG." herein), of which:

FIG. 13 depicts, among other things, calculations for average base call accuracy for a method for differentiating and identifying cytosine, mC, and hmC in a DNA sequence provided herein.

FIGS. 20A-20F show tables useful in determining a value of a base of a polynucleotide, in accordance with embodiments.

FIG. 25 shows tables useful in determining a value of a base of a polynucleotide, in accordance with embodiments.

FIG. 26 shows tables useful in determining a value of a base of a polynucleotide, in accordance with embodiments.

FIG. 28 depicts details of the sequencing data obtained from the NA24385 and NA24631 reference samples and used for variant calling.

FIG. 29 depicts example performance metrics for evaluating variant calling from the NA24385 and NA24631 reference samples.

FIG. 30 depicts example performance metrics for evaluating quality of variant calling from the NA24385 and NA24631 reference samples.

FIG. 31 depicts example performance metrics comparing the variant calling results from the NA24385 and NA24631 reference samples.

FIG. 32 depicts example performance metrics comparing the variant calling results from the NA24385 and NA24631 reference samples.

FIG. 33A depicts, among other things, sequencing lane configurations and number of sequencing read chunks, each consisting of 10 million read pairs, produced for the NA24631 and NA24385 reference samples.

FIG. 33B, depicts among other things, generation of a mix-in sample from the mixing of NA24385 and NA24631 reference samples.

FIG. 34 depicts, among other things, example performance metrics for sequencing data obtained from a down-sampled NA24385 sample.

FIG. 35 depicts, among other things, example performance metrics for sequencing data obtained from a down-sampled NA24385 sample.

FIG. 36A depicts false-positive calls obtained from sequencing of the NA24385/NA24631 mix-in sample.

FIG. 36B depicts singleton error calls obtained from sequencing of the NA24385 and NA24631 samples.

FIG. 37 shows the error suppression aspects of the two-base sequencing base-calling method.

FIG. 42A depicts example library yields from samples prepared using a workflow with Uracil DNA glycosylase (UDG) and DNA glycosylase-lyase Endonuclease VIII (condition a) compared to a workflow that does not involve them (conditions b-d). FIG. 42B depicts example size of library yields (in base pairs) from samples prepared using a workflow with Uracil DNA glycosylase (UDG) and DNA glycosylase-lyase Endonuclease VIII (condition a) compared to a workflow that does not involve them (conditions b-d).

FIG. 45A shows the first operation of alignment with the reference genome. FIG. 45B shows the next operation involving generating an intermediate representation file containing epigenetic code information. FIG. 45C shows the next operations involving the quantification of the epigenetic information contained in the intermediate representation file.

FIG. 46A shows the workflow for generating an alignment file of the sample sequencing read with the reference genome. FIG. 46B details the operations in generating an intermediate representation file containing epigenetic code information and strand information. FIG. 46C provides a detailed workflow for the quantification of the epigenetic information contained in the intermediate representation file.

DETAILED DESCRIPTION

Figure 1A:
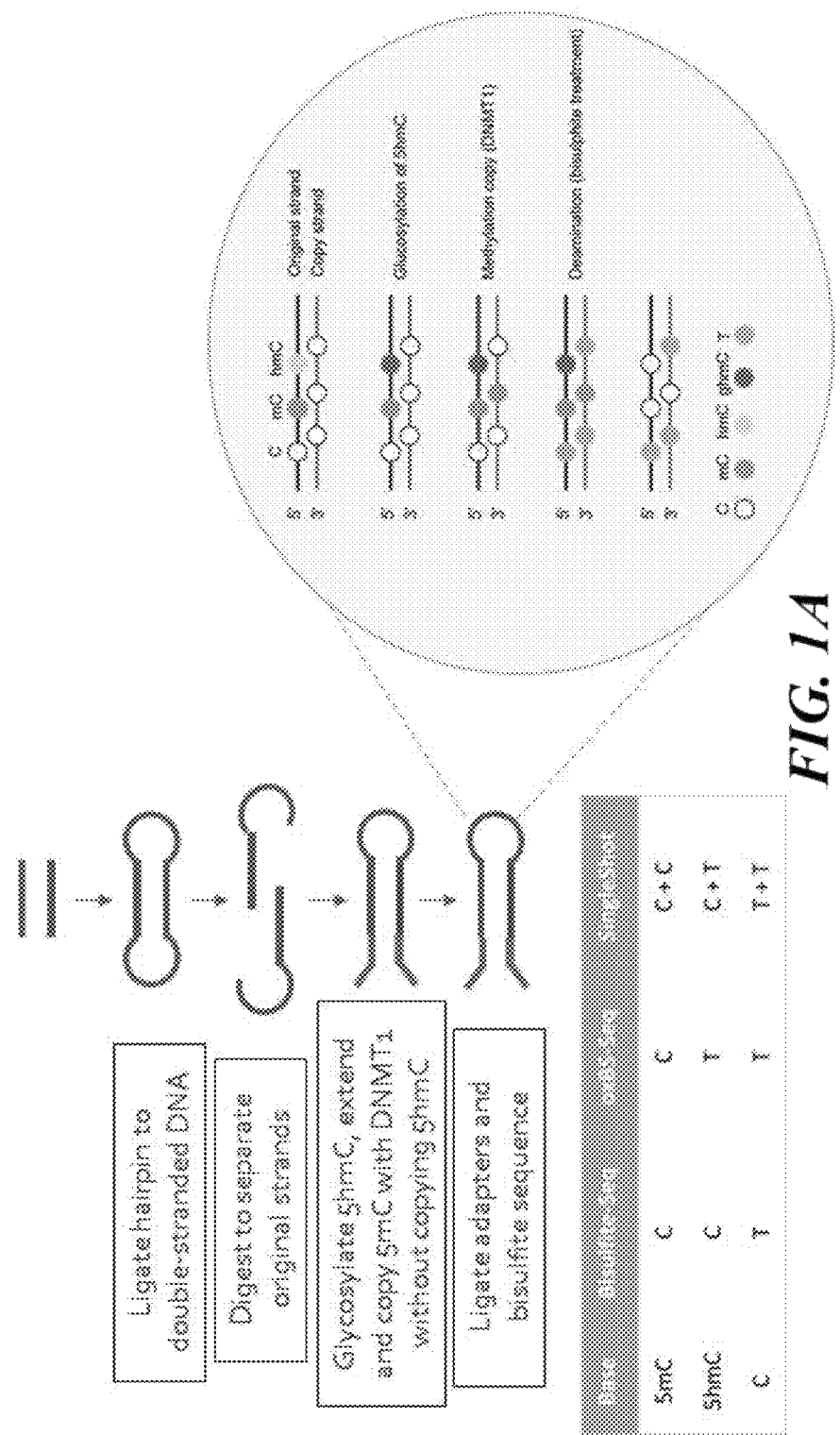
FIGS. 1A and 1B depict a method for differentiating and identifying cytosine, 5-methylcytosine (mC), and 5-hydroxymethylcytosine (hmC) in a deoxyribonucleic acid (DNA) sequence, in accordance with embodiments. In various aspects, the method can employ, for example, glucosylation, methylation, and deamination.

While various embodiments of the compositions and methods have been shown and described herein, it will be obvious to those skilled in the art that such embodiments are provided by way of example only. Numerous variations, changes, and substitutions may occur to those skilled in the art without departing from the compositions and methods. It should be understood that various alternatives to the embodiments described herein may be employed.

Disclosed herein are methods, systems, and compositions that can significantly increase both the efficiency and the accuracy of nucleic acid sequencing over existing technologies. For example, two-base sequencing methods and systems disclosed herein can circumvent errors introduced during sequencing (e.g., via high quality substitution errors that can occur at a rate of about 1 in every 1,000 sequenced bases using current technologies). In contrast, methods and systems disclosed herein can yield false positive rates at a rate of approximately 1 in 10,000 bases, for example, by leveraging internal logic comparisons of two-base sequencing methods and systems. In many cases, the ability to screen for miscalled bases in a sequencing read, for example, before alignment of individual reads against a reference genome, can drastically increase both the confidence that bases called as mutations in a sequencing read are true mutations (e.g., as opposed to miscalls resulting from, for example, a substitution error) and the efficiency of post-sequencing analysis of reads. These benefits resulting from the methods and systems presented herein apply to the full range of applications employing nucleic acid sequencing. For example, analysis of low frequency mutations (e.g., mutations having a prevalence of 0.1% or less) can be completed at an identical sensitivity with an order of magnitude less read coverage than existing technologies in clinical, basic science, or applied science settings, dramatically reducing cost and technical complexity. In many cases, two-base sequencing methods and systems presented herein improve the power of detecting mutations, e.g., because sequencing errors (e.g., substitution errors resulting from sequencing) are screened out of results (e.g., in the form of an error code (e.g., as shown in FIGS. 20A-20F) that can be assigned a value of a miscall, in some embodiments). In many cases, the depth of coverage in sequencing rare mutations (e.g., mutations occurring at a rate of less than 0.01% in a population that is required to obtain high confidence identification of mutations (e.g., in an original polynucleotide of a sample) can be greatly reduced using two-base sequencing methods and systems presented herein. Accordingly, high-confidence analysis of rare genetic mutations in low-copy sample sources (e.g., liquid biopsies, such as clinical or pre-clinical peripheral blood samples) is possible using the methods and systems disclosed herein.

In some cases, methods and systems disclosed herein can achieve a sensitivity of at least 90% (or at least 95%, or at least 97%, or at least 99% or at least 99.9%, or at least 99.99%, or at least 99.999%), for mutations having a prevalence of no more than 0.1% with no more than 500 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.1% with no more than 5 fold coverage to 25 fold coverage, 10 fold coverage to 50 fold coverage, 100 fold coverage to 500 fold coverage. 500 fold coverage to 1,000 fold coverage, 500 fold coverage to 2,500 fold coverage, 500 fold coverage to 4,000 fold coverage, 500 fold coverage to 5,000 fold coverage, 1,000 fold coverage to 2,500 fold coverage, 1,000 fold coverage to 4,000 fold coverage, 1,000 fold coverage to 5,000 fold coverage, 2,500 fold coverage to 4,000 fold coverage, 2,500 fold coverage to 5,000 fold coverage, or 4,000 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.1% with no more than 5 fold coverage, 10 fold coverage, 25 fold coverage, 50 fold coverage, 75 fold coverage, 100 fold coverage, 200 fold coverage, 300 fold coverage, 400 fold coverage, 500 fold coverage, 750 fold coverage, 1,000 fold coverage, 2,500 fold coverage, 4,000 fold coverage, or 5,000 fold coverage.

In some cases, methods and systems disclosed herein can achieve a sensitivity of at least 90% (or at least 95%, or at least 97%, or at least 99% or at least 99.9%, or at least 99.99%, or at least 99.999%), for mutations having a prevalence of no more than 0.01% with no more than 500 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.01% with no more than 5 fold coverage to 25 fold coverage, 10 fold coverage to 50 fold coverage, 100 fold coverage to 500 fold coverage. 500 fold coverage to 1,000 fold coverage, 500 fold coverage to 2,500 fold coverage, 500 fold coverage to 4,000 fold coverage, 500 fold coverage to 5,000 fold coverage, 1,000 fold coverage to 2,500 fold coverage, 1,000 fold coverage to 4,000 fold coverage, 1,000 fold coverage to 5,000 fold coverage, 2,500 fold coverage to 4,000 fold coverage, 2,500 fold coverage to 5,000 fold coverage, or 4,000 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.01% with no more than 5 fold coverage, 10 fold coverage, 25 fold coverage, 50 fold coverage, 75 fold coverage, 100 fold coverage, 200 fold coverage, 300 fold coverage, 400 fold coverage, 500 fold coverage, 750 fold coverage, 1,000 fold coverage, 2,500 fold coverage, 4,000 fold coverage, or 5,000 fold coverage.

In some cases, methods and systems disclosed herein can achieve a sensitivity of at least 90% (or at least 95%, or at least 97%, or at least 99% or at least 99.9%, or at least 99.99%, or at least 99.999%), for mutations having a prevalence of no more than 0.001% with no more than 500 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.001% with no more than 5 fold coverage to 25 fold coverage, 10 fold coverage to 50 fold coverage, 100 fold coverage to 500 fold coverage. 500 fold coverage to 1,000 fold coverage, 500 fold coverage to 2,500 fold coverage, 500 fold coverage to 4,000 fold coverage, 500 fold coverage to 5,000 fold coverage, 1,000 fold coverage to 2,500 fold coverage, 1,000 fold coverage to 4,000 fold coverage, 1,000 fold coverage to 5,000 fold coverage, 2,500 fold coverage to 4,000 fold coverage, 2,500 fold coverage to 5,000 fold coverage, or 4,000 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.001% with no more than 5 fold coverage, 10 fold coverage, 25 fold coverage, 50 fold coverage, 75 fold coverage, 100 fold coverage, 200 fold coverage, 300 fold coverage, 400 fold coverage, 500 fold coverage, 750 fold coverage, 1,000 fold coverage, 2,500 fold coverage, 4,000 fold coverage, or 5,000 fold coverage.

In some cases, methods and systems disclosed herein can achieve a sensitivity of at least 90% (or at least 95%, or at least 97%, or at least 99% or at least 99.9%, or at least 99.99%, or at least 99.999%), for mutations having a prevalence of no more than 0.0001% with no more than 500 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.0001% with no more than 5 fold coverage to 25 fold coverage, 10 fold coverage to 50 fold coverage, 100 fold coverage to 500 fold coverage. 500 fold coverage to 1,000 fold coverage, 500 fold coverage to 2,500 fold coverage, 500 fold coverage to 4,000 fold coverage, 500 fold coverage to 5,000 fold coverage, 1,000 fold coverage to 2,500 fold coverage, 1,000 fold coverage to 4,000 fold coverage, 1,000 fold coverage to 5,000 fold coverage, 2,500 fold coverage to 4,000 fold coverage, 2,500 fold coverage to 5,000 fold coverage, or 4,000 fold coverage to 5,000 fold coverage. In some cases, methods and systems disclosed herein can achieve a sensitivity of at least 90% (or at least 95%, or at least 97%, or at least 99% or at least 99.9%, or at least 99.99%, or at least 99.999%) for mutations having a prevalence of no more than 0.0001% with no more than 5 fold coverage, 10 fold coverage, 25 fold coverage, 50 fold coverage, 75 fold coverage, 100 fold coverage, 200 fold coverage, 300 fold coverage, 400 fold coverage, 500 fold coverage, 750 fold coverage, 1,000 fold coverage, 2,500 fold coverage, 4,000 fold coverage, or 5,000 fold coverage.

In some cases, methods and systems disclosed herein can achieve a false positive rate no higher than 1 in 1,000 to 1 in 10,000, 1 in 100 to 1 in 10,000, 1 in 1,000 to 1 in 100,000, or 1 in 100 to 1 in 1,000,000. In some cases, methods and systems disclosed herein can achieve a false positive rate no higher than 1 in 1,000 to 1 in 2,000, 1 in 1,000 to 1 in 5,000, 1 in 1,000 to 1 in 10,000, 1 in 2,000 to 1 in 5,000, 1 in 2,000 to 1 in 10,000, or 1 in 5,000 to 1 in 10,000. In some cases, methods and systems disclosed herein can achieve a false positive rate no higher than in 1 in 100, 1 in 500, 1 in 1,000, 1 in 2,000, 1 in 5,000, 1 in 10,000, 1 in 50,000, 1 in 100,000, 1 in 500,000, 1 in 1,000,000 or lower.

The systems and methods presented herein, which may utilize a two-base sequencing framework, also represent utility in both 4-base genome contexts (e.g., analyses comprising no more than the four classic nucleic acid bases: cytosine (C), guanine (G), adenine (A), and thymine (T)) and expanded 5- and 6-base genome contexts (e.g., 5-base analyses capable of distinguishing a modified base (e.g., methylated cytosine) from an unmodified base (e.g., unmethylated cytosine); 6-base analyses capable of distinguishing different modified and unmodified bases from one another such as, for example, distinguishing cytosine, 5-methylcytosine (5mC) and 5-hydroxymethylcytosine (5hmC) from one another). Until this point, a practical system for distinguishing all six bases (e.g., C, G, A, T, 5mC, and 5hmC) has proven elusive. Accordingly, the methods and systems disclosed herein offer new avenues for analysis of the presence or absence of epigenetic modifications (e.g., methylated cytosines) in a polynucleotide sample. In 5-base analyses, a modified base can be a methylated cytosine (mC) or a 5-hydroxymethylcytosine (5hmC).

DNA methylation can be an epigenetic modification that can play a role in regulating gene expression and, consequently, can influence a variety of biological processes and diseases. The addition of a methyl group to a base present in a nucleotide of a polynucleotide, for example at the 5' position of a cytosine residue, can be a mechanism in gene expression, chromatin structure regulation, or both. The functional presence of this methylated nucleotide, e.g., 5mC (5-methylcytosine), in gene promoters can be associated with transcriptional repression, in some cases due to structural chromatin alterations, while the absence of 5mC can be linked with transcriptional activity.

Methylation of cytosines to form 5-methylcytosine (5mC or mC), e.g., at cytosines followed by guanine residues (e.g., cytosine-phosphate-guanine motifs, or CpGs), can be an epigenetic mark with important roles in mammalian development and tissue specificity, genomic imprinting, and environmental responses. Dysregulation of 5mC can cause aberrant gene expression, and in some cases can affect cancer risk, progression or treatment response. 5-hydroxymethylcytosine (5hmC or hmC) can be an intermediate in the cell's active DNA demethylation pathway with tissue-specific distribution affecting gene expression and carcinogenesis.

A base on a first polynucleotide (e.g., a cytosine or guanine) can be proximal to a base on a second polynucleotide (e.g., a guanine or cytosine, respectively), e.g., in a CpG context, for instance, wherein the first and second polynucleotides are hybridized (e.g., in a double-stranded DNA polynucleotide). In some cases, a first base that is proximal to a second base can be adjacent (such as, for example, next to) to the second base, for instance wherein two bases are in a CpG context. In some cases, a second base in a cognate polynucleotide may be proximal (e.g., adjacent to, next to) to a base that is at a corresponding locus (e.g., a base-pairing site) to a first base of a forward polynucleotide. In many cases, a first base on a first polynucleotide can be said to be paired with a second base on a second polynucleotide when the first and second bases can achieve Watson-Crick base pairing (e.g., adenine-thymine, cytosine-guanine, 5hmC-guanine, or 5mC-guanine), for instance when the first and second polynucleotides are hybridized, e.g., in a double-stranded DNA polynucleotide.

Gene body DNA methylation (as used herein, methylation can mean addition of or the presence of a methyl group on a base of a nucleic acid; the methyl group can be in an oxygenated or unoxygenated state; an unoxygenated methyl group can be e.g., methyl; an oxygenated methyl group can be a hydroxymethyl, a formyl group, a carboxylic acid group, or a salt of carboxylic acid) can play a role in repetitive DNA elements' silencing and alternative splicing. DNA methylation can be associated with several biological processes such as genomic imprinting, transposon inactivation, stem cell differentiation, transcription repression, and inflammation. DNA methylation profiles can in some cases be inherited through cell division and sometimes through generations. Since methyl marks can play a very relevant role in both physiologic and pathologic conditions, there may be significant application for profiling DNA methylation to answer biological questions. Moreover, uncovering of DNA methylation genomic regions can be appealing to translational research because methyl sites can be modifiable by pharmacologic intervention.

Two-Base Sequencing Methods and Systems

Two-base sequencing methods and systems presented herein can be used to reduce uncertainty and overall error rate in the determination of a sequence of a polynucleotide (e.g., an original DNA polynucleotide), for example, by offering methods that include internal verification of base reads, without requiring alignment to a reference genome (or reference nucleic acid sequence). In some embodiments, this can be accomplished by comparing the value of a first base determined at a locus of a first polynucleotide (e.g., a forward polynucleotide) and the value of a second base determined at a second (e.g., associated) polynucleotide, such as a cognate polynucleotide (which can be a cognate amplicon of the first polynucleotide) or an amplicon of a cognate polynucleotide (e.g., a read polynucleotide, which can be a cognate amplicon of the cognate polynucleotide). A mismatch (e.g., as assessed using Watson-Crick base-pairing logic) between the first and second determined base values may thus indicate a polymerase substitution error, in many embodiments. In such embodiments, over three-quarters of all possible false positive base calls may be due to a polymerase error at a locus in the first polynucleotide and a second polymerase error at a corresponding locus of the second polynucleotide, wherein the second polymerase error may be the inverse base change to result in a false positive base call, which is a vanishingly unlikely sequence of events. For example, a cytosine to adenine polymerase substitution error in the generation of a cognate polynucleotide from a first polynucleotide may require a thymine to guanine polymerase substitution error (and no other substitution error) in the generation of a read polynucleotide (e.g., wherein the read polynucleotide is a cognate amplicon of the cognate polynucleotide) to generate a false positive base call in over three-quarters of all possible false positive base calls in such embodiments. In some cases, the remaining scenarios in which a single (e.g., polymerase) substitution error can possibly cause a false positive base call in the two-base sequencing methods and systems presented herein (e.g., adenine-to-guanine or guanine-to-adenine substitutions) can result from two specific substitution errors, which can have an occurrence rate of 1 in 10,000 or less than 1 in 10,000, in many embodiments. Indeed, adenine-to-guanine and guanine-to-adenine substitutions occur at a lower rate than other polymerase substitutions, in many cases.

In many embodiments, if the two determined base values are consistent with one another (e.g., as assessed by applying Watson-Crick base-pairing logic), it can be concluded with high certainty that the determined value of the first base is accurate with respect to the true identity of a base of the original polynucleotide at the corresponding locus (e.g., because the largest source of substitution errors in reads of the first and second polynucleotides is determined by polymerase fidelity, which may occur at a rate on the order of 1 in 10,000 bases). In many embodiments, if the two determined base values are inconsistent with one another (e.g., as assessed by applying Watson-Crick base-pairing logic), it can be concluded with high certainty that the determined value of the first base is erroneous, and the base call can be determined to be an error. Advantageously, the comparison of two associated base calls from associated polynucleotides (e.g., a forward polynucleotide and a cognate polynucleotide or a forward polynucleotide and an amplicon of a cognate polynucleotide) using two-base sequencing methods and systems presented herein can effectively circumvent the problem of substitution errors introduced during sequencing, for example, by avoiding the need to verify (e.g., through alignment) a given base call against other, independently produced and sequenced polynucleotides and against a reference genome to determine if a substitution error has occurred. This can result in significant reductions to false positive rates (e.g., as compared to existing technologies).

In contrast, existing sequencing technologies can be limited by significant error and uncertainty, for example, resulting from substitution errors introduced during sequencing, which can be introduced at a high rate (e.g., about 1 in 50 bases). As a result, the base calls of sequencing reads obtained with existing technologies, which are also subject to polymerase substitution errors, may be verified. Verification of a base call at a particular locus using existing sequencing technologies relies on barcoding of sequenced polynucleotides (e.g., with unique molecular identifies, UMIs) and subsequent alignment of the base call with a reference sequence (e.g., a reference genome) and with base calls of reads from other, independently produced and sequenced polynucleotides, which may or may not also comprising substitution errors resulting from the sequencing method. As a result, great depth of sequencing is required to achieve confidence that a mismatch between a given base call and a value of a reference genome at the same locus represents a true mutation in the sequenced polynucleotide and not a substitution error resulting from the sequencing process. For example, 5,000-fold coverage can be required to achieve 91% sensitivity for mutations having a prevalence of 0.1% in a population, using existing sequencing technologies.

Two-base sequencing methods presented herein can be used to determine a value (e.g., an identity) of a base of an original polynucleotide (e.g., a true base of the original polynucleotide). In some cases, determining the value of a base of an original polynucleotide comprises determining a mutation in the original polynucleotide. For example, some two-base sequencing methods disclosed herein can result in highly accurate and efficient identification of mutations in sample polynucleotides, such as tumor DNA molecules or fragments thereof derived from a liquid biopsy sample obtained from a subject. A base can be detected or otherwise determined. A value (e.g., an identity) of a base (e.g., a first base on a first polynucleotide, such as a forward polynucleotide, or a second base on a second polynucleotide, such as a cognate polynucleotide) can be determined by sequencing. In some cases, a value (e.g., an identity) of a base (e.g., a true base of an original polynucleotide) can be determined using a computer program (e.g., comprising instructions for the analysis of sequencing data and/or for performing one or more operations of a method presented herein, such as 6-letter, 5-letter, or 4-letter sequencing). In some cases, such a computer program can be stored on a memory of a computer. In some cases, the computer can comprise instructions for operating a sequencer and/or operating a device capable of performing polymerase chain reaction (PCR) (e.g., a programmable thermocycler).

In many cases, two-base sequencing comprises determining a value (e.g., an identity) of a base (e.g., a true base) of an original polynucleotide based on the identity of a first base on a first polynucleotide (e.g., a forward polynucleotide or reverse polynucleotide) and the identity of a second base on a second polynucleotide (e.g., a cognate polynucleotide or an amplicon of a cognate polynucleotide). A value (e.g., identity) of a base can be a nucleic acid base. For example, a value (e.g., identity) of a base can be determined to be adenine, guanine, thymine, cytosine, 5-methylcytosine, or 5-hydroxymethylcytosine. In some cases, a value of a base can be determined to be a methylated cytosine. For example, in some cases, a value of a base determined to be a methylated cytosine can be either 5-methylcytosine or 5-hydroxymethylcytosine (e.g., and distinguished from adenine, guanine, thymine, and cytosine). In some cases, a value of a base can be determined to be either cytosine or 5-hydroxymethylcytosine (e.g., and distinguished from adenine, guanine, thymine, and 5-methylcytosine). In some cases, methods and systems presented herein can be used to distinguish between six different bases (e.g., 6-letter sequencing). For example, some methods and systems presented herein can be used to distinguish between the bases: adenine, guanine, thymine, cytosine, 5-methylcytosine, and 5-hydroxymethylcytosine. In some cases, methods and systems presented herein can be used to distinguish between five different groups of bases (e.g., 5-letter sequencing). For example, some embodiments of methods and systems presented herein comprising oxidative bisulfite processing (e.g., which can comprise exposure of a first polynucleotide, and in some cases a second polynucleotide, for example, the first polynucleotide's cognate polynucleotide, to a ruthenate, such as potassium ruthenate) allow for distinguishing between adenine, guanine, and thymine or between any of those bases and one of cytosine and 5-hydroxymethylcytosine. In some cases, some methods and system presented herein can be used to distinguish between adenine, guanine, thymine, cytosine, and methylated cytosine (e.g., wherein adenine, guanine, thymine, cytosine can be distinguished from one another and from a methylated cytosine, such as 5-methylcytosine or 5-hydroxymethylcytosine). In some cases, methods and systems presented herein can be used to distinguish between four bases (e.g., 4-letter sequencing). For example, some methods and systems presented herein can be used to distinguish between adenine, guanine, thymine, and cytosine. In some cases, determined values of a first base (e.g., of a first polynucleotide) and a second base (e.g., of a second polynucleotide) are biologically impossible combinations, which can imply a substitution error (e.g., from sequencing). Error codes can be assigned as values for bases (e.g., of an original polynucleotide) for which the combination of the determined first and second bases form an impossible combination (e.g., as shown in FIGS. 20A-20F). In some cases, the value of the true base (e.g., of an original polynucleotide) is determined to be a miscall if the determined identities of the first base and the second base are not expected by Watson-Crick base pairing or not as expected given the chemical or enzymatic transformations performed. For instance, in 4-letter sequencing using two-base sequencing methods presented herein, any of the following combinations: adenine and adenine, adenine and cytosine, adenine and guanine, cytosine and adenine, cytosine and cytosine, cytosine and thymine, guanine and adenine, guanine and guanine, guanine and cytosine, thymine and cytosine, or thymine and thymine, may be identified as an error.

In many cases, the identity (e.g., value) of a base (e.g., of an original polynucleotide) is determined before the determined (e.g., detected) sequence of a first polynucleotide, second polynucleotide, read polynucleotide, and/or original polynucleotide are aligned with a reference nucleic acid sequence (e.g., a reference genome or portion thereof). In many cases, the nucleic acid sequences of the first and second are aligned with one another prior to determining an identity (e.g., value) of a base (e.g. of an original polynucleotide), e.g., in order to determine the base-pairing and regions of CpG context of the first polynucleotide relative to the second polynucleotide. In some cases, methods and systems presented herein can comprise aligning one or more of the first polynucleotide nucleic acid sequence (or a portion thereof), the second polynucleotide nucleic acid sequence (or a portion thereof), or the read polynucleotide nucleic acid sequence (or a portion thereof) before one or more bases have been determined.

Reagents and Methods

Methods and systems presented herein can comprise providing and/or (e.g., chemical) processing a double-stranded (e.g., duplex) DNA polynucleotide. A double-stranded DNA polynucleotide can comprise a first polynucleotide described herein. A double-stranded DNA can comprise a second polynucleotide. In some cases, a first polynucleotide is linked to (e.g., hybridized to) a second polynucleotide in the double-stranded DNA.

In many cases, a first polynucleotide is the original polynucleotide, or a portion thereof. In some cases, a first polynucleotide is an amplification product of the original polynucleotide, or a portion thereof. In some cases, a first polynucleotide is an amplicon copy of the original polynucleotide, or a portion thereof. For example, a first polynucleotide may be a copy of the original polynucleotide (or a portion thereof) having the same sequence orientation relative to their respective 5-prime (5') and 3-prime (3') ends. The original polynucleotide and one or more of its amplicons (e.g., the first polynucleotide) can be contacted with a methyltransferase (e.g., DNMT1 or DNMT5), e.g., to transfer methylation marks to the amplicon(s). In some cases, a first polynucleotide is a forward strand (e.g., forward polynucleotide) of a double-stranded (e.g., duplexed) DNA molecule. In some cases, a first polynucleotide is a reverse strand (e.g., reverse polynucleotide) of a double-stranded (e.g., duplexed) DNA molecule. A second polynucleotide can be an amplification product (e.g., an amplicon) of the first polynucleotide or a portion thereof. In many cases, a second polynucleotide is a cognate polynucleotide. A second polynucleotide (e.g., a cognate polynucleotide) can have a nucleic acid sequence complementary to all or a portion of the nucleic acid sequence of the first polynucleotide. In many cases, a second polynucleotide (e.g., cognate polynucleotide) can be provided by performing polymerase chain reaction on all or a portion the first polynucleotide (e.g., the forward polynucleotide), for example using a nucleic acid primer (e.g., which may or may not comprise a biotin tag) capable of hybridizing to a portion of the first polynucleotide or a hairpin polynucleotide (e.g., which may or may not comprise a biotin tag) ligated to an end (e.g., the 3' end) of the first polynucleotide.

A first polynucleotide can comprise an original polynucleotide or a fragment thereof. In some cases, the original polynucleotide is an artificial molecule. In some cases, the original polynucleotide is derived from a subject. In some cases, the original polynucleotide comprises genomic DNA. In some cases, the original polynucleotide comprises cell-free DNA, for example, cell-free DNA from a liquid biopsy sample (e.g., obtained from a subject). In some cases, cell-free DNA can comprise one or more DNA polynucleotides non-encapsulated DNA molecule(s) or fragment(s) thereof present in a sample. For example, an original polynucleotide comprising cell-free DNA can comprise a DNA polynucleotide or fragment thereof obtained from a sample (e.g., a liquid biopsy sample, such as a blood sample), wherein the DNA polynucleotide or fragment in the sample is not within a cell. In some cases, an original polynucleotide comprises a tumor DNA molecule or a fragment thereof (e.g., cell-free tumor DNA, such as circulating tumor DNA (ctDNA)). In some cases, an original polynucleotide is a genomic DNA molecule or fragment thereof obtained from (e.g., extracted from) a cell. In some cases, a method of determining a base in an original polynucleotide can be performed using starting material (e.g., original polynucleotide(s)) from a single cell.

In some cases, an original polynucleotide is from 10 basepairs (bp) to 10,000 bp in length. In some cases, an original polynucleotide is from 100 bp to 1,000 bp in length. In some cases, an original polynucleotide is 150 to 250 bp in length. In some cases, an original polynucleotide is greater than 10,000 bp in length. In some cases, a first polynucleotide is from 10 basepairs (bp) to 10,000 bp in length. In some cases, a first polynucleotide is from 100 bp to 1,000 bp in length. In some cases, a first polynucleotide is 150 to 250 bp in length. In some cases, an original polynucleotide is greater than 10,000 bp in length.

Herein are provided methods, systems, techniques, kits, compositions, and reagents that can be used to differentiate and identify an unmethylated base of a nucleotide, a methylated base of a nucleotide and a hydroxymethylated base of a nucleotide, for example, cytosine, 5mC, and 5hmC residues in a DNA strand. Methods herein can use sequencing. For example, methods can be performed on a double-stranded DNA polynucleotide. In some cases, methods can be performed on a single-stranded DNA polynucleotide. These residues can be identified using one or more methods provided herein, for example at single base pair resolution. A nucleotide, e.g., cytosine, and their or its modified forms can be chemically or enzymatically altered to appear different from one another as part of any method performed herein. In some embodiments, this can be performed on a first polynucleotide as well as a second polynucleotide (e.g., of a double-stranded DNA polynucleotide) to yield additional bits of information. In some such cases, the second polynucleotide can begin as having unmodified nucleic acid bases, e.g., cytosines, while the first polynucleotide can comprise modified nucleic acid bases, e.g., modified cytosines, e.g., as found in the sample to be analyzed. In some embodiments, a sequenced product (first polynucleotide, second polynucleotide, or both) can be decoded or deconvoluted to determine the methylation status of cytosine residues in the original polynucleotide (e.g., which can be the first polynucleotide). In some instances, the decoding can be binary. For example, when analyzing a double strand of DNA, the presence of two bases in proximity to each other on both strands that are read as thymine can indicate the presence of a cytosine in the original polynucleotide. In some instances, when analyzing a double strand of DNA, the presence of two bases in proximity to each other on both strands that are read as cytosine can indicate the presence of a cytosine in the original polynucleotide. In some instances, when analyzing a double strand of DNA, the presence of two bases in proximity to each other on both strands that are read as thymine can indicate the presence of a 5mC in the original polynucleotide. In some instances, when analyzing a double strand of DNA, the presence of two bases in proximity to each other on both strands that are read as cytosine can indicate the presence of a 5mC in the original polynucleotide. In some instances, when analyzing a double strand of DNA, the proximity of two bases to each other on both strands that are read as one cytosine and one thymine can indicate the presence of a 5hmC in the original polynucleotide.

Figure 1B:
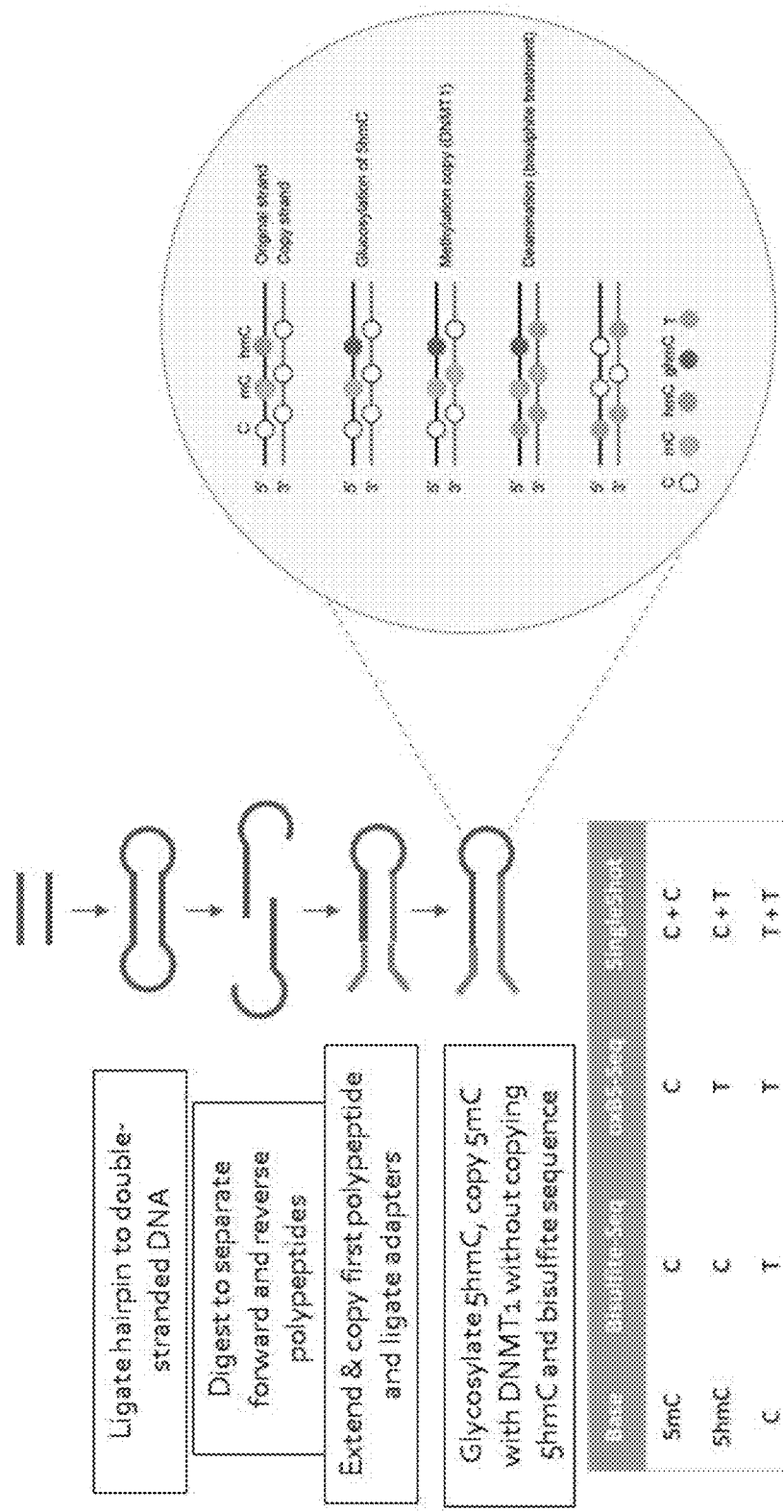

FIGS. 1A and 1B show examples of methods where cytosine, 5mC, and 5hmC can be modified (e.g., in the first polynucleotide, which can be the original polynucleotide) and sequenced to differentiate and identify the cytosine, 5mC, and 5hmC in the original polynucleotide. Such differentiation and identification can be at single base resolution. Such a method can begin by ligating one or more hairpins to double stranded DNA (e.g., comprising a first polynucleotide and a second polynucleotide), and de-annealing (e.g., melting) the first and second polynucleotides. In some cases, a molecule or moiety allowing subsequent ligation of a hairpin molecule can be ligated to the double-stranded DNA. Glucosylation of 5hmC on the first polynucleotide, for example by using beta-glucosyltransferase (BGT) and a uridinediphosphate glucose (UDPG), can be performed to glucosylate 5hmC on the first polynucleotide to yield 5-glucosylhydroxymethylcytosine (5ghmC or ghmC). Such glucosylation can protect the 5hmC from some chemical activity of other agents, such as those used in a method or system disclosed herein. In some cases, a methyltransferase (e.g., DNA (cytosine-5)-methyltransferase 1 (DNMT1) or DNMT5) can be used to methylate, for example cytosine bases, on the second polynucleotide where the methylation is at least in part directed by methylated bases, for example mC, on the first polynucleotide. Many methyltransferases (including DNTM1 and DNMT5) act on a second base (e.g., a cytosine) of the second polynucleotide of a double-stranded DNA polynucleotide proximal to (e.g., adjacent to) a first base corresponding to (e.g., base-paired with) a methylated cytosine (e.g., 5-methylcytosine (5mC) or 5-hydroxymethylcytosine (5hmC)). In some cases, the first base and the second base are said to be in a CpG context, for example, because the first base (e.g., a methylated cytosine, for instance, 5mC or 5hmC) of the first polynucleotide is adjacent to a guanine of the first polynucleotide (e.g., cytosine-phosphate-guanine), which is basepaired with the (e.g., unmethylated) cytosine on the second polynucleotide (e.g., which the methyltransferase or biologically active fragment thereof can modify to have a 5-methyl- or 5-hydroxymethyl-tag matching that of the first base). It is noted that unmethylated and methylated cytosine bases (and associated thymine, ghmC, formylcytosine (fC), and dhU base modifications) depicted in FIGS. 1A-1B, 2A-2D, 3, 4, 6, 9, 12, 17, 19C, and 19E on the first polynucleotide (e.g., labeled with the 5' end) can be proximal to (e.g., in a CpG context with) corresponding bases depicted on the second polynucleotide in those figures. Basepaired guanines in various images depicting CpG relationships have been omitted in some cases in order to improve visual clarity and ease of interpretation of the figures. Some methods and systems presented herein comprise exposing the first polynucleotide and/or the second polynucleotide to a deamination agent. Deamination (e.g., by treatment with bisulfite or deaminase enzymes) can be performed to yield a deaminated base, for example uracil, in place of non-methylated cytosine residues in the first polynucleotide and the second polynucleotide, and both strands can be sequenced. The deaminated base can be read as a deaminated base in a sequencer. In some embodiments, uracil can be read as a thymine by a sequencer. Where the first polynucleotide before processing contains a non-methylated cytosine residue (e.g., in the context of a CpG moiety), two thymine residues in physical proximity on the two separate strands can be read during sequencing. Where the first polynucleotide before processing contains a 5mC residue, two cytosine residues can be read in physical proximity on the two separate strands during sequencing. Where the first polynucleotide before sequencing contains a 5hmC residue, a cytosine (e.g., on the first polynucleotide) and thymine (second polynucleotide) can be read during sequencing. Methods can produce results that can be superior to methods comprising bisulfite-sequencing or oxidative bisulfite (ox-BS) sequencing. Methods useful in performing oxidative bisulfite (ox-BS) sequencing and analysis of data produced by oxidative bisulfite sequencing are described in international patent publication number WO2013017853. An agent capable of oxidizing a methylated cytosine (e.g., 5-hydroxymethylcytosine), such as a ruthenate (e.g., potassium ruthenate), can be used as an oxidizing agent in a method comprising oxidative bisulfite sequencing.

In some cases, one or more sequencing adapter is coupled to (e.g., ligated to) one or more ends (e.g., a 5' end and/or a 3' end) of a double-stranded DNA molecule after chemical processing operations (e.g., contacting with an entity having methyltransferase activity, contacting with an oxidizing agent, contacting with a reducing agent, contacting with bisulfite, contacting with a deamination agent), for example, as shown in FIG. 1B. In some cases, one or more sequencing adapter is coupled to (e.g., ligated to) one or more ends (e.g., a 5' end and/or a 3' end) of a double-stranded DNA molecule before chemical processing operations (e.g., contacting with an entity having methyltransferase activity, contacting with an oxidizing agent, contacting with a reducing agent, contacting with bisulfite, contacting with a deamination agent), for example, as shown in FIG. 1B. It is contemplated that coupling of one or more sequencing adapters to one or more of the first and/or second polynucleotide of a double-stranded DNA polynucleotide can be performed, in some cases, between operations of a method presented herein.

Figure 2A:
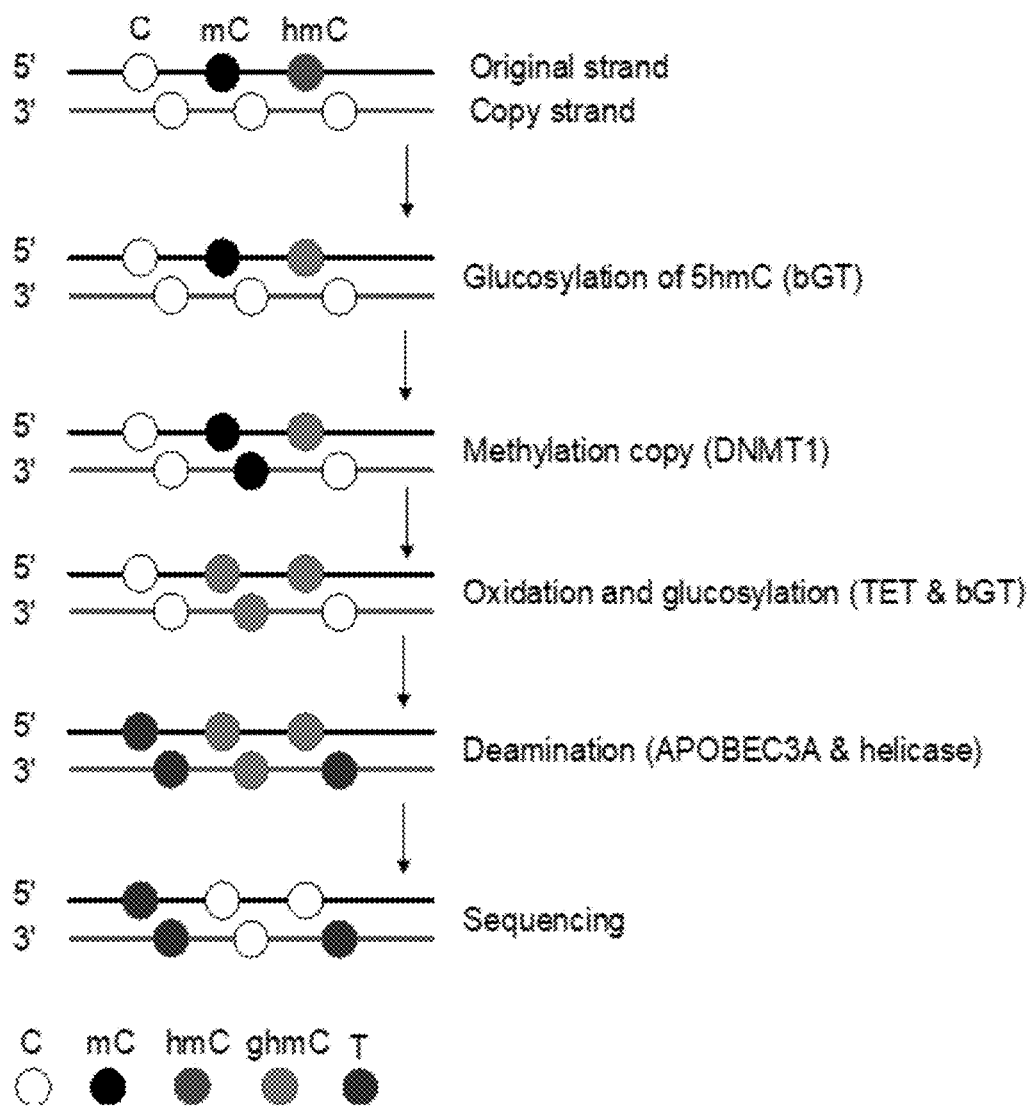
FIGS. 2A, 2B, 2C, and 2D depict a method for differentiating and identifying cytosine, mC, and hmC in a DNA sequence, in accordance with embodiments. In various aspects, the method can employ, for example, glucosylation, methylation, oxidation, deamination, treatment with a reducing agent, treatment with methyltransferase (MT), and/or treatment with an S-adenosylmethionine (SAM) analogue.

FIGS. 2A-2D depict methods where cytosine, 5mC, and 5hmC can be modified and sequenced to differentiate and identify the cytosine, 5mC, and 5hmC in the first polynucleotide. Such differentiation and identification can be at single base resolution. In various embodiments, bisulfite treatment is not necessary. In some embodiments, this lack of bisulfite can protect the DNA to be sequenced from degradation or damage. In FIG. 2A, glucosylation of 5hmC on the first polynucleotide, for example by using BGT and UDPG can be performed to glucosylate 5hmC on the first polynucleotide to yield 5-glucosylhydroxymethylcytosine (5ghmC or ghmC). Such glucosylation can protect the 5hmC from some chemical transformations. In some cases, DNMT1 can be used to methylate, for example cytosine bases, on the second polynucleotide where the methylation is at least in part directed by methylated bases, for example mC, on the first polynucleotide. In some embodiments, uracil can be read as a thymine by a sequencer. Oxidation and glucosylation can then be performed (e.g., using a ten-eleven translocation methylcytosine dioxygenase enzyme (TET) and BGT, respectively) to convert 5mC to 5ghmC. Deamination of cytosine to yield thymine can be performed, for example by using Apolipoprotein B mRNA editing enzyme, catalytic polypeptide-like (APOBEC—such as, for example, APOBEC 3A) and helicase, or fragments thereof, and both strands can be sequenced. The resulting sequencing data can be decoded to determine which bases are cytosine, 5mC and 5 hmC. In some embodiments, another reagent can be used to yield single stranded DNA in lieu of or in addition to the helicase. Examples of such reagents can comprise, for example, formamide or sodium hydroxide (NaOH). Where the first polynucleotide before processing contains a non-methylated cytosine residue, two thymine residues in physical proximity on the first and second polynucleotides can be read during sequencing, e.g., in a CpG context. Where the first polynucleotide before processing contains a 5mC residue, two cytosine residues in physical proximity on the two strands (e.g., the first and second polynucleotides) can be read during sequencing, e.g., in a CpG context. Where the first polynucleotide before sequencing contains a 5hmC residue, a cytosine (first polynucleotide) and thymine (second polynucleotide) in physical proximity on the two strands (e.g., the first and second polynucleotides) can be read during sequencing, e.g., in a CpG context. Methods can produce results that can be superior to methods comprising bisulfite-sequencing or ox-BS sequencing.

Figure 2B:
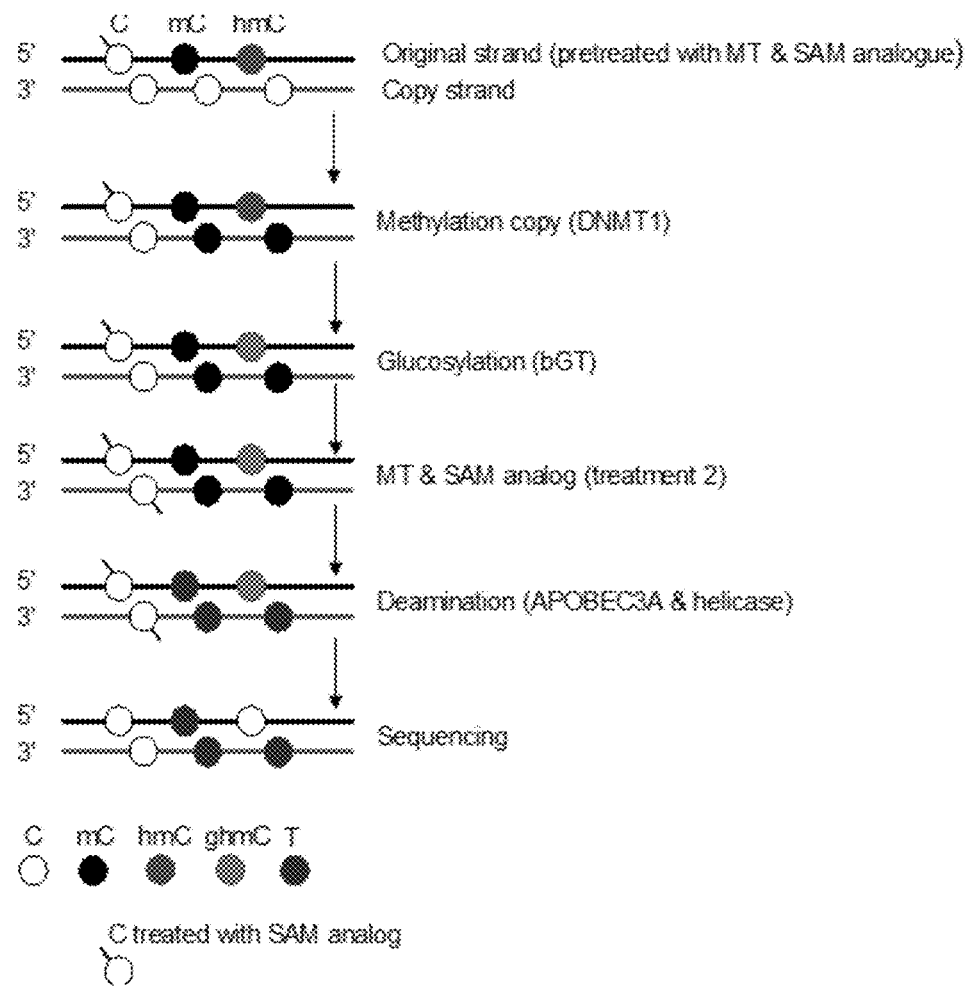

In FIG. 2B, the first polynucleotide can be pretreated with a methyltransferase (MT) and an S-adenosyl methionine (SAM) analogue to yield a cytosine having an appended methyl derivative group in place of a non-methylated cytosine. In some cases, DNMT1 can be used to methylate, for example cytosine bases, on the second polynucleotide where the methylation is at least in part directed by methylated bases, for example 5mC, on the first polynucleotide. In some embodiments, uracil can be read as a thymine by a sequencer. Glucosylation of 5hmC on the first polynucleotide, for example by using BGT and UDPG, can be performed to glucosylate 5hmC on the first polynucleotide to yield 5-glucosylhydroxymethylcytosine (5ghmC or ghmC). Such glucosylation can protect the 5hmC from some chemical transformations, such as methyltransferase (e.g., DNMT1 or DNMT5) activity. The first polynucleotide and second polynucleotide can be then treated with a MT and a SAM analogue to again yield a cytosine having an appended SAM analogue in place of non-methylated cytosine. Deamination of a nucleic acid base, e.g., cytosine can be performed, for example by using APOBEC3A or a fragment or mutant thereof and separating at least a portion of the first and second polynucleotides, for example using a helicase (which can be used, e.g., to separate the first and second polynucleotide strands for APOBEC3A-mediated deamination), a single-strand DNA-binding protein (SSB). In some cases, a double-strand deaminase (e.g., DddA, see, for example, Mok, B. Y., de Moraes, M. H., Zeng, J. et al. A bacterial cytidine deaminase toxin enables CRISPR-free mitochondrial base editing. *Nature* 583, 631-637 (2020), which is incorporated herein by reference in its entirety) can be used, which may not require that the first and second polynucleotides be separated, and the first and second polynucleotides can be sequenced. In some cases, separating a first and second polynucleotide of a double-stranded DNA polynucleotide can comprise contacting the double-stranded DNA polynucleotide with an intercalating agent (e.g., ethidium bromide), for example to lower the melting temperature of the double-stranded DNA polynucleotide. In some cases, separating the first and second polynucleotides of a double-stranded DNA polynucleotide can be comprise chemically treating the first and/or second polynucleotides (e.g., with NaOH). Such methods of aiding in the separation of the first polynucleotide from the second polynucleotide are especially useful in cases where Watson-Crick mismatches between paired bases of the double-stranded polynucleotide are not expected (e.g., in some instances of 4-letter sequencing using two-base sequencing analysis, as presented herein). The deaminated cytosine can be read as a thymine using a sequencer. Where the first polynucleotide before processing contains a non-methylated cytosine residue, two cytosine residues can be read in physical proximity on the two separate strands (e.g., the first and second polynucleotides) during sequencing, e.g., in a CpG context. Where the first polynucleotide before processing contains a 5mC residue, two thymine residues in physical proximity on the two separate strands can be read in physical proximity on the two separate strands during sequencing, e.g., in a CpG context. Where the first polynucleotide before sequencing contains a 5hmC residue, a cytosine (first polynucleotide) and thymine (second polynucleotide, e.g., cognate polynucleotide) can be read during sequencing, e.g., in a CpG context. Methods can produce results that can be superior to methods comprising bisulfite-sequencing or ox-BS sequencing.

A first polynucleotide and second polynucleotide of a double-stranded DNA polynucleotide (e.g., as shown in FIGS. 1A-12, and 17-19E) can be linked (e.g., to one another). In some cases, a first polynucleotide of a double-stranded DNA polynucleotide and a second polynucleotide of a double-stranded DNA polynucleotide are linked via a hairpin (e.g., a hairpin polynucleotide). In some cases, a first polynucleotide of a double-stranded DNA polynucleotide and a second polynucleotide of a double-stranded DNA polynucleotide are linked via Watson-Crick base pairing (e.g., nucleic acid hybridization). In some cases, a first polynucleotide of a double-stranded DNA polynucleotide and a second polynucleotide of a double-stranded DNA polynucleotide are linked via information associated with the first and/or second polynucleotide (e.g., in the form of one or more barcodes (e.g., unique barcodes or UMIs) ligated or bound to one or more end of the first polynucleotide, the second polynucleotide, or both). In some cases, a first polynucleotide of a double-stranded DNA polynucleotide and a second polynucleotide of a double-stranded DNA polynucleotide are linked via a combination of other methods for linking the first and second polynucleotides. It is noted that, while FIGS. 1A-12, and 17-19E, may depict one example of linking a first and second polynucleotide of a double-stranded polynucleotide for a given embodiment or set of embodiments of the methods, systems, and compositions disclosed herein, linking the first and second polynucleotide can be achieved via any of the examples presented herein for each embodiment. For instance, while hairpin polynucleotides are not shown in FIG. 2A-2D, 3, or 4, first and second polynucleotides used in the methods and systems and compositions depicted in those figures may be linked via hairpin polynucleotide(s).

Figure 3:
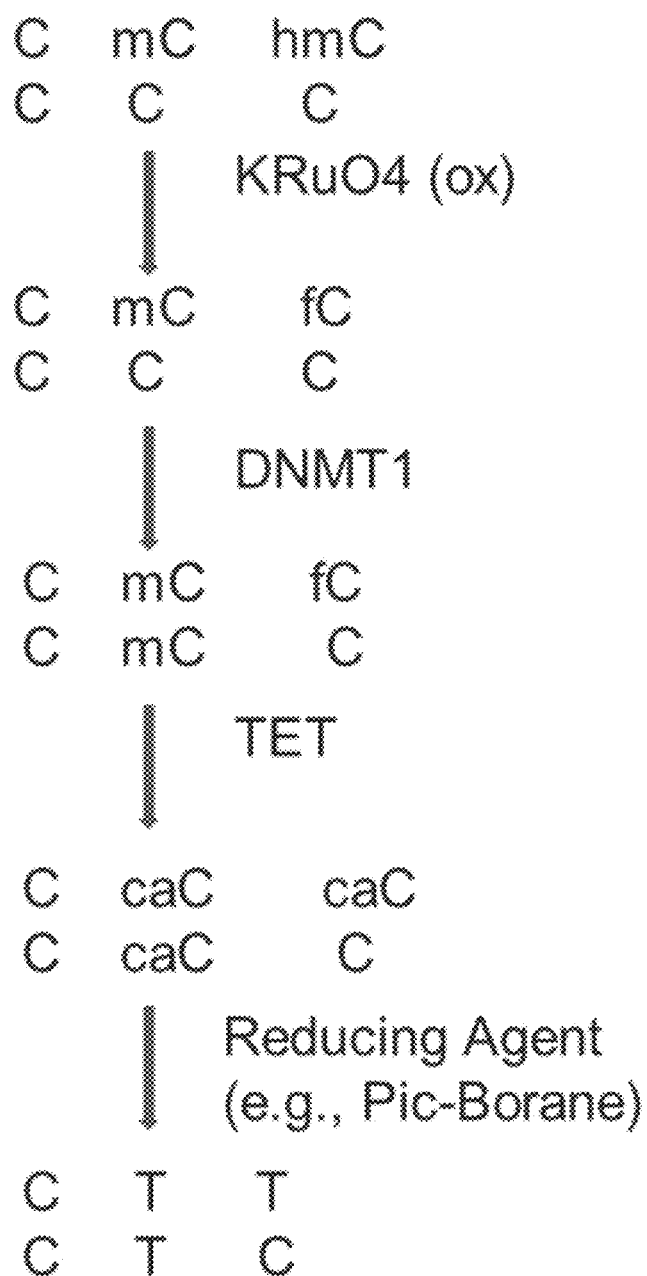
FIG. 3 depicts a method for differentiating and identifying cytosine, mC, and hmC in a DNA sequence, in accordance with embodiments. In various aspects, the method can employ, for example, oxidation (e.g., KRuO$_4$ oxidation), methylation, enzymatic modification, e.g., using an oxidase (e.g., a TET enzyme) or a fragment thereof, and a reducing moiety, for example a borane, (e.g., picoline borane, pic-borane, 2-picoline-borane, pic-BH$_3$).

FIG. 3 depicts an additional method where cytosine, 5mC, and 5hmC can be modified and sequenced to differentiate and identify the cytosine, 5mC, and 5hmC in the first polynucleotide, depicted in FIG. 3. Such differentiation and identification can be at single base resolution. $KRuO_4$ can be used to oxidize a hydroxymethylated nucleic acid base, e.g., 5hmC, in the first polynucleotide to yield a formyl nucleic acid base, e.g., 5-formylcytosine (5fC or fC). In some cases, DNMT1 can be used to methylate, for example cytosine bases, on the second polynucleotide where the methylation is at least in part directed by methylated bases, for example mC, on the first polynucleotide. Oxidation can then be performed (e.g., using an oxidase or a biologically active portion thereof, such as TET) to convert 5mC to 5-carboxylcytosine (5caC or caC). It is noted that operations of methods and systems presented herein comprising oxidation of all or a portion of a polynucleotide (e.g., a first polynucleotide, a second polynucleotide, or double-stranded DNA polynucleotide) can employ an oxidase that oxidizes 5-methylcytosine, 5-hydroxymethylcytosine, and/or 5-formylcytosine, though, TET is often used herein as an example oxidizing agent. Pic-borane can then be used to convert 5caC to DHU residues for sequencing, and both strands can be sequenced (e.g., wherein DHU is read as a thymine). Where the first polynucleotide before processing contains a non-methylated cytosine residue, two cytosine residues can be read in physical proximity on the two separate strands (e.g., the first and second polynucleotides) during sequencing, e.g., in a CpG context. Where the original strand before processing contains a 5mC residue, two thymine residues can be read in physical proximity on the two separate strands during sequencing, e.g., in a CpG context. Where the original strand before sequencing contains a 5hmC residue, a thymine (first polynucleotide) and cytosine (second polynucleotide) can be determined in physical proximity on the individual strands (e.g., the first polynucleotide and/or the second polynucleotide) during sequencing, e.g., in CpG context. Methods can produce results that can be superior to methods comprising bisulfite-sequencing or ox-BS sequencing.

In some embodiments, a different reagent can be used, for example to convert 5caC to a thymine residue. Such a different reagent can be used, for example, in lieu of pic-borane. In some embodiments, the different reagent can be a borane, a derivative of borane, or a derivative or precursor of pic-borane. In some embodiments, the different reagent can comprise a structural or chemical similarity to pic-borane. In some embodiments, for example, such a reagent (e.g., reducing agent) can comprise pyridine borane, 2-picoline borane (pic-$BH_3$ or pic-borane), borane, tert-butylamine borane, ammonia borane, sodium borohydride, ethylenediamine borane, dimethylamine borane, sodium triacetoxyborohydride, morpholine borane, 4-methylmorpholine borane, trimethylamine borane, dicyclohexylamine borane, or a salt thereof. In some embodiments, conversion of 5caC to thymine can be performed, for example, as provided in WO2019/13613 A1, which is incorporated by reference herein in its entirety. In some embodiments, a reagent used in such a reducing operation can comprise a different reducing agent, either in combination with or in lieu of a reducing agent provided above. A reducing agent may comprise sodium borohydride (NaBH$_4$), sodium cyanoborohydride (NaBH$_3$CN), NaCNBEE, or lithium borohydride (LiBH$_4$). A reducing agent may comprise lithium aluminum hydride, sodium amalgam, amalgam, diborane, sodium borohydride, sulfur dioxide, dithionate, thiosulfate, iodide, hydrogen peroxide, hydrazine, diisobutylaluminum hydride, oxalic acid, carbon monoxide, cyanide, ascorbic acid, formic acid, dithiothreitol, beta-mercaptoethanol, or any combination thereof. A reducing agent may selectively reduce, or improve the selective reduction of, 5caC to a thymine residue.

In some embodiments, caC (e.g., 5caC) can be reduced, for example to uracil (U) or dihydrouracil (DHU) in a method provided herein. This can, for example, be performed in lieu of conversion of caC to a thymine residue in a method provided herein. In some such embodiments, this can be performed, for example, as described in (Schuler P, Miller Ak. Sequencing the sixth base (5-hydroxymethylcytosine): selective DNA oxidation enables base-pair resolution. Angew Chem Int Ed Engl. 2012; 51(43):10704-10707. doi:10.1002/anie.201204768), which is incorporated by reference herein in its entirety.

Figure 4:
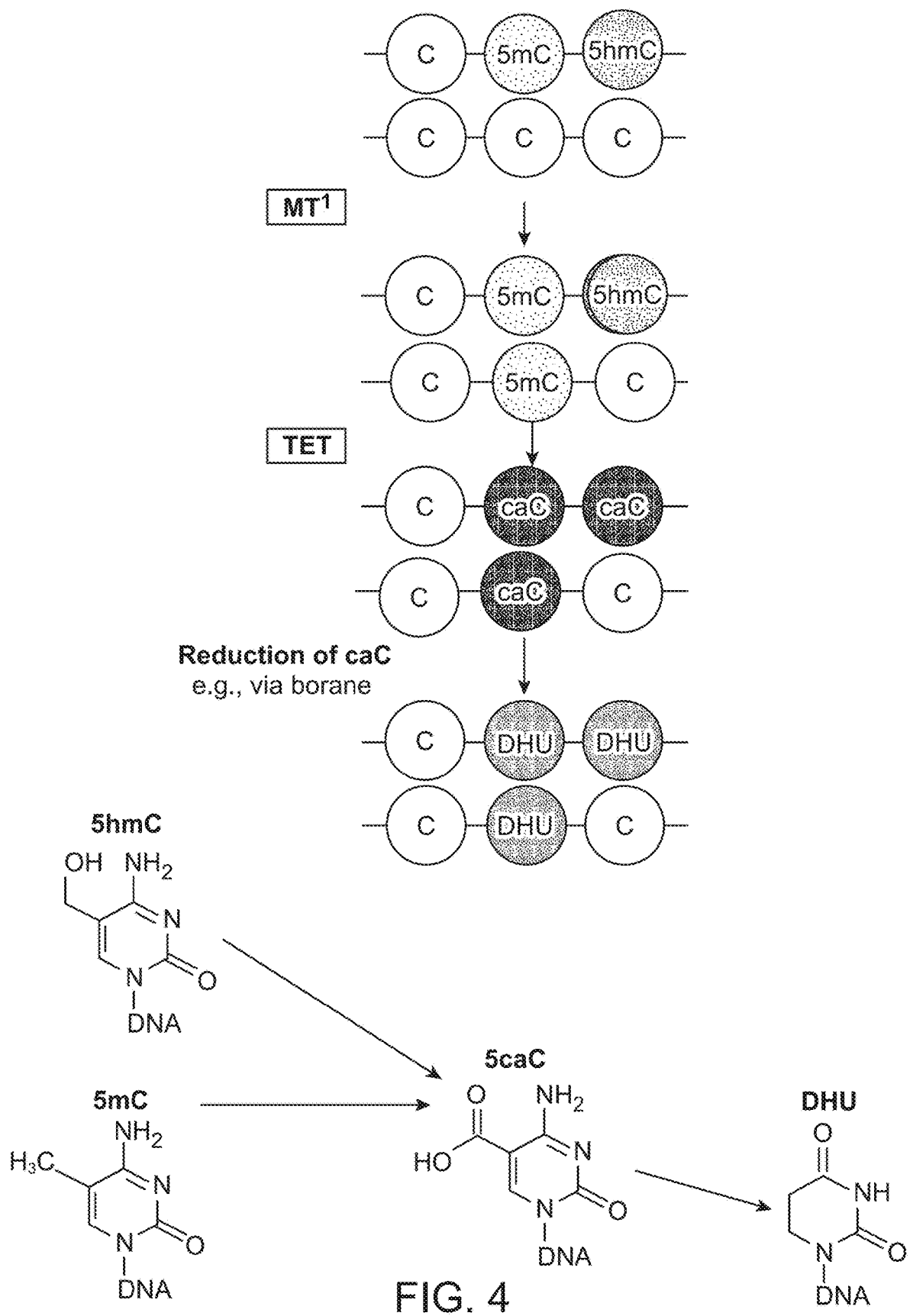
FIG. 4 depicts a method for differentiating and identifying cytosine, mC, and hmC in a DNA sequence, in accordance with embodiments. In various aspects, the method can employ, for example, methylation, enzymatic modification, e.g., using an oxidase (e.g., a TET enzyme) or a fragment thereof, and a reducing moiety, for example a borane, (e.g., picoline borane, pic-borane, 2-picoline-borane, pic-BH$_3$).

In some embodiments of the two-base sequencing method, the first polynucleotide (and/or second polynucleotide) is not contacted with beta-glucotransferase (bGT), for example, prior to contacting the first polynucleotide and the second polynucleotide with an agent having DNA methyltransferase activity. For example, a two-base sequencing method capable of distinguishing six nucleic acid bases (e.g., 6-letter sequencing, wherein adenine, guanine, thymine, cytosine, 5-methylcytosine, and 5-hydroxymethylcytosine can all be distinguished from one another) may not, in some cases, comprise contacting the first polynucleotide (and/or the second polynucleotide) with bGT (e.g., as shown in FIG. 4). In some cases, a first polynucleotide and second polynucleotide are contacted with a molecule having DNA methyltransferase activity with sufficient specificity to transfer methylation tags from a 5-methylcytosine base on the first polynucleotide to a cytosine on the second polynucleotide (e.g., a cytosine on the second polynucleotide proximal to (e.g., adjacent to) a locus corresponding to that of the 5-methylcytosine on the first polynucleotide). For example, DNA methyltransferase-5 (DNMT5) or DNMT1 may be used to contact a first polynucleotide comprising a 5-methylcytosine base and/or a 5-hydroxymethylcytosine (5hmC) base (e.g. wherein the first polynucleotide is linked, for example, via Watson-Crick basepairing and/or via a hairpin polynucleotide), for example, in order to transfer a 5-methylcytosine (5mC) tag to a cytosine of the second polynucleotide, where the 5mC and the cytosine are in a CpG context. In some cases, an unprotected 5hmC base on the same first polynucleotide will not transfer to a cytosine on the second polynucleotide (e.g., even if there exists an unmarked cytosine on the second polynucleotide in a CpG context with (e.g., proximal to) the 5hmC on the first polynucleotide) when contacted with the DNMT5 or DNMT1, for example, because of the base-specificity of the DNMT1 or DNMT5 methyltransferase activity. In some cases, a methyltransferase may not be specific to transfer methylation tags from a 5-methylcytosine base on the first polynucleotide to a cytosine on a (e.g., linked) second polynucleotide (e.g., a cytosine on the second polynucleotide proximal to (e.g., adjacent to) a locus corresponding to that of the 5-methylcytosine on the first polynucleotide) and 5-hydroxymethylcytosine may be protected from non-specific methyltransferase activity through modification, for example, through (e.g., enzymatic) glycosylation. After contacting the first and second polynucleotides with the DNA methyltransferase, the first and second polynucleotides can be contacted with an oxidizing agent (e.g., a TET, TET derivative, or biologically active fragment thereof), for example, to convert 5mC and 5hmC bases present on the first polynucleotide and/or the first and second polynucleotides into 5-carboxylcytosine (e.g., "5caC" or "caC" as shown in FIG. 4). The first and second polynucleotides can be contacted with a reducing agent (e.g., a reducing agent presented herein, such as borane), for example, to convert caC bases to DHU residues. After contact with the reducing agent, the first and/or second polynucleotide can be treated with a mild base or, in some cases, a mild acid. In some cases, the first and second polynucleotides are separated (e.g., by using a helicase, a single-stranded DNA binding protein, a strand-displacing polymerase, or an increase in temperature) before a read polynucleotide is generated as described herein (e.g., using PCR). As described herein, the first polynucleotide and the read polynucleotide can be sequenced, and a value of a true base on an original polynucleotide (which is, in some cases, the first polynucleotide) can be determined using two-base sequencing, as presented herein. For example, a value of a true base on an original polynucleotide (which can be the first polynucleotide) can be determined based on the identity of a first base of the first polynucleotide and second base of the second polynucleotide, e.g., wherein the second base is paired with the first base (e.g., Watson-Crick basepaired, as in cases where the value of the true base is determined to be adenine, guanine, or thymine) or wherein the second base is proximal to (e.g., in a CpG context with; as in cases where the value of the true base is determined to be 5mC or 5hmC).

Figure 5:
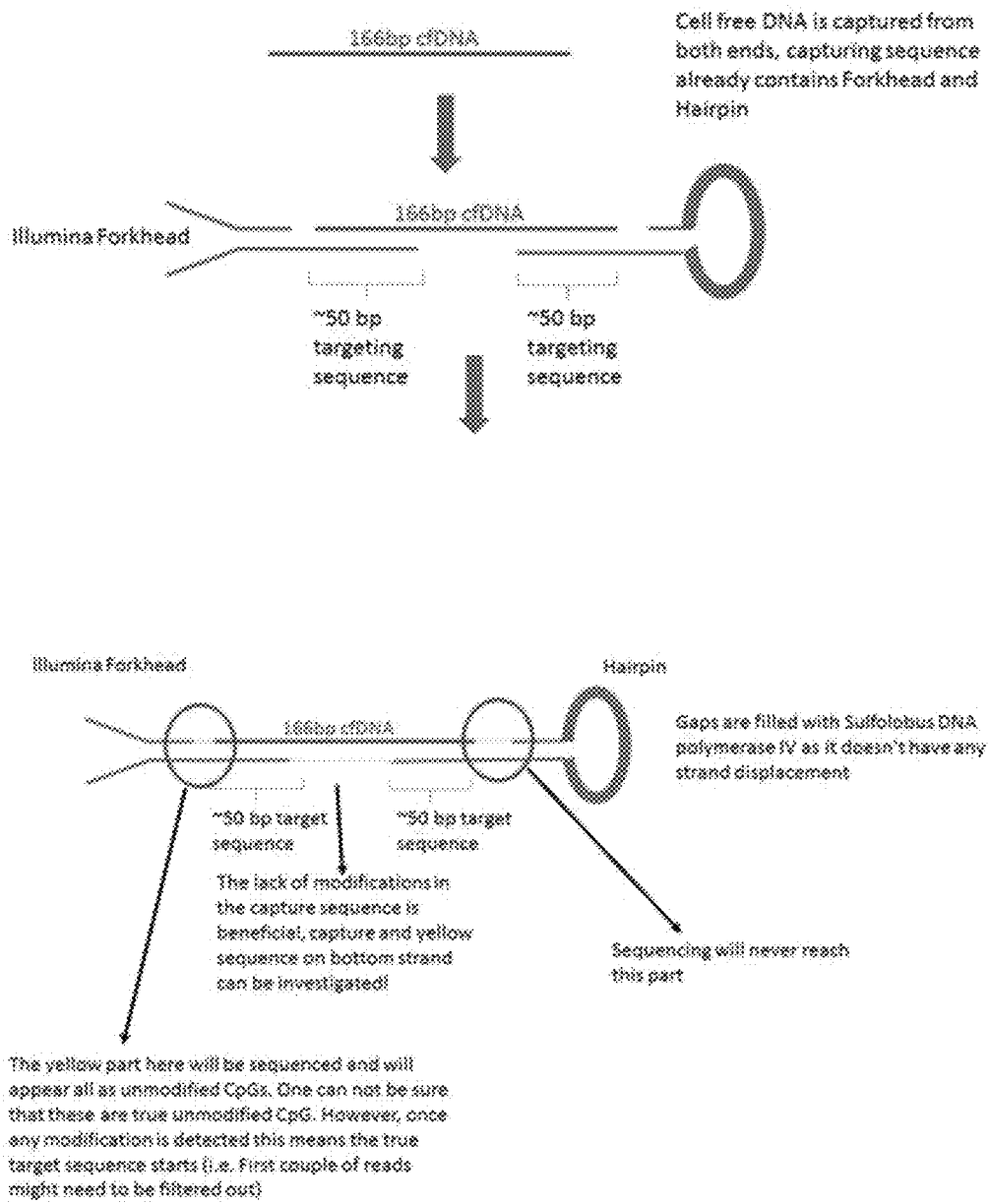
FIG. 5 depicts, among other things, a method for preparing a DNA sequence for sequencing, in accordance with embodiments.
Figure 7A:
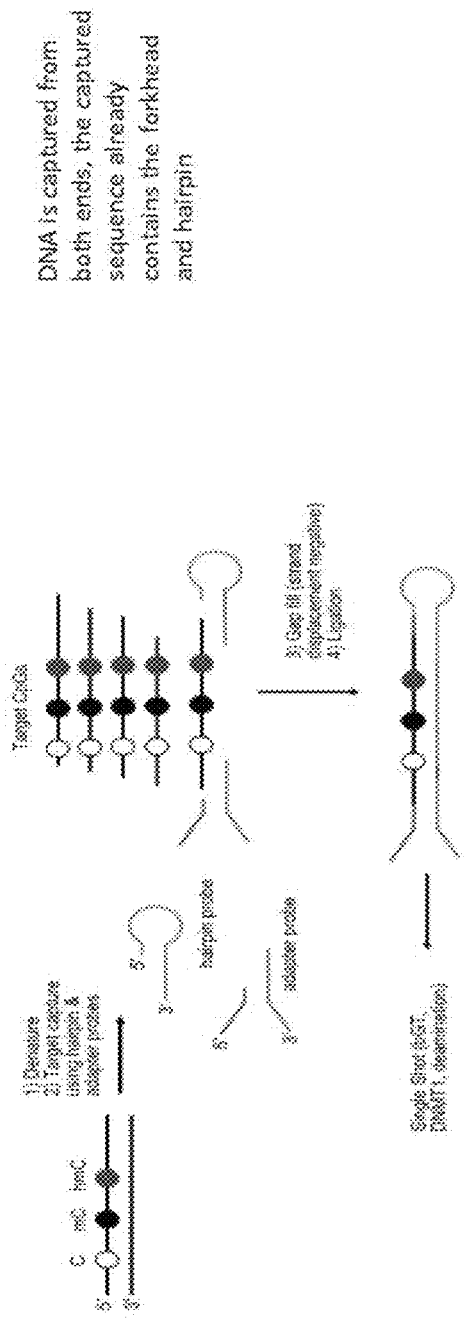
FIG. 7A depicts, among other things, targeted capture and subsequent processing of a polynucleotide comprising cytosine (white circle), 5-methylcytosine (black circle), or 5-hydroxymethylcytosine (red circle) that is compatible with two-base sequencing analysis and 6-letter sequencing analysis, in accordance with embodiments.

FIGS. 5 and 7A depict methods that can be applied to sequence DNA in methods provided herein. Cell-free DNA (cfDNA) or fragmented DNA can be captured from both ends, yielding a sequence that already contains a forkhead and hairpin. This DNA can comprise one or more (e.g., two) targeting sequences. In some cases, the capture DNA (e.g., comprising a hairpin and a targeting sequence) can comprise one targeting sequence. In some cases, the capture DNA comprises two targeting sequences. In some cases, a targeting sequence can be from 10 to 200 bp in length. In some cases, a targeting sequence can be from 20 to 100 bp in length. In some cases, a targeting sequence can be 25 to 50 bp in length. For example, the DNA can comprise two targeting sequences of approximately 50 base pair (bp) in length (e.g., where the captured cfDNA can comprise about 166 base pairs). In some cases, the cfDNA may comprise more than 166 base pairs or less than 166 base pairs. Gaps can optionally be filled with sulfolobus DNA polymerase IV. In some embodiment, any method of non-strand displacement can be used in lieu of or in addition to sulfolobus DNA polymerase IV. In some cases, such a process does not result in strand displacement. A lack of modifications in a copied sequence can be beneficial, and the new sequence on the bottom strand can be investigated. In some cases, a section near the forkhead can be sequenced, and can appear as unmodified CpGs. These may or may not be true unmodified CpGs. In some cases, once modification is detected, confirmation of a true target sequence can be confirmed. As illustrated by FIG. 7A, a method can comprise providing a first polynucleotide, (e.g., wherein the first polynucleotide comprises cytosine, mC, and/or hmC), separating the first polynucleotide from its complement strand, capturing target first polynucleotides using a hairpin polynucleotide (e.g., hairpin probe) and an adapter polynucleotide (e.g., an adapter probe, which can comprise a sequencing adapter), gap filling the first polynucleotide to the hairpin and adapters before ligating, and performing 4-, 5-, or 6-letter sequencing as presented herein (e.g., comprising contacting the first and/or second strands with bGT, DNMT1, and a deamination agent).

Figure 6:
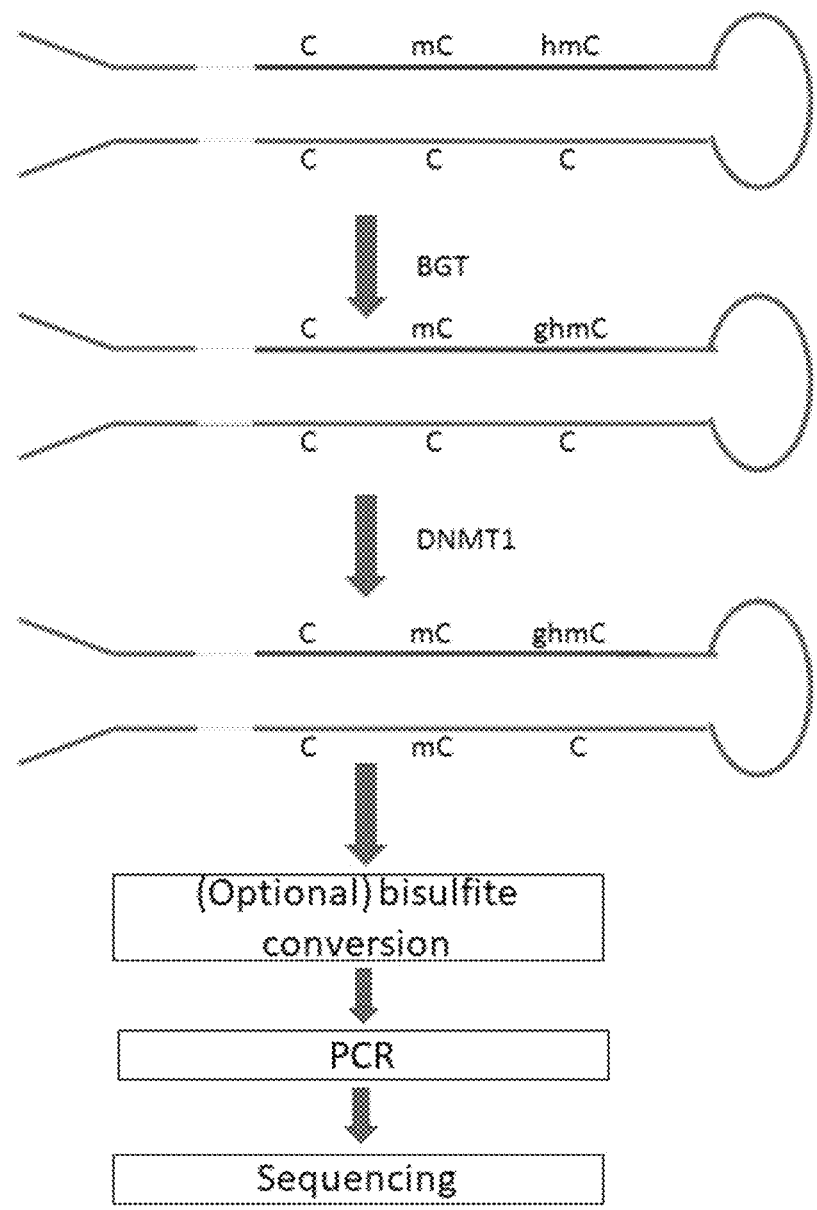
FIG. 6 depicts, among other things, a method comprising targeted capture and subsequent processing of a polynucleotide comprising cytosine, mC, or hmC, in accordance with embodiments.

FIG. 6 depicts a method where a sequence can be modified using BGT and DNMT1 and subjected to BS conversion/PCR and sequencing. In some embodiments, such a method can be a continuation of a method such as that provided in FIG. 5. Such a method can feature no blunt end ligation or digest with a mixture of enzymes that generate a single nucleotide gap where a uracil or deoxyuracil was present, such as, for example, a mixture of Uracil DNA Glycosylase (UDG) and Endonuclease VIII, which can reduce or eliminate contributors to low yield. In some embodiments, such a method can yield efficient sticky end ligation; for example, hybridization and elongation can be performed at or around 55 degrees C. In some embodiments, hybridization and elongation can be performed at about 40 degrees C., about 45 degrees C., about 50 degrees C., about 55 degrees C., about 60 degrees C., about 65 degrees C., about 70 degrees C., or a range between any two foregoing values. In some embodiments, long to very long capture sequences can reduce or eliminate off-target capture. In some embodiments, targeting can be performed on native DNA (e.g., having a 4 base code such as C, G, A, T). In some embodiments, a flexible targeting sequence can allow capture of cfDNA with variable linker length. In some embodiments, such a method can display: less efficient capture of sonicated DNA compared with cfDNA, for example due to more random fragments in sonicated DNA. In some embodiments, BS conversion may result in material loss which may affect yield for cfDNA; In some embodiments, carrier DNA can be used to protect from such material loss. In some embodiments, cfDNA may not have a punctate pattern (e.g., nucleosomal), which may be associated with loss of material when capturing using a single probe; In some embodiments, probe tiling can be used to protect from such material loss.

Figure 7B:
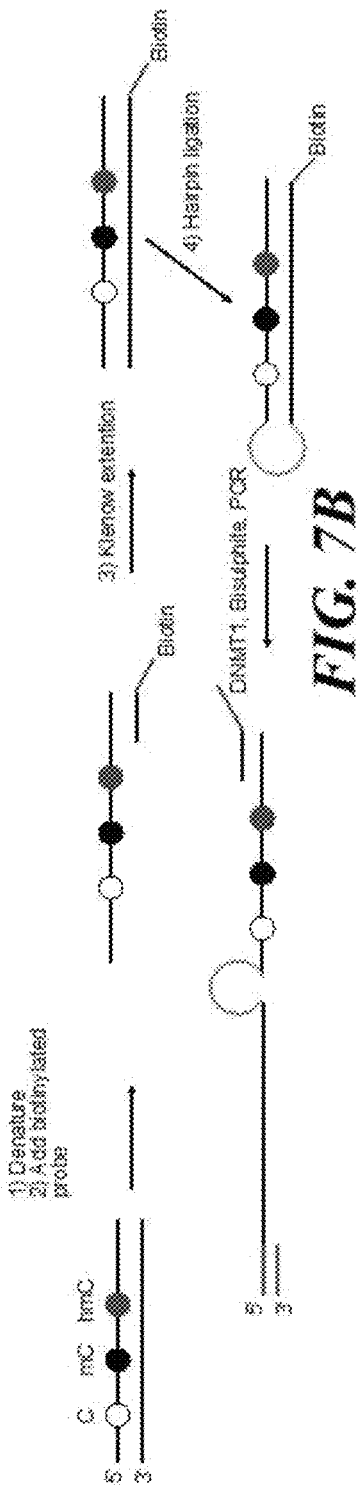
FIG. 7B depicts, among other things, a method for using a biotinylated probe with a type Is restriction site, in accordance with embodiments.

FIG. 7B depicts a method for targeted sequencing. Such a method can feature single capture. In some embodiments, a method can be applied to cfDNA and other fragmented DNA, for example sonicated DNA. In some embodiments a unique molecular identifier (UMI) can be incorporated in the probes, for example for deduplication. In some embodiments, biotinylated probes/strep beads can be used for cleanup, and can result in less background than without such probes or beads. Such a method can be simple and quick, and in some cases can yield a single day workflow. In some embodiments, such a method can display: single-end T/A ligation. 3-base P5-specific PCR primers may be used, and such a method can use 2 sets of primers or longer oligonucleotides than a method used for 4-letter base discrimination (e.g., 4-letter sequencing).

Figure 8:
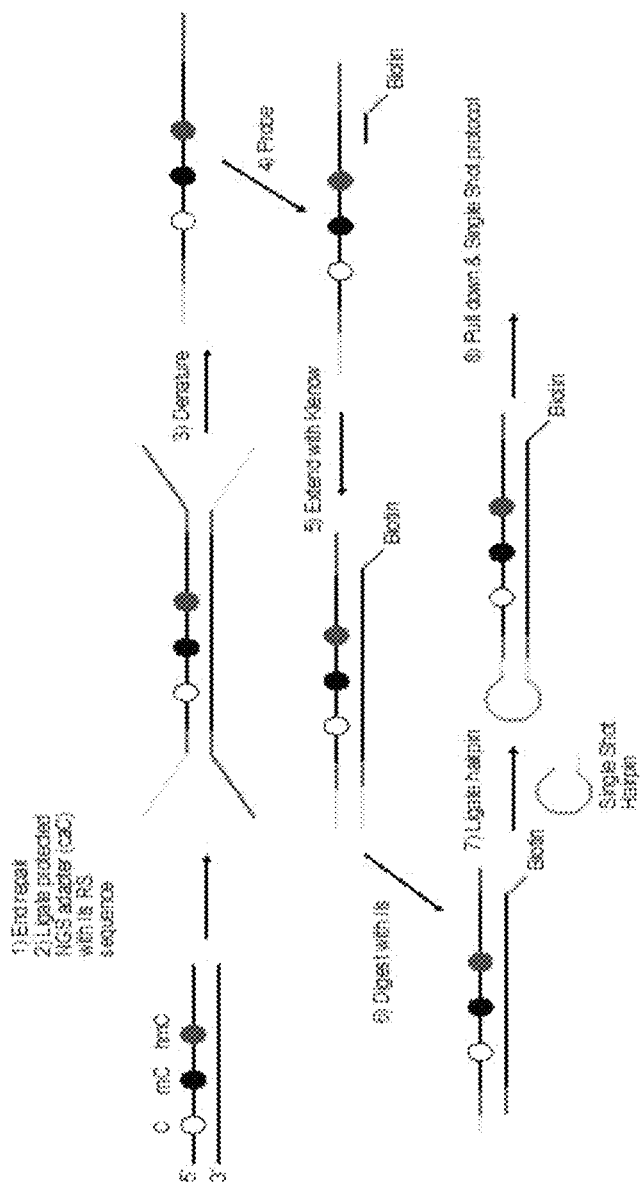
FIG. 8 depicts, among other things, a modified method for differentiating or identifying cytosine, mC, and hmC in a DNA sequence using a biotinylated probe, in accordance with embodiments.

FIG. 8 depicts a method of using a biotinylated probe with a type Us restriction site (some can be rare and can be used, for example in synthetic biology methods). Such a method can be compatible with a general type II restriction enzyme. In some cases, such a method can eliminate any probe annealing to converted DNA. Initial adapters can be ligated by TA cloning or other ligation methods, but hairpin adapter ligation can be an efficient 4-base overhang and ligation.

Figure 9:
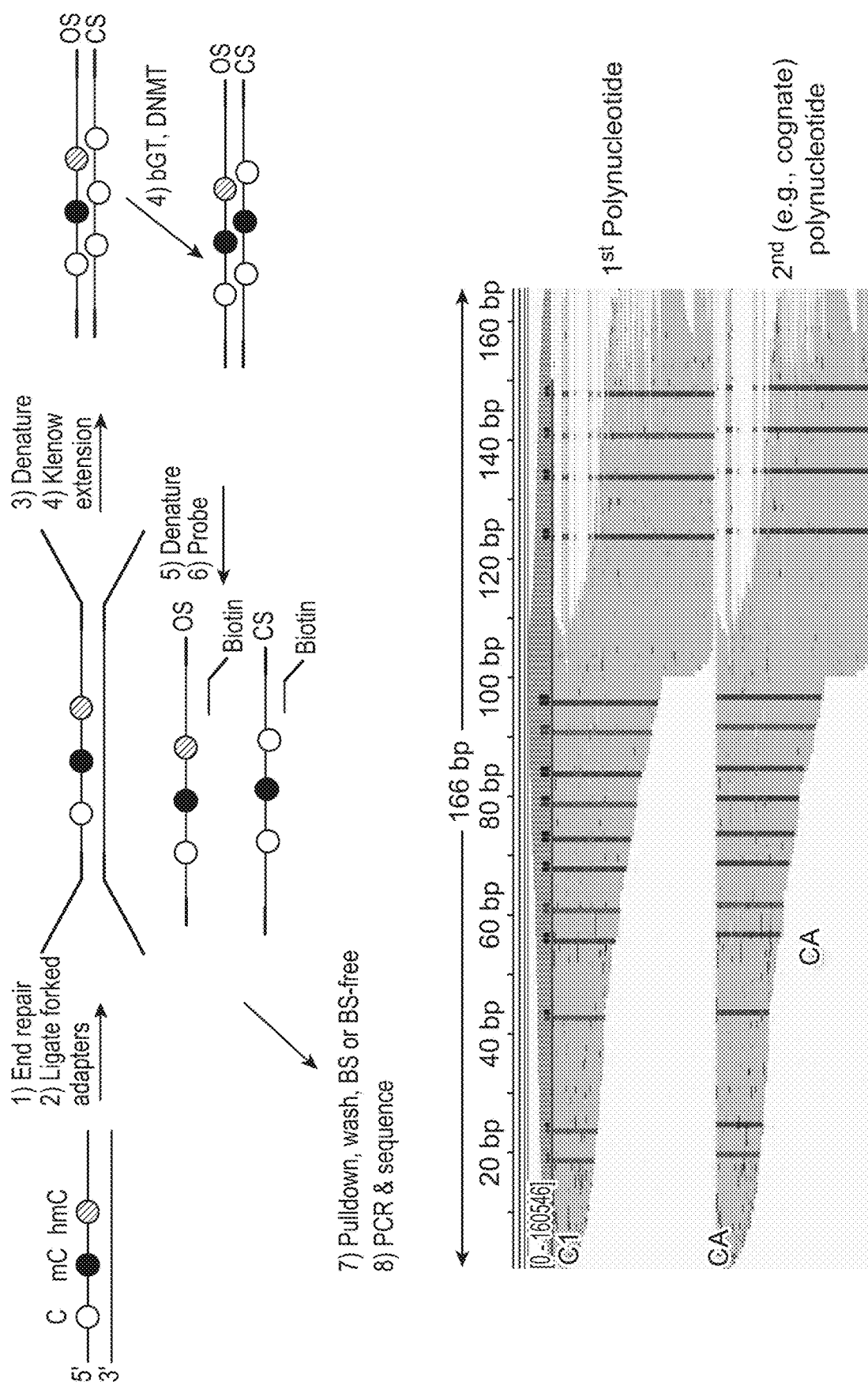
FIG. 9 depicts, among other things, a modified method for differentiating and identifying cytosine, mC, and hmC in a DNA sequence and an experimental data set, in accordance with embodiments.

FIG. 9 depicts a modified approach using a biotinylated probe. This scheme can involve on one or more of: 1) conditions for at least one hairpin; 2) a biotinylated probe— this probe can be protected from exonucleases; 3) such a method may use p5 and p7 adapters in a final PCR, and in some cases a restriction site can be used instead in this sequence; in some cases, this can be performed with an additional ligation event, as illustrated in FIG. 8; and 4) in the gap fill operation, APOBEC or BS indifferent dNTPs can be used. In some embodiments, such a method may not attempt to maintain individual first polynucleotide (OS) & second polynucleotide (CS) information but rather can rely on high depth coverage, for example to deconvolute mC and hmC at targeted sites. In some embodiments, such a method may not include single hairpin ligation.

Figure 18:
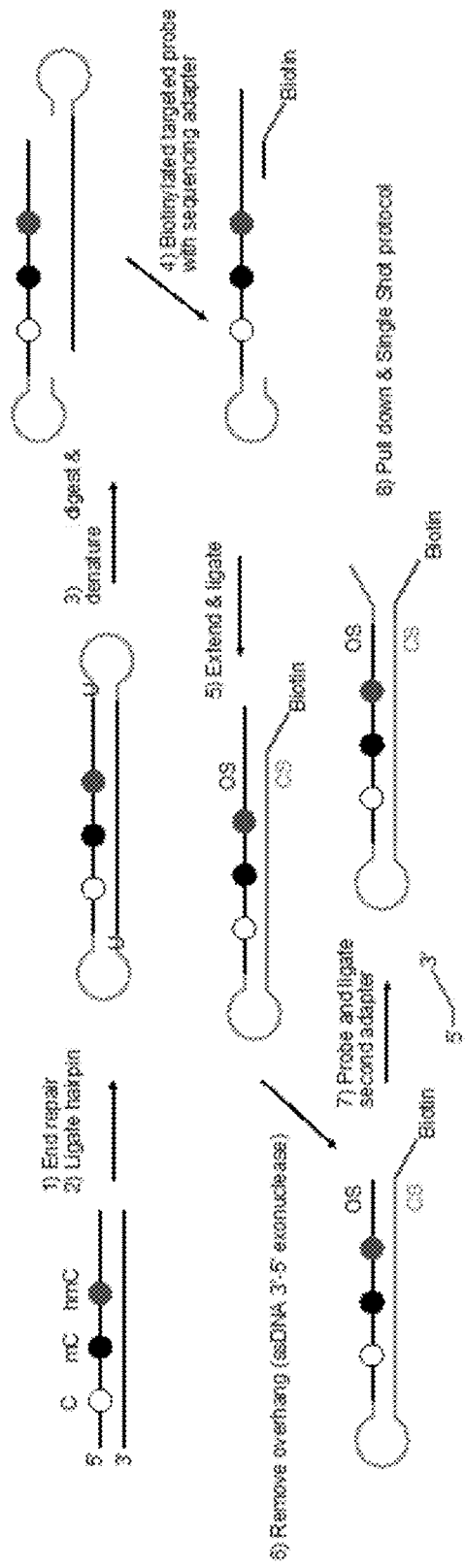
FIG. 18 depicts, among other things, methods employing simple targeting that can allow a primer to anneal to a 4-base genome following hairpin ligation prior to methods for differentiating and identifying cytosine, mC, and hmC in a DNA sequence provided herein.

Also provided herein are methods for simple targeting that can allow a primer to anneal to a 4-base genome (e.g., before conversion), for example as depicted in FIG. 18. In some embodiments, a method for single targeting can be incorporated into a method to differentiate and identify cytosine, mC, and hmC in a DNA sequence provided herein. Such a method can comprise, for example, one or more of (1) end repair, (2) hairpin ligation, (3) digest with a mixture of enzymes that generate a single nucleotide gap where a uracil or deoxyuracil was present, such as, for example, the enzymes Uracil DNA Glycosylase (UDG) and Endonuclease VIII; and denaturation, (4) biotinylation of a target probe with a sequencing adapter, (5) extension of the second polynucleotide and ligation of the second polynucleotide to the hairpin, (6) removal of an overhang (e.g., a 3' overhang) from the first polynucleotide, for example using a ssDNA 3'-5' exonuclease, (7) probing with and ligation of a second adapter, and (8) pull down. In some embodiments, this workflow can be followed by a method provided herein, for example a method to differentiate and identify cytosine, mC, and hmC in a DNA sequence. A non-limiting example of exonuclease activity that can perform removal of the overhang is provided in (Runnberg, R., Narayanan, S., Itriago, H. et al. Either Rap1 or Cdc13 can protect telomeric single-stranded 3' overhangs from degradation in vitro. Sci Rep 9, 19181 (2019). doi.org), which is incorporated by reference herein in its entirety.

FIG. 9 depicts another modified approach which can be independent of relative physical positions of the first polynucleotide and second polynucleotide. In some embodiments, this method can be high coverage, and may not deconvolute 5mC & 5hmC on single strands (single molecule level) but rather give a "global" view of targeted regions. Such methods can rely on UMIs also to capture individual strand (e.g., polynucleotide) information, in some embodiments. In some embodiments, such methods can maintain fragment information. For example, high coverage first polynucleotide (OS) & second polynucleotide (CS) reads in a method herein are shown in the right panel of FIG. 9. Individual strand information may or may not be maintained when coverage is high. In some cases, such a method may not attempt to maintain individual OS & CS information but rather can rely on high depth coverage, for example to deconvolute mC and hmC at targeted sites.

In some embodiments, a method provided herein can incorporate tagmentation. In some embodiments, tagmentation can be a process (e.g., for use in the analysis of DNA) in which DNA (e.g., double stranded DNA) can be cleaved and tagged. In some embodiments, tagmentation can comprise fragmentation of and adapter ligation operations performed on a DNA sample. This can be performed, for example, using a transposome, which can be a transposon complexed with a transposase. The transposome can make cuts in the DNA (e.g., transposase activity) and insert a DNA sequence that can be a portion of the transposome (e.g., a transposon sequence) in the DNA (e.g., transposon activity). In some embodiments, sequence inserted into DNA such as a transposon sequence can comprise adapter sequences. In some embodiments, the transposome can cleave DNA and insert. In some embodiments, DNA can be cut, and a transposon sequence can be performed simultaneously or essentially simultaneously. In some embodiments, the transposon sequence can be inserted following cutting the DNA. Insertion of a transposon sequence can be followed in some cases by a clean-up operation, that can comprise PCR amplification. Such a clean-up operation can remove transposome bound to the DNA to prevent interference with later operations. In some embodiments, a method comprising tagmentation may not require DNA fragment end repair or adapter ligation preparation. Tagmentation can be used, for example, to characterize cellular status of a sample. Non-limiting examples of incorporation of tagmentation as well as methods thereof are described in (Chen C, Xing D, Tan L, et al. Single-cell whole-genome analyses by Linear Amplification via Transposon Insertion (LIANTI). Science. 2017; 356(6334):189-194. doi:10.1126/science.aak9787) and (Raine A, Manlig E, Wahlberg P, Syvinen A C, Nordlund J. SPlinted Ligation Adapter Tagging (SPLAT), a novel library preparation method for whole genome bisulphite sequencing. Nucleic Acids Res. 2017; 45(6):e36. doi: 10.1093/nar/gkw1110), which are incorporated by reference herein in their entireties.

Figure 10:
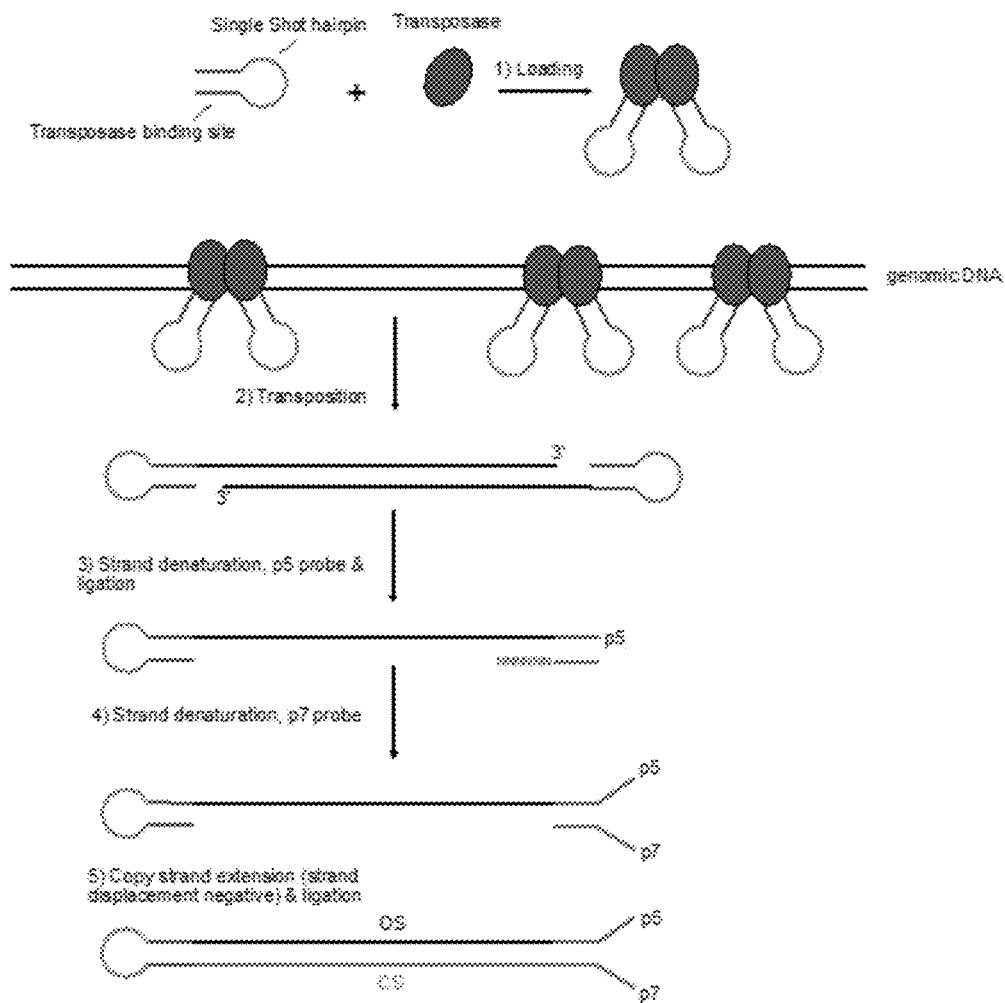
FIG. 10 depicts, among other things, an example of a method for incorporating tagmentation into a method for differentiating and identifying cytosine, mC, and hmC in a DNA sequence, in accordance with embodiments.

An example of how tagmentation can be incorporated into methods provided herein, for example methods for differentiating and identifying cytosine, mC, and hmC in a DNA sequence, is illustrated in FIG. 10. In this example, a transposome dimer comprising two subunits, each comprising a transposase and a DNA strand that can comprise a hairpin sequence and a transposase binding site can be applied to genomic DNA. The transposome can cut the genomic DNA and the transposome DNA can be annealed to the cut genomic DNA. Strand denaturation and ligation of a p5 probe can be performed, followed by another strand denaturation operation and annealing of a p7 probe, as pictured. This can be followed by second polynucleotide extension (e.g., strand displacement negative) and ligation to yield a DNA molecule comprising a first polynucleotide (OS) and a second polynucleotide.

Figure 11:
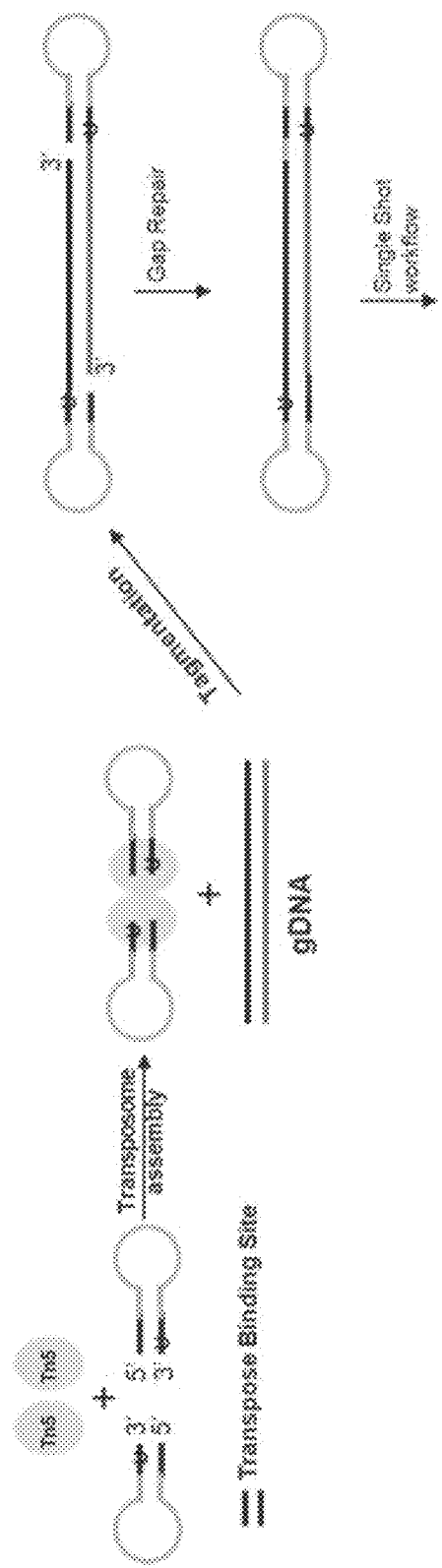
FIG. 11 depicts, among other things, an example of a method for incorporating tagmentation into a method for differentiating and identifying cytosine, mC, and hmC in a DNA sequence, in accordance with embodiments.

Another example of how tagmentation can be incorporated into methods provided herein, for example methods for differentiating and identifying cytosine, mC, and hmC in a DNA sequence, is illustrated in FIG. 11. In this example, two Tn5 transposases and two nucleic acid molecules each comprising a hairpin sequence and a transposon binding site (e.g., transpose binding site) can be combined to yield a transposome dimer. This transposome dimer can be applied to DNA (e.g., genomic DNA, gDNA), thus tagmenting the DNA to yield genomic DNA flanked by transposon binding sites and hairpin sequences. Gap repair can be performed on this tagmented DNA, and the resulting DNA molecule can be subjected to a method provided herein, for example a method for differentiating and identifying cytosine, mC, and hmC in a DNA sequence.

In some embodiments, the methods described herein can include the use of adapters for targeting a region of interest in the genome. In some cases, the adapters are PCR adapters. In some cases, the adapters can be designed to target the 5' or the 3' end of a region of interest in the genome. In some cases, the PCR adapter may comprise a targeting region that anneals to the 5' or the 3' end of a region of interest. In some cases, a second pair of targeted PCR adapters may be used for targeting the 5' or the 3' end of the region of interest. In some cases, the targeted PCR adapters may be used to add a next-generation sequencing adapter to the 5' or the 3' end of the region of interest. In some cases, the targeted PCR adapters may contain next-generation sequencing adapters in addition to the targeting region that anneals to the region of interest. In some cases, multiple adapters or targeting probes may be used for targeting multiple regions of interest in the genome. In some cases, a third probe may be used for targeting a region of interest. In some cases, a fourth probe may be used. In some cases, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 50, 56, 60, 64, 68, 72, 76, 80, 84, 88, 90, 94, 96, or 100 adapters or targeting probes are used.

In some cases, the adapters or probes may also include a barcode. In some cases, the adapters (e.g., PCR adapters) or targeting probes are protected from deamination. In some cases, the protection in adapters can be achieved by incorporation of mC, 5hmC, fC or caC nucleotides, in some cases, the PCR adapters contain nucleotides that are converted to an APOBEC3A resistant nucleotide (ghmC, fC or caC). In some cases, the adapters (e.g., PCR adapters) can also contain an index that is protected from deamination via APOBEC3A. In some cases, the targeting probes may be used with a non-strand displacement enzyme. In some cases, the non-strand displacement enzyme is T4. In some cases, an ssDNA exonuclease is used to remove the overhang after gap filling. In some cases, the gap filling is extended with APOBEC3A resistant nucleotides. In some cases, a strand displacement negative polymerase is mandatory used for gap filling during PCR. In some cases, the gap filling is followed by ligation. In some cases, the adapters that are protected from deamination. In some cases, the hairpin can include modified bases that are protected from deamination. In some cases, the protection in adapters can be achieved by incorporation of mC, 5hmC, fC or caC nucleotides, In some cases, the PCR adapters contain nucleotides that are converted to an APOBEC3A resistant nucleotide (ghmC, fC or caC). In some cases, the protection in the hairpin can be achieved by mC, 5hmC, fC or caC for example, as these will undergo conversion to an APOBEC3A resistant nucleotide (ghmC, fC or caC). In some cases, the hairpin may comprise a custom indexing barcode.

In some case, the probe may contain a molecular attachment suitable for pulldown. In some cases, the attachment is an affinity probe. In some cases, the affinity probe is a biotin molecule. In some cases, the affinity probe is an aptamer. In some cases, the affinity probe is a peptide. In some cases, the sequencing may also involve sequencing of the hairpin. In some cases, the adapters can be designed sequencing can be designed for long read sequencing on an Illumina platform. In some cases, the sequencing may also involve sequencing of the hairpin. In some cases, the adapters can be designed sequencing can be designed for short read sequencing on an Illumina platform. In some cases, the adapter is a 4 base probe. In some cases, the adapter is designed for 3 base targeting. In some cases, the adapter is 5 bp long. In some cases, the adapter is 6 bp long. the adapter is 7 bp long. In some cases, the adapter is 8 bp long. In some cases, the adapter is 9 bp long. In some cases, the adapter is 10 bp long In some cases, the starting DNA material is denatured (e.g. using temperature denaturation). In some cases, in order to target a region of interest (ROI), a targeting primer is used. In some cases, the targeting primer is designed to be a 4 base probe. In some cases, the targeting probe is designed to target the 5' end of the region of interest. In some cases, the targeting probe is designed to target the 3' end of the region of interest. In some cases, the targeting primer may contain an Illumina custom index for indexing individually captured strands. In some cases, a second pair of targeting probes are used to target the 5' end of the ROI. In some cases, the second targeting probe may be a 3 base probe. In some cases, the use of pairs of probes is used for creating PCR handles. In some cases, the PCR adapter is a staggered duplex. In some cases, the adapter may also contain an index. In some cases, the PCR adapter has a targeting sequence that primes the 5' end of the ROI. In some examples, after priming the ROI at the 5' and 3' ends of ssDNA, the "gaps" can be filled using a strand-displacement negative polymerase (such as T4 for example), followed by ligation (T4 ligase for example). In some cases, the epigenetic base mC may be copied over from the original strand to the copied strand. In some cases, the 5hmC can be protected from deamination by treatment with bGT enzyme. In some cases, the construct is treated with TET (in the presence or absence of bGT) to convert mC to fC, caC or ghmC. In some cases, the hairpin is opened up using a combination of APOBEC3A and the helicase UvrD (FIG. 48, described further in Example 18), or fragments thereof. When targeting multiple regions of interest, the methods can be used in combination with another method such as massively multiplexed PCR.

Figure 49:
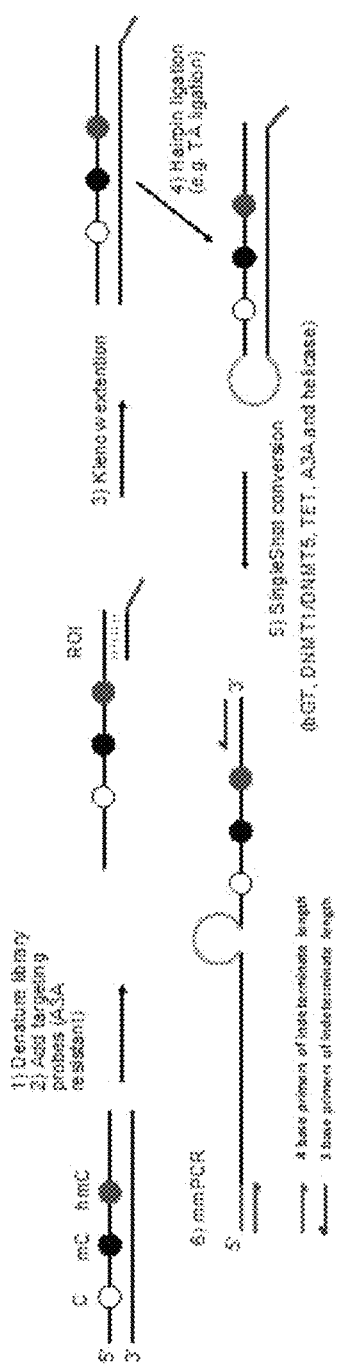
FIG. 49 depicts the representation of an example workflow for the measurement of epigenetic information in a targeted region of interest in the genome.

In some case, the starting DNA material is first denatured (e.g. using temperature denaturation). In some cases, an adapter or primer oligonucleotide is designed to target a region of interest (ROI). In some cases, the adapter contains an additional sequence for PCR amplification. In some cases, the adapter is a 4 base probe. In some cases, the adapter may comprise an additional sequence that may contain an index. In some cases, the adapter may comprise an Illumina sequencing adapter. In some cases, the adapter may be used to add an Illumina sequencing adapter in a later PCR operation. In some cases, the adapter is protected from deamination. In some cases, the adapter is protected from deamination from APOBEC3A, for example, by containing a APOBEC3A resistant base (e.g. hmC, fC or caC). In some cases, the annealed primer or adapter is extended with Klenow polymerase. In some cases, a hairpin is added by first A-tailing, and then using a hairpin with a T-overhang and ligating the hairpin to the construct to generate a construct for two-base sequencing. In some examples, the epigenetic modification (e.g., methylation) copied over form the original strand to the copied strand. In some cases, the 5hmC can be protected from deamination by treatment with bGT enzyme. In some cases, the construct is treated with TET (in the presence or in the absence of bGT) to oxidise mC to fC, caC or ghmC. In some cases, the hairpin is then treated using a combination of APOBEC3A and the helicase UvrD, or fragments thereof. In some cases, the PCR handles can be used to amplify the ROI in combination with a second targeting oligonucleotide (FIG. 49, described further in Example 18). In some cases, the second targeting nucleotide is a 3 base probe. In some cases, the methods can be used for targeting multiple regions of interest. In some cases, the methods can be used in combination with another method such as massively multiplexed PCR.

Figure 50:
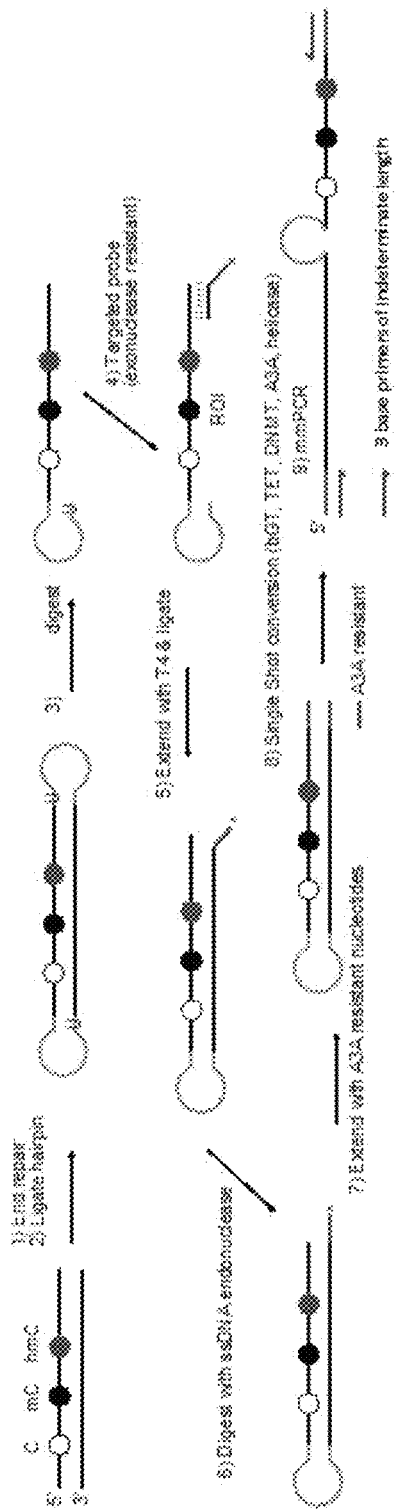
FIG. 50 depicts the representation of an example workflow for the measurement of epigenetic information in a targeted region of interest in the genome.

In some examples, the starting double-stranded DNA is end-repaired. In some examples, the starting double-stranded DNA is A-tailed. In some cases, the starting DNA is adapted with hairpin using "TA" ligation whereby the hairpin contains a T overhang that primes and is used to ligate hairpin on either side of the DNA. In some cases, the hairpin contains a U and so can be cut using a mixture of enzymes that generate a single nucleotide gap where a uracil or deoxyuracil was present, such as, for example, the enzymes Uracil DNA Glycosylase (UDG) and Endonuclease VIII. In some cases, a probe is used to prime to the 3' end of the said DNA construct such that it now flanks the hairpin on the opposite side of the ROI. In some cases, the probe is 4 bases. In some cases, the oligo is protected from APOBEC3A deamination. In some cases, the oligonucleotide or adapter is protected from APOBEC3A deamination, for example, by containing a APOBEC3A resistant base (e.g. hmC, fC or caC). In some cases, the 5' end of the oligonucleotide/adapter is exonuclease resistant by containing modified bases (e.g. phosphorothioates derivatives). In some cases, Illumina sequencing adapters are added to the adapters in a further PCR treatment. In some cases, the original PCR adapters contains extended primers that contain the PCR handle sequence and the Illumina adapters. In some cases, the oligonucleotide or adapter may contain an index. In some cases, the oligonucleotide or adapter is primed and is extended with a strand displacement negative polymerase that does not displace the hairpin. In some cases, the copy strand is then ligated to the hairpin. In some cases, the potential mismatch at the 3' end can be trimmed with a ssDNA specific exonuclease, and the complementary sequence built with a polymerase using APOBEC3A resistant bases such as fC or caC. In some cases, the epigenetic base mC can be copied over from the original strand to the copied strand. In some cases, the 5hmC can be protected from deamination by treatment with bGT enzyme. In some cases, the construct is treated with TET (in the presence or the absence of bGT) to oxidise mC to fC, caC or ghmC. In some cases, the hairpin is opened up using a combination of APOBEC3A and the helicase UvrD. In some cases, the ROI can now be amplified using the deamination resistant PCR handles (FIG. 50, described further in Example 18). In some cases, the methods can be used for targeting multiple regions of interest. In some cases, the methods can be used in combination with another method such as massively multiplexed PCR.

In some embodiments, a long-read technology can be incorporated into methods provided herein, for example methods for differentiating and identifying cytosine, mC, and hmC in a DNA sequence. Third generation sequencing (e.g., long-read sequencing) can be used, for example, to generate synthetic long reads (e.g., for de novo assembly and genome finishing applications), to sequence challenging genomes (e.g., those containing stretches of highly repetitive elements), or to perform whole genome phasing (e.g., to identify co-inherited alleles, haplotype information, or phase de novo mutations). In some embodiments, for example, a long-read technology can incorporate rolling circle amplification (RCA). Rolling circle amplification can be a process of unidirectional nucleic acid replication that can rapidly synthesize a plurality of copies of DNA or RNA. In some embodiments, RCA can amplify DNA from small to very small amounts of starting material. RCA can be an isothermal nucleic acid amplification technique where a polymerase can continuously add single nucleotides to a primer annealed to a circular template. In some embodiments, RCA can yield a long concatemer single stranded DNA molecule (ssDNA) that can comprise tens to hundreds of tandem repeats. Such tandem repeats can be complementary to the circular template. Components used in an RCA reaction can include a DNA polymerase, a suitable buffer compatible with the polymerase, a short DNA or RNA primer, a circular DNA template and deoxynucleotide triphosphates (dNTPs). RCA can comprise one or more operations, which can include: (1) circular template ligation, which can be conducted via template mediated enzymatic ligation (e.g., T4 DNA ligase) or template-free ligation using special DNA ligases (e.g., CircLigase), (2) primer induced single-strand DNA elongation, and (3) use of the amplification product in a method. Herein, RCA can be employed to amplify circulating free DNA (cfDNA) so it can be read in long reads, and can allow multiple reads of the same cfDNA fragment. In some embodiments, this can allow for extreme error correction. A non-limiting example of use of such an RCA method is provided in (Wilson B D, Eisenstein M, Soh H T. High-Fidelity Nanopore Sequencing of Ultra-Short DNA Targets. Anal Chem. 2019; 91(10):6783-6789. doi:10.1021/acs.analchem.9b00856) which is incorporated by reference herein in its entirety.

Herein, a nucleic acid molecule can be a molecule which can be a chain of nucleotides. Nucleic acid molecules described herein can comprise ribonucleic acids (RNA). Nucleic acid molecules described herein can comprise deoxyribonucleic acids (DNA).

Figure 12:
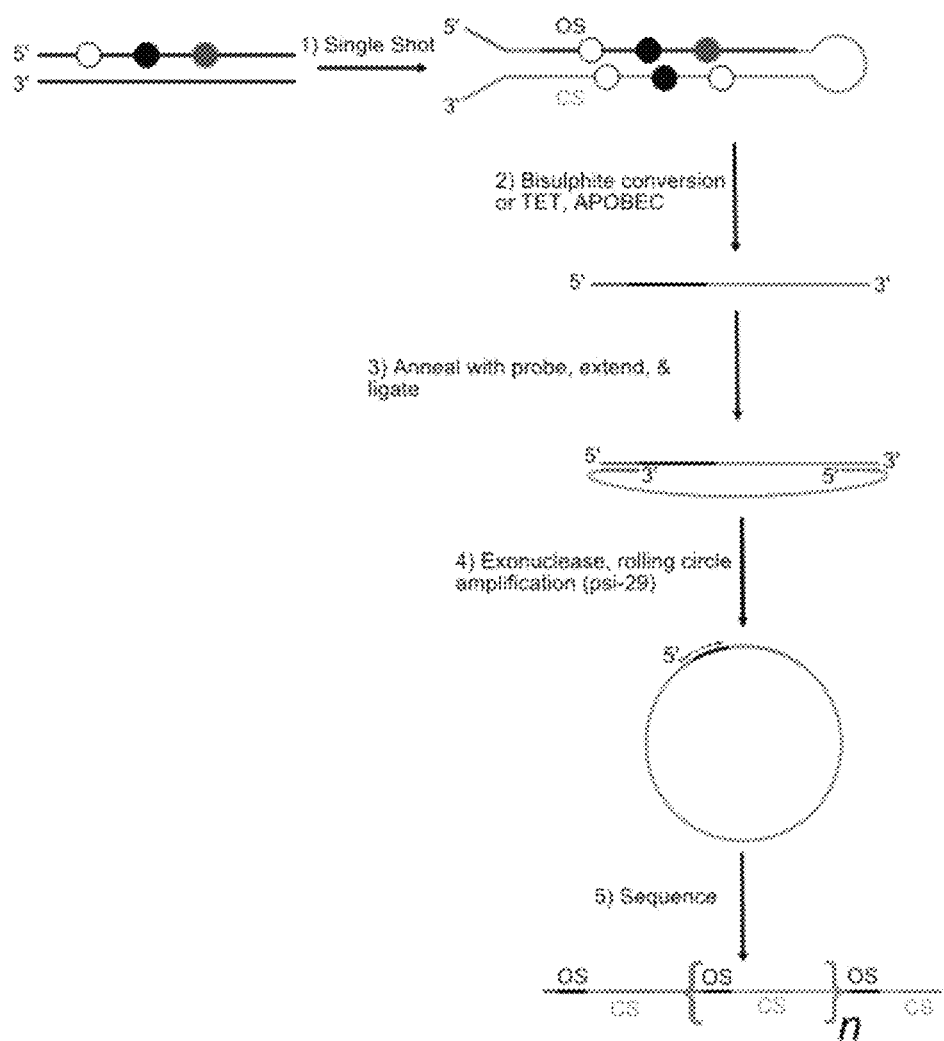
FIG. 12 depicts, among other things, an example adaptation of a method for differentiating and identifying cytosine, mC, and hmC in a DNA sequence for long read sequencing using rolling circle amplification, in accordance with embodiments.

An example of how RCA can be used to incorporate long-read technology into methods for differentiating and identifying cytosine, mC, and hmC in a DNA sequence is provided in FIG. 12. In some embodiments, RCA can be performed after a method for differentiating and identifying cytosine, mC, and hmC in a DNA sequence, as depicted in FIG. 12. In some embodiments, the methods comprise performing an RCA as part of differentiating and identifying cytosine, mC, and hmC in a DNA sequence, or between any two operations of a method for differentiating and identifying cytosine, mC, and hmC in a DNA sequence. For example, a circular primer or padlock probe can be applied such that it can anneal to the 5' end and the 3' end of the DNA strand to be sequenced. RCA can be performed (e.g., using any acceptable polymerase, such as psi29 or another polymerase) to yield a long DNA sequence comprising n copies of a first polynucleotide (e.g., forward or reverse polynucleotide) and a second polynucleotide (e.g., cognate polynucleotide) of the double-stranded DNA polynucleotide comprising the first and second polynucleotides. In some embodiments, n can be at least about 2, at least about 5, at least about 10, at least about 20, at least about 30, at least about 40, at least about 50, at least about 100, at least about 500, or at least about 1000. In some embodiments, n can be not more than about 5, not more than about 10, not more than about 20, not more than about 30, not more than about 40, not more than about 50, not more than about 100, not more than about 500, or not more than about 1000. In some embodiments, n can be about 2, about 5, about 10, about 20, about 30, about 40, about 50, about 100, about 500, about 1000, or a range between any two foregoing values.

Figure 13:
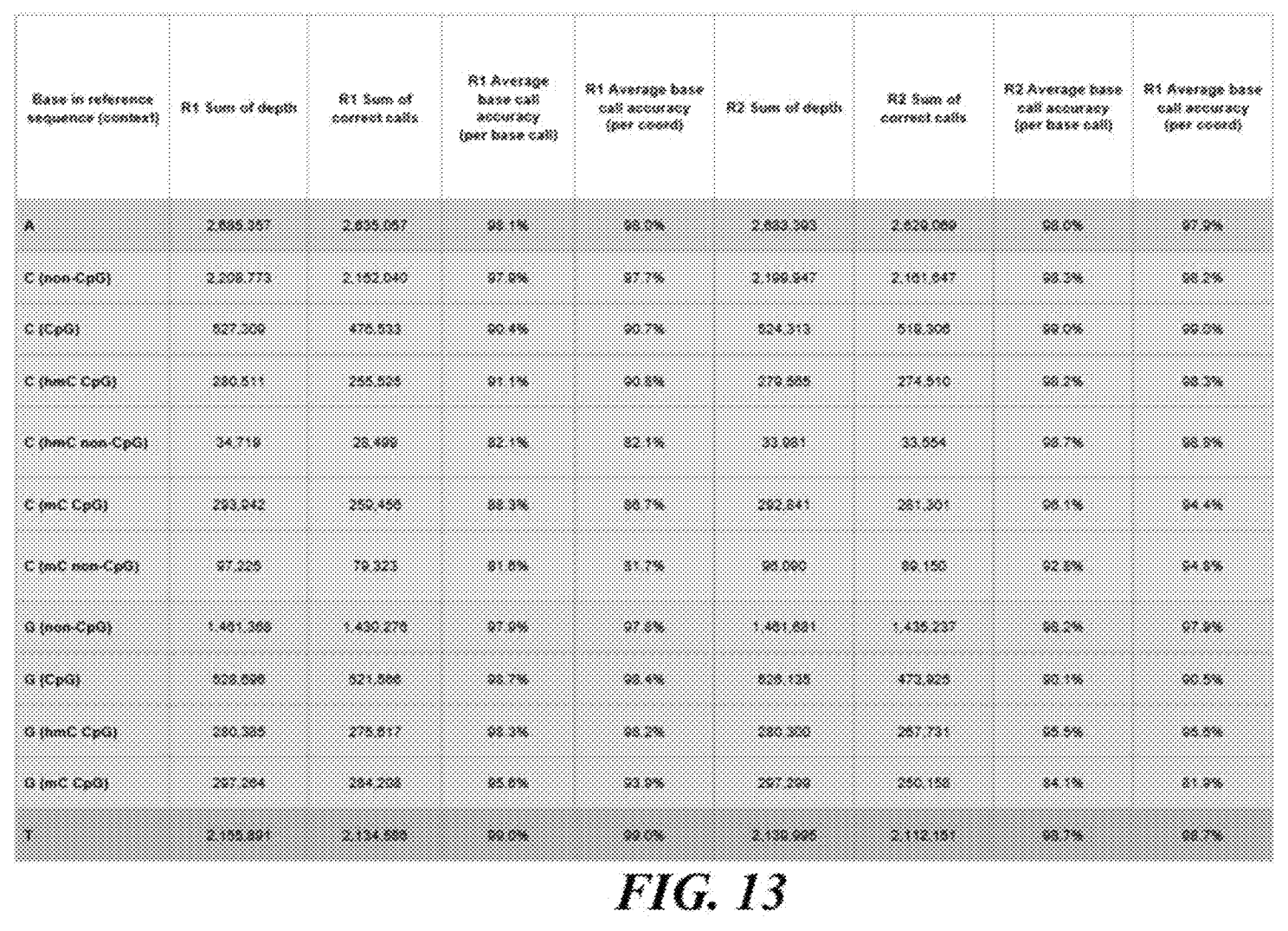

In some embodiments, a method for differentiating and identifying cytosine, mC, and hmC in a DNA sequence provided herein can produce a conversion rate that is about as good as or better than an alternative methodology. Calculations for the conversion rate can be, for example, as depicted in the table of FIG. 13, which was populated using data from a 166-nucleotide spike-in controls in alongside cerebellum genomic DNA in an experiment using a method differentiating and identifying cytosine, mC, and hmC in a DNA sequence provided herein. Notably, in some embodiments the percent accuracy of calls for A can be at least about 97.5%, the percent accuracy of calls for C can be at least about 95.6%, the percent accuracy of calls for G can be at least about 97.1%, the percent accuracy of calls for T can be at least about 98.4%, the percent accuracy of calls for mC can be at least about 80.8%, the percent accuracy of calls for hmC can be at least about 84.5%, and the percent accuracy of calls for methylation in a non CpG context can be at least about 83.4%. In some embodiments the percent accuracy of calls for A can be at least about 80%, at least about 90%, at least about 95%, at least about 96%, at least about 97%, at least about 98%, at least about 99%, at least about 99.9%, at least about 99.99%, or higher; the percent accuracy of calls for C can be at least about 80%, at least about 90%, at least about 95%, at least about 96%, at least about 97%, at least about 98%, at least about 99%, at least about 99.9%, at least about 99.99%, or higher; the percent accuracy of calls for G can be at least about 80%, at least about 90%, at least about 95%, at least about 96%, at least about 97%, at least about 97.5%, at least about 98%, at least about 99%, at least about 99.9%, at least about 99.99%, or higher; the percent accuracy of calls for T can be at least about 80%, at least about 90%, at least about 95%, at least about 96%, at least about 97%, at least about 98%, at least about 98.5%, at least about 99%, at least about 99.9%, at least about 99.99%, or higher; the percent accuracy of calls for mC can be at least about 80%, at least about 82.5%, at least about 85%, at least about 87%, at least about 89%, at least about 90%, at least about 95%, at least about 96%, at least about 97%, at least about 98%, at least about 99%, at least about 99.9%, at least about 99.99%, or higher; the percent accuracy of calls for hmC can be at least about 80%, at least about 85%, at least about 90%, at least about 95%, at least about 96%, at least about 97%, at least about 98%, at least about 99%, at least about 99.9%, at least about 99.99%, or higher; and the percent accuracy of calls for methylation in a non CpG context can be at least about 80%, at least about 84%, at least about 85%, at least about 86%, at least about 90%, at least about 95%, at least about 96%, at least about 97%, at least about 98%, at least about 99%, at least about 99.9%, at least about 99.99%, or higher. In some embodiments, inaccuracies may be suspected in the spike-in synthesis. In some embodiments, the method can be further optimized to yield a higher percent accuracy for one or more call types provided above.

Figure 14:
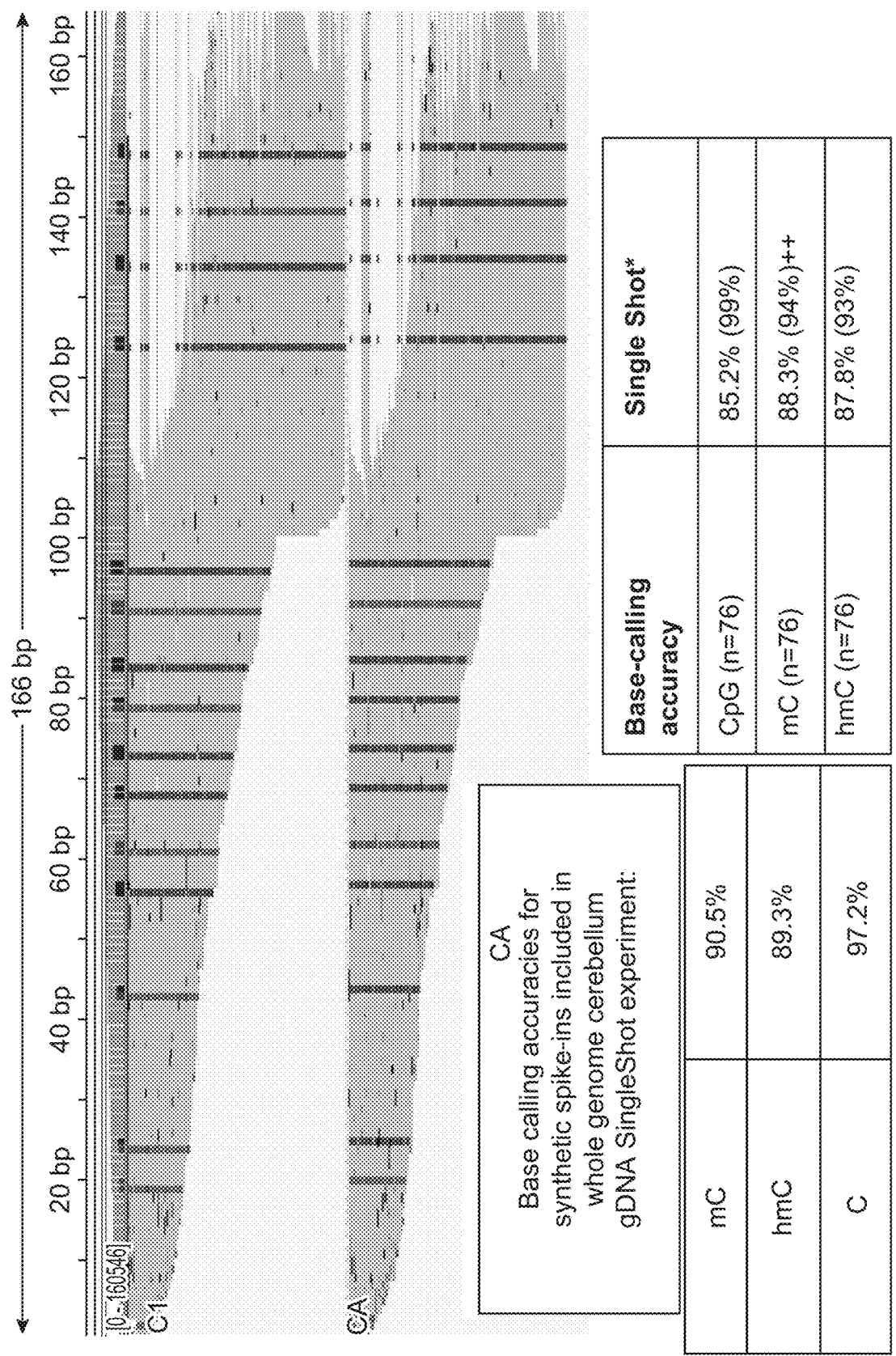
FIG. 14 depicts, among other things, experimental data and base calling accuracy for a method for differentiating and identifying cytosine, mC, and hmC in a DNA sequence provided herein.

FIG. 14 depicts sequencing data from a first polynucleotide and a second polynucleotide of a DNA molecule subjected to a method for differentiating and identifying cytosine, mC, and hmC in a DNA sequence provided herein. Here, base call accuracy averages and measurements are reported in over 76 different library preparations. Here, the base calling accuracy for CpG (n=76) was about 85.2% (99%), the base call accuracy for mC (n=76) was about 88.3% (94%), and the base calling accuracy for hmC (n=76) was about 87.8% (93%). Base calling accuracy for spike-ins in whole genome cerebellum and genomic DNA (gDNA) experiments shown in FIG. 14 reflected 90.5% accuracy for 5-methylcytosine (mC), 89.3% accuracy for 5-hydroxymethylcytosine (hmC), and 97.2% accuracy for (e.g., unmethylated) cytosine. In some cases, base call accuracy for mC can be greater than 85%, greater than 87%, or greater than 90%. In some cases, base call accuracy for hmC can be greater than 85%, greater than 87%, greater than 89%, or greater than 90%. Percentages are reported for accuracy averages for the DNA sample, with the percentage accuracy average for a lambda phage (control) in parentheses. Lambda phage mC conversion rates were about 93.5%. In some embodiments, reduction of error within synthetic probes can improve the mC conversion rate.

Figure 27:
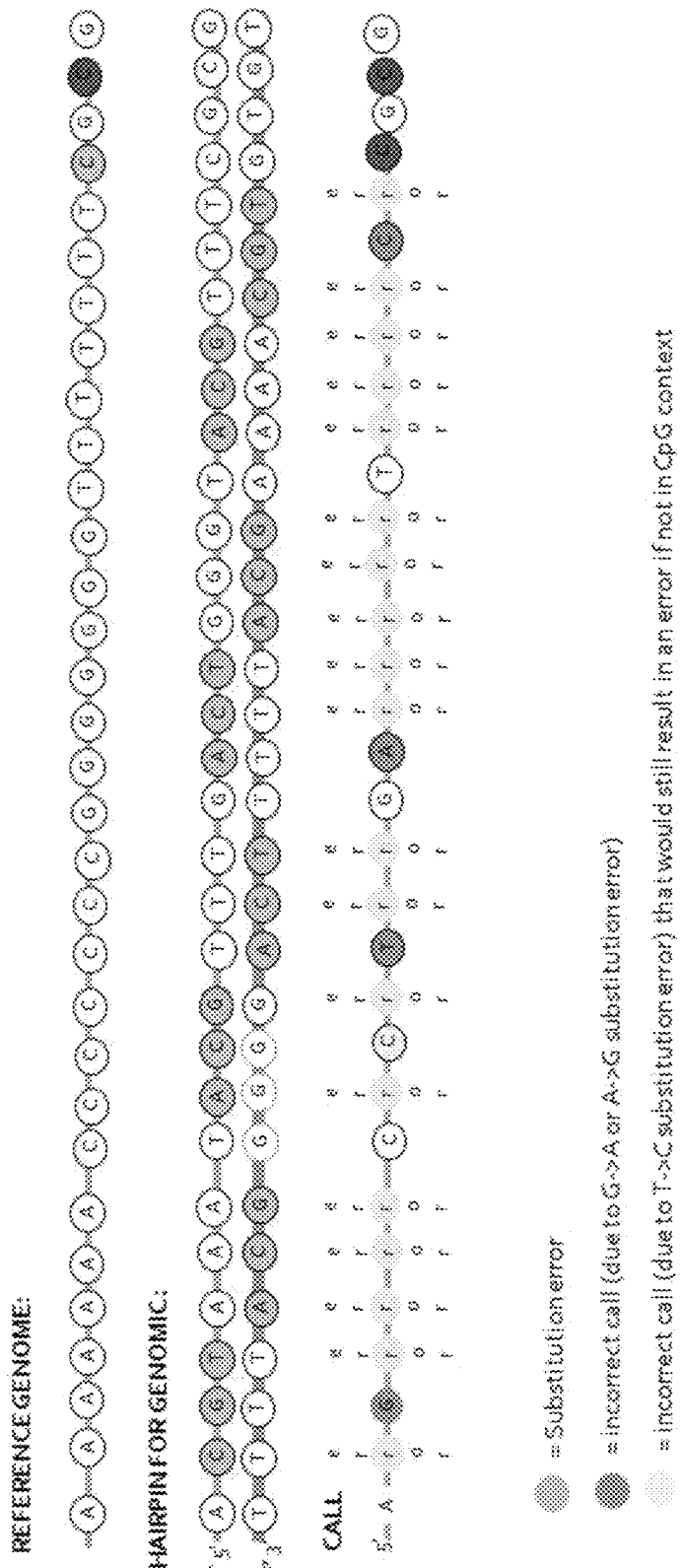
FIG. 27 depicts substitution errors that may occur during high-throughput sequencing and subsequent base calling during the two-base sequencing readout operations.

FIG. 27 depicts example G→A and A→G errors during amplification (e.g., PCR) or sequencing that can lead to miscalls which are not suppressed in embodiments described herein, including during sequencing. In the example depicted in FIG. 27, the top line (labelled reference genome) depicts the true base. The next two lines (listed genomic hairpin) depict the bases in the hairpin that are derived from the true base after conversion chemistry (e.g., bisulfite treatment, APOBEC+helicase). The bottom line (labelled call) depicts the base that is called from the hairpin after that hairpin is sequenced and the paired-end reads resolved (e.g., prior to any genomic alignment).

In the hairpin line: For a true base e.g. A, the correct pairing (e.g. A/T) is depicted (in white circles) followed by every possible one-base-error that can be introduced during strand copy, amplification (e.g., PCR) or sequencing (in yellow circles) on either strand of the hairpin (for instance A/T is changed variously to C/T G/T, T/T, A/A, A/C, A/G). In this example, nineteen out of twenty-four possible cases where one-base error is introduced to the hairpin, result in a pair of bases that do not exist (e.g. A/A) and are called as an error. Four of the twenty-four possible one-base errors result in a miscall where the correct base is called as another base. Two of these are the result of an error that changes A to G, the other two an error that changes G to A. They result in either the true A base being called G, the true G base being miscalled A, the true C base being miscalled T or the true T base being miscalled C. One of the 24 possibilities is an error that changes a T to a C and may result in the true base unmodified C being called as modified C. Any other type of miscalls (e.g. A→C) can be due to two errors introduced into the hairpin (e.g. A/T→T/G).

Figure 15:
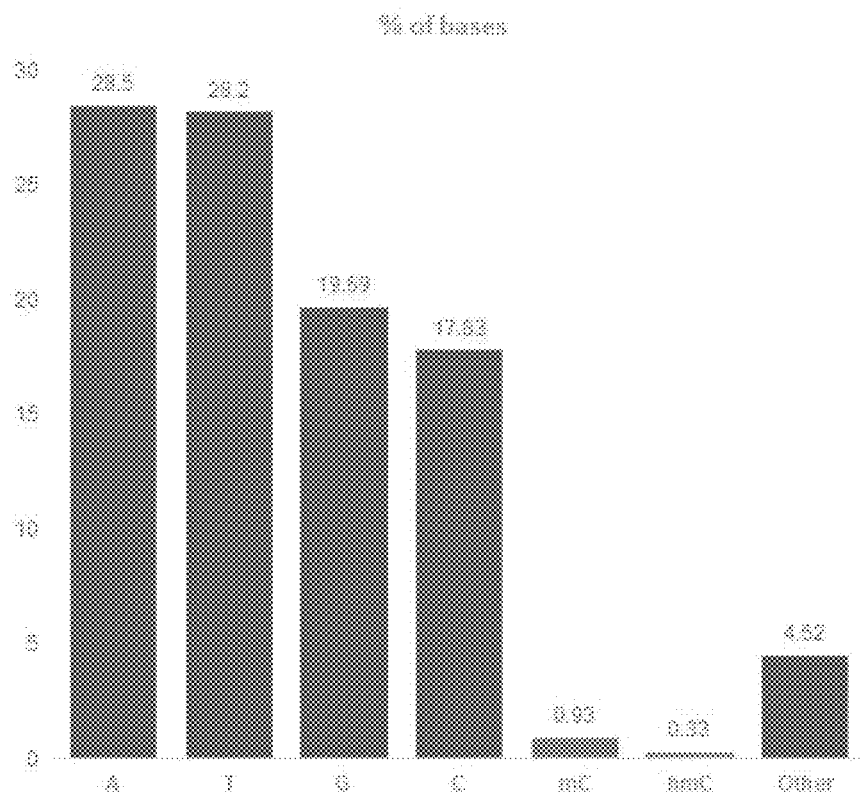
FIG. 15 depicts, among other things, percent occurrence of bases and methylated bases identified in a human cerebellum genomic DNA whole genome sample using a method for differentiating and identifying cytosine, mC, and hmC in a DNA sequence provided herein.

In some embodiments, the percent occurrence of bases or methylated bases can be calculated after implementation of a method for differentiating and identifying cytosine, mC, and hmC in a DNA sequence provided herein. For example (e.g., as demonstrated by experimental data presented in FIG. 15), whole genome gDNA was prepared from a human cerebellum sample as described in (Field S F, Beraldi D, Bachman M, Stewart S K, Beck S, Balasubramanian S. Accurate measurement of 5-methylcytosine and 5-hydroxymethylcytosine in human cerebellum DNA by oxidative bisulfite on an array (OxBS-array). PLoS One. 2015; 10(2):e0118202. Published 2015 Feb. 23. doi:10.1371/journal.pone.0118202), which is incorporated by reference herein in its entirety, and subjected to a method for differentiating and identifying cytosine, mC, and hmC in a DNA sequence provided herein. As a control, the gDNA was also subjected to global measures by mass spectrometry. In this sample, 28.5% of bases were identified as A, 28.2% of bases were identified as T, 19.69% of bases were identified as G, 17.83% of bases were identified as C, 0.93% of bases were identified as mC, 0.33% of bases were identified as hmC, and 4.52 bases were identified as other bases. Here, the mass spectrometry method identified 4.9% of cytosines in the sample as mC and 1.14% of the cytosines in the sample as hmC, while the method provided herein identified 5.2% of the cytosines in the sample as mC and 1.8% of the cytosines in the sample as hmC. In some embodiments, data may be further corrected (e.g., for an over-estimation due to a presence of spike-in controls) by filtering out the spike in controls.

Figure 16:
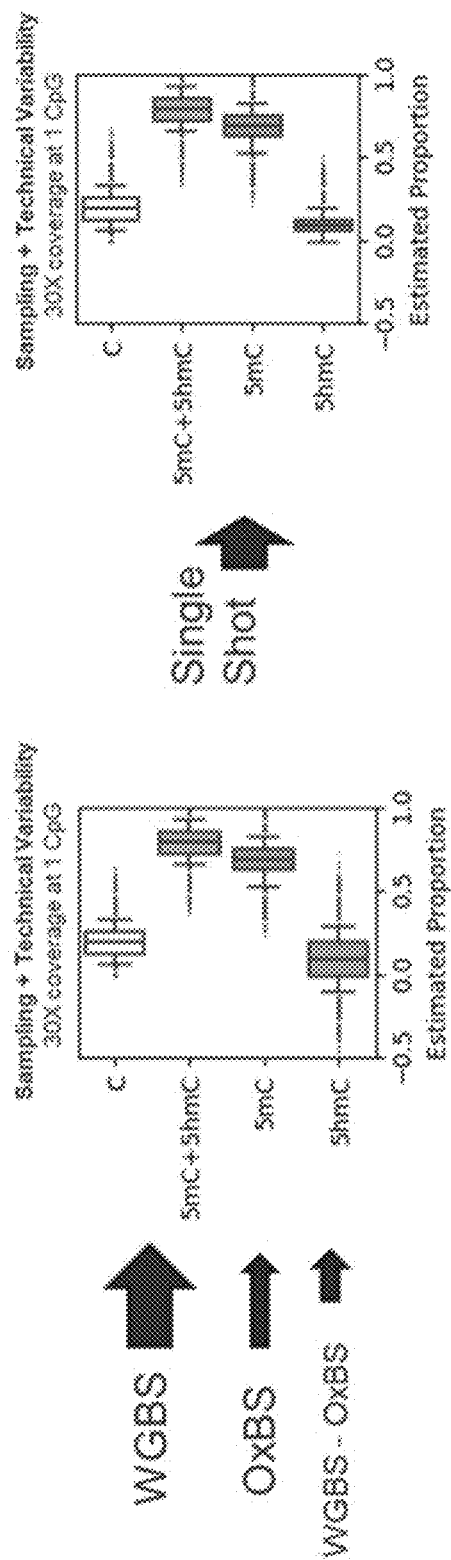
FIG. 16 depicts, among other things, relationships between technical variability of independent and concurrent measurement of DNA modifications.
Figure 17:
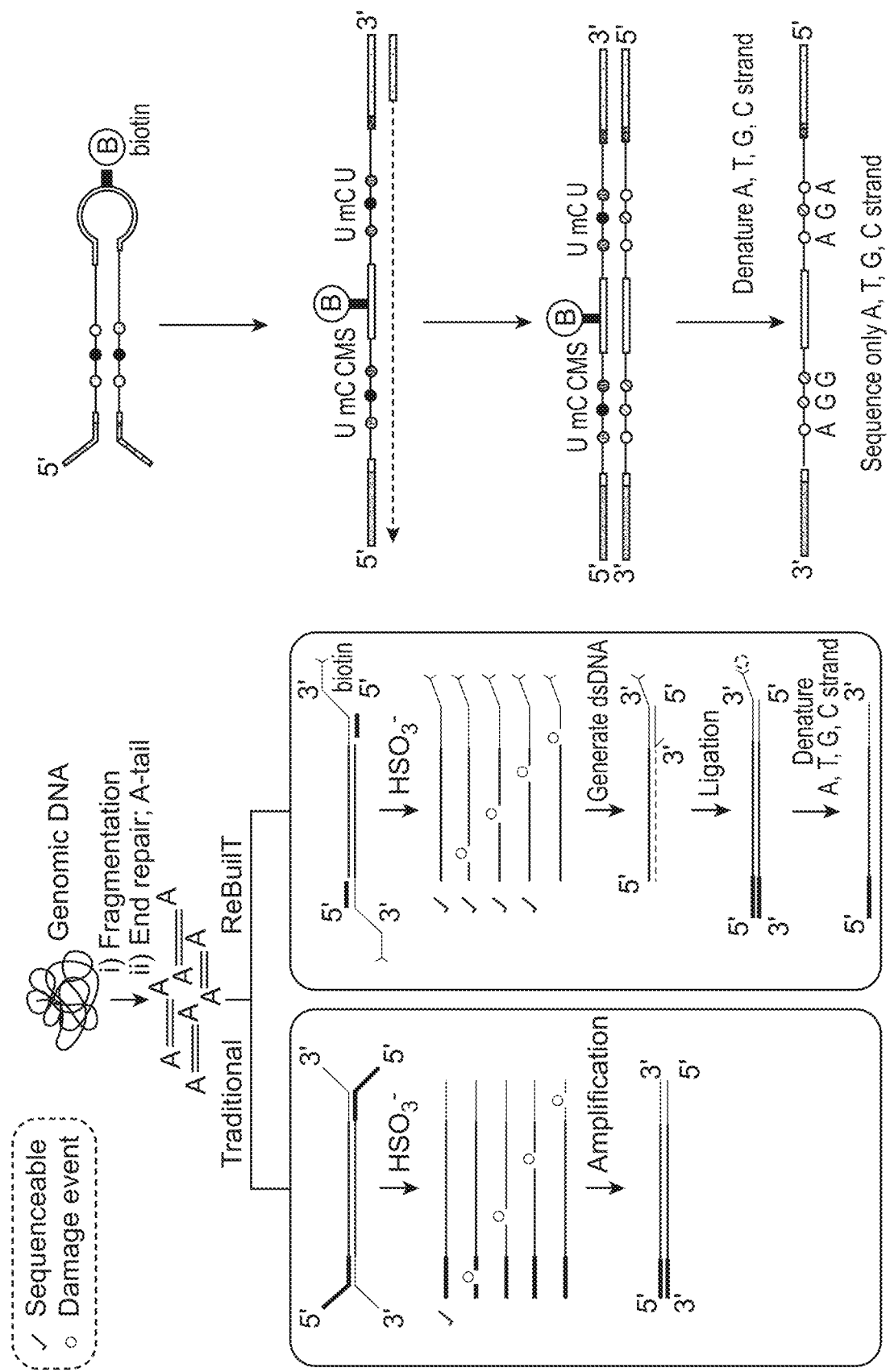
FIG. 17 depicts, among other things, a PCR-free workflow for methods for differentiating and identifying cytosine, mC, and hmC in a DNA sequence provided herein, in accordance with embodiments.

In some embodiments, independent measurement of DNA modifications can result in increased management of sampling or technical error/variability. Independent experiments can in some cases lead to incoherent estimation of methylation levels (e.g., dual workflow). Methods provided herein can lower sampling or technical variability for a similar sequencing volume compared with another method. For example, using a dual workflow method can result in a standard deviation of +/−0.12 (IQR 0.2) from 5hmC estimation, while a method provided herein can result in a standard deviation of +/−0.06 (IQR 0.07) for 5hmC estimation for the same sample. This data is depicted in FIG. 16, with data for a simulation of the dual method presented in the left panel and data for a simulation of the method provided herein in the right panel. The dual method simulation comprised simulation of OxBS and WGBS sampling combined with technical variability via BetaBinomial distribution. The simulation of the method provided herein comprised simulation of a pethood provided herein and technical variability via Dirichlet multinomial distribution. True levels for cytosine residues in the simulation were 5mC=−0.7, 5hmC=0.1, and C=0.2. Technical variability was assumed to be the same for both assays. Whiskers in the plots denote $5^{th}$ and $95^{th}$ percentiles.

In some embodiments, one or more polynucleotides comprising one or more barcodes (e.g., one or more unique molecular identifier, UMI) can be used in the methods and systems (e.g., comprising two-base sequencing) presented herein. For example, one or more unique barcodes can be attached to a first polynucleotide and one or more unique barcodes can be attached to a second polynucleotide (and/or read polynucleotide). In some cases, methods disclosed herein (e.g., two-base sequencing methods) can be performed without linking a first and second polynucleotide with another structure, such as a hairpin, for instance if the first and second polynucleotides (e.g., and a read polynucleotide) are tagged with a barcode (e.g., by ligating the barcode to the polynucleotide(s)). In some cases, a sequencing adapter (or hairpin polynucleotide) can comprise a barcode (e.g., a UMI). In some cases, a barcode can be installed on a first, second, and/or read polynucleotide by ligating a hairpin polynucleotide (or other polynucleotide structure) and then removing (e.g., enzymatically) the portion of the hairpin or other polynucleotide structure that does not comprise the barcode.

Figure 22:
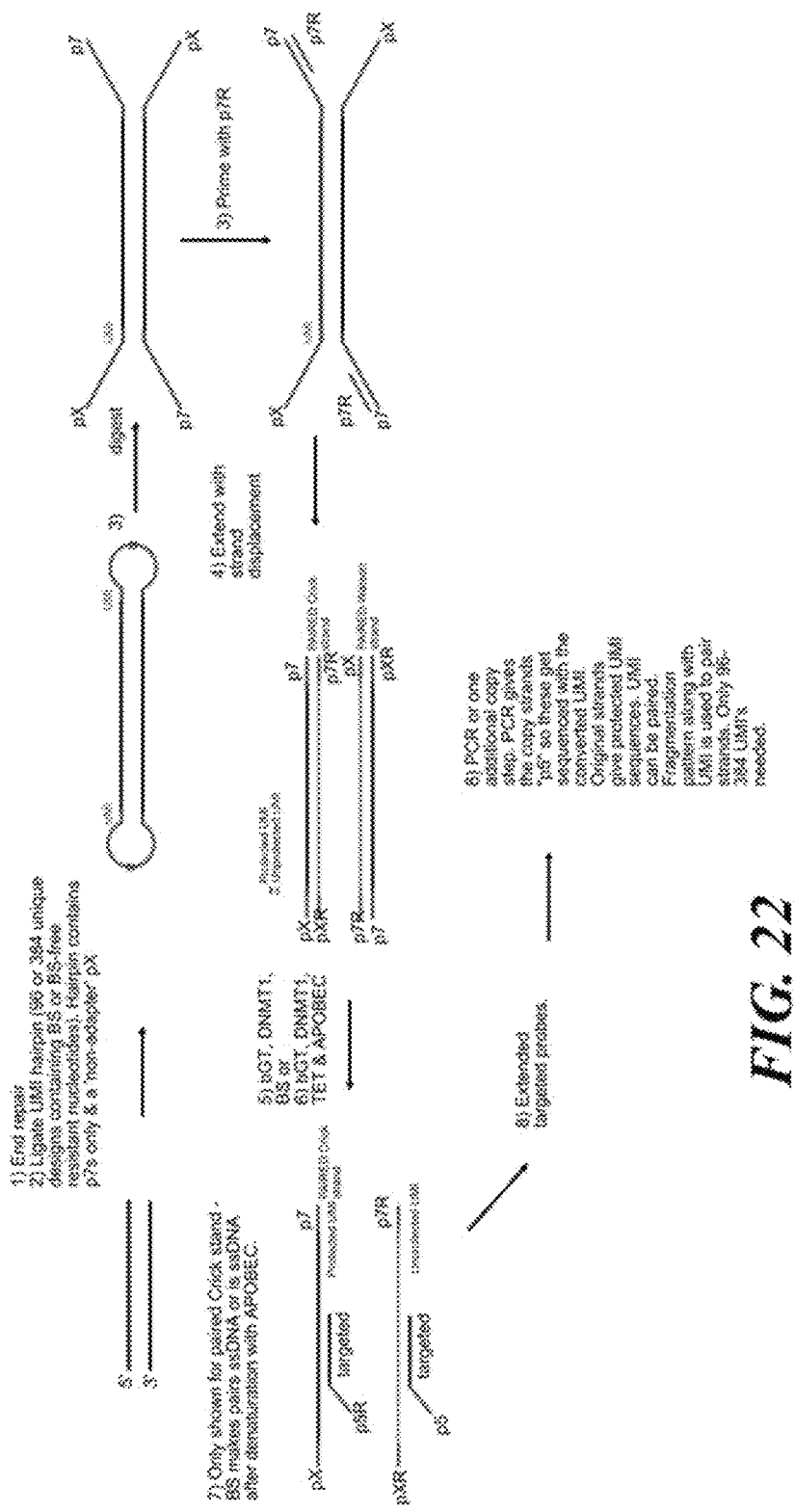
FIG. 22 shows a method of determining a value of a base of a polynucleotide comprising the use of unique molecular identifiers (UMIs), in accordance with embodiments.

In some cases, linkage between a first polynucleotide and a second polynucleotide can comprise informational linkage, for example, in the form of barcoding (e.g., as shown in FIG. 22). In some cases, one or more hairpin polynucleotide comprising a barcode (e.g., a unique molecular identifier, UMI) can be ligated to a forward polynucleotide and/or to a reverse polynucleotide (e.g., wherein the forward and/or reverse polynucleotide can be an original polynucleotide, which can be obtained from a sample). As shown in FIG. 22, a hairpin polynucleotide comprising a first UMI nucleic acid sequence at its 5' end and a second UMI nucleic acid sequence at its 3' end can be ligated to a double-stranded DNA polynucleotide comprising a forward and reverse polynucleotide. In some cases, the hairpin polynucleotide further comprises an adapter polynucleotide sequence (e.g., as shown in FIG. 22, wherein the hairpin polynucleotide comprises a p7 adapter sequence at the hairpins' 3' ends). A hairpin polynucleotide can further comprise a uracil residue between the 5' end of the hairpin polynucleotide and the 5' end of an adapter sequence (e.g., a p7 adapter, as shown in FIG. 22) comprised therein. In some cases, the hairpin polynucleotide can be cleaved (e.g., enzymatically, via digestion of a uracil residue of the hairpin polynucleotide with a mixture of enzymes that generate a single nucleotide gap where a uracil or deoxyuracil was present, such as, for example, the enzymes Uracil DNA Glycosylase (UDG) and Endonuclease VIII). Hairpin polynucleotide cleavage can result in a forward polynucleotide and a reverse polynucleotide of the double-stranded DNA polynucleotide comprising a barcode (e.g., UMI) at the forward and reverse polynucleotides' 3' and 5' ends, wherein the forward and reverse polynucleotides are no longer joined (e.g., linked) by a hairpin polynucleotide. A primer (e.g., an oligonucleotide comprising a p7R sequence) recognizing an adapter sequence (e.g., p7 adapter sequence) of a forward and/or reverse polynucleotide can be hybridized to the adapter sequence(s) and used to create an amplicon (e.g., a second polynucleotide) of the forward and/or reverse polynucleotide (e.g., using a strand-displacing PCR technique). In some cases, the amplicon(s) (e.g., second polynucleotide(s)) can comprise a barcode (e.g., UMI), for example, as a result of PCR extension using the forward or reverse polynucleotide as a template (e.g., wherein the forward or reverse polynucleotides comprise one or more barcodes, for example, at the 5' and/or 3' ends of the forward and/or reverse polynucleotides). In some cases, a barcode on the first polynucleotide (e.g., the forward and/or reverse polynucleotide) is a protected barcode (e.g., protected UMI, as shown in FIG. 22). In some cases, a barcode of the amplicon of the forward and/or reverse polynucleotide (e.g., the second polynucleotide) is unprotected. In some cases, the forward and/or reverse polynucleotide (e.g., the first polynucleotide) and the amplicon of the forward and/or reverse polynucleotide (e.g., the second polynucleotide) can be subjected to methods and/or individual operations of methods presented herein for processing a first and second polynucleotide (e.g., wherein the methods and/or individual operations of methods are useful for 5- or 6-letter sequencing techniques presented herein). In some cases, a sequencing adapter probe (e.g., a p5 or p5R sequencing adapter capable of hybridizing with a portion of the first or second polynucleotide, respectively, as shown in FIG. 22) can be used to extend (e.g., via PCR) the adapter probe. In some cases, an additional round of PCR or an additional copy operation is performed, for example, wherein the generated amplicon(s) comprise the p5 adapter sequence, which can be sequenced with converted UMIs (e.g., which may be converted during processing operations performed on unprotected UMIs) of the copy strands. The barcodes (UMIs) of the first and second polynucleotides and/or the copy strand(s) (e.g., which may comprise a read polynucleotide) can be paired. In some cases, a fragmentation pattern (e.g., of the forward and/or reverse polynucleotide(s) along with the UMI barcodes can be used to informationally link and/or pair the analyzed polynucleotide strands. In some cases, a relatively low number of barcodes (UMIs) is used to properly link polynucleotides informationally, e.g., as described herein.

Two-base sequencing methods, systems, and workflows presented herein can incorporate RNA analysis, for instance to attain improved accuracy and efficiency in RNA sequencing assays. In many cases, a first polynucleotide can be generated by contacting an RNA molecule (e.g., from a sample from a patient, such as a liquid biopsy or cell lysate sample) with a reverse transcriptase (or a biologically active fragment or derivative thereof) to generate a DNA molecule (e.g., a cDNA molecule). In some cases, use of RNA in the methods, systems, and compositions provided herein can allow insight into genetic and molecular details that DNA analysis may not provide, such as information into gene expression, DNA splicing in various physiological states (e.g., conditions) of a subject or tissue (e.g., alternate DNA splicing in disease states, especially those comprising a mutation).

In some cases, a Phred quality score can be calculated to assess the quality of base identification during the use of methods and systems provided herein. In some cases, Phred quality score calculation involves resolving the two Phred quality scores generated during two-base sequencing.

The methods and systems presented herein are compatible with, and offer significant benefits to accuracy and efficiency of, many types of sequencing. For example, Maxam-Gilbert sequencing, Sanger sequencing, or high-throughput sequencing (e.g., next generation sequencing (NGS)/second generation sequencing (e.g., short read sequencing) or third generation sequencing (e.g., long read sequencing) can be used in conjunction with the methods and systems disclosed herein.

Methods and systems presented herein (e.g., comprising two-base sequencing) can be useful in accurately determining (e.g., identifying) a mutation in a polynucleotide of a sample from a subject. As described herein, determining a mutation can comprise determining the identity of a base (e.g., adenine, cytosine, thymine, guanine, 5-methylcytosine, 5-hydroxymethylcytosine, a methylated cytosine (e.g., as opposed to adenine, thymine, guanine, or an unmethylated cytosine)), for example using a method of sequencing. In many cases, a condition (e.g., a physiological condition, such as a pathological condition (e.g., a disease state)) of a subject can be determined (e.g., diagnosed) at least in part based on the value (e.g., identity) of a base determined using a method, system, composition presented herein. In some cases, a condition of the subject is determined (e.g., diagnosed) based on a mutation determined at least in part based on a value (e.g., identity) of a base of a polynucleotide (e.g., from a sample obtained from a subject) determined using a method, system, and/or composition presented herein.

In some cases, the condition of the subject is (e.g., the presence or absence) of a neurodegenerative disease (or an increased or decreased risk for a neurodegenerative disease). In some embodiments, the neurodegenerative condition can be selected from Alzheimer's disease, frontotemporal dementia, amyotrophic lateral sclerosis, Parkinson's disease, spinocerebellar ataxia, spinal muscle atrophy, Lewy body dementia, or Huntington's disease.

In some cases, the condition of the subject is (e.g., the presence or absence of) a cancer or tumor. In some cases, the condition is selected from: a sarcoma, a glioma, an adenoma, leukemia, bladder cancer, breast cancer, colorectal cancer, endometrial cancer, kidney cancer, liver cancer, lung cancer, melanoma, non-Hodgkin lymphoma, pancreatic cancer, prostate cancer, thyroid cancer. In some cases, the condition is selected from: adenocarcinoma, adrenal gland cortical carcinoma, adrenal gland neuroblastoma, anus squamous cell carcinoma, appendix adenocarcinoma, bladder urothelial carcinoma, bile duct adenocarcinoma, bladder carcinoma, bladder urothelial carcinoma, bone chordoma, bone marrow leukemia lymphocytic chronic, bone marrow leukemia non-lymphocytic acute myelocytic, bone marrow lymph proliferative disease, bone marrow multiple myeloma, bone sarcoma, brain astrocytoma, brain glioblastoma, brain medulloblastoma, brain meningioma, brain oligodendroglioma, breast adenoid cystic carcinoma, breast carcinoma, breast ductal carcinoma in situ, breast invasive ductal carcinoma, breast invasive lobular carcinoma, breast metaplastic carcinoma, cervix neuroendocrine carcinoma, cervix squamous cell carcinoma, colon adenocarcinoma, colon carcinoid tumor, duodenum adenocarcinoma, endometrioid tumor, esophagus adenocarcinoma, esophagus and stomach carcinoma, eye intraocular melanoma, eye intraocular squamous cell carcinoma, eye lacrimal duct carcinoma, fallopian tube serous carcinoma, gallbladder adenocarcinoma, gallbladder glomus tumor, gastroesophageal junction adenocarcinoma, head and neck adenoid cystic carcinoma, head and neck carcinoma, head and neck neuroblastoma, head and neck squamous cell carcinoma, kidney chromophore carcinoma, kidney medullary carcinoma, kidney renal cell carcinoma, kidney renal papillary carcinoma, kidney sarcomatoid carcinoma, kidney urothelial carcinoma, kidney carcinoma, leukemia lymphocytic, leukemia lymphocytic chronic, liver cholangiocarcinoma, liver hepatocellular carcinoma, liver carcinoma, lung adenocarcinoma, lung adenosquamous carcinoma, atypical lung carcinoid, lung carcinosarcoma, lung large cell neuroendocrine carcinoma, lung non-small cell lung carcinoma, lung sarcoma, lung sarcomatoid carcinoma, lung small cell carcinoma, lung small cell undifferentiated carcinoma, lung squamous cell carcinoma, upper aerodigestive tract squamous cell carcinoma, upper aerodigestive tract carcinoma, lymph node lymphoma diffuse large B cell, lymph node lymphoma follicular lymphoma, lymph node lymphoma mediastinal B-cell, lymph node lymphoma plasmablastic lung adenocarcinoma, lymphoma follicular lymphoma, lymphoma, non-Hodgkins, nasopharynx and paranasal sinuses undifferentiated carcinoma, ovary carcinoma, ovary carcinosarcoma, ovary clear cell carcinoma, ovary epithelial carcinoma, ovary granulosa cell tumor, ovary serous carcinoma, pancreas carcinoma, pancreas ductal adenocarcinoma, pancreas neuroendocrine carcinoma, peritoneum mesothelioma, peritoneum serous carcinoma, placenta choriocarcinoma, pleura mesothelioma, prostate acinar adenocarcinoma, prostate carcinoma, rectum adenocarcinoma, rectum squamous cell carcinoma, skin adnexal carcinoma, skin basal cell carcinoma, skin melanoma, skin Merkel cell carcinoma, skin squamous cell carcinoma, small intestine adenocarcinoma, small intestine gastrointestinal stromal tumors (GISTs), large intestine/colon carcinoma, large intestine adenocarcinoma, soft tissue angiosarcoma, soft tissue Ewing sarcoma, soft tissue hemangioendothelioma, soft tissue inflammatory myofibroblastic tumor, soft tissue leiomyosarcoma, soft tissue liposarcoma, soft tissue neuroblastoma, soft tissue paraganglioma, soft tissue perivascular epitheliod cell tumor, soft tissue sarcoma, soft tissue synovial sarcoma, stomach adenocarcinoma, stomach adenocarcinoma diffuse-type, stomach adenocarcinoma intestinal type, stomach adenocarcinoma intestinal type, stomach leiomyosarcoma, thymus carcinoma, thymus thymoma lymphocytic, thyroid papillary carcinoma, unknown primary adenocarcinoma, unknown primary carcinoma, unknown primary malignant neoplasm, lymphoid neoplasm, unknown primary melanoma, unknown primary sarcomatoid carcinoma, unknown primary squamous cell carcinoma, unknown undifferentiated neuroendocrine carcinoma, unknown primary undifferentiated small cell carcinoma, uterus carcinosarcoma, uterus endometrial adenocarcinoma, uterus endometrial adenocarcinoma endometrioid, uterus endometrial adenocarcinoma papillary serous, and uterus leiomyosarcoma Also provided herein are methods that comprise a PCR free workflow. Such methods can be employed to differentiate and identify cytosine, mC, and hmC in a DNA sequence. A non-limiting example of incorporating a PCR free method into a workflow that can be incorporated or combined with a method provided herein is described in (McInroy GR, Beraldi D, Raiber E-A, Modrzynska K, van Delft P, Billker O, et al. (2016) Enhanced Methylation Analysis by Recovery of Unsequenceable Fragments. PLoS ONE 11(3): e0152322. doi.org), which is incorporated by reference herein in its entirety, and is illustrated in the left panel of FIG. 17. Such a method can employ use of a biotin tag and can comprise denaturation of a DNA strand after operations of a method provided herein, as depicted in the right panel of FIG. 17.

Herein, a nucleic acid molecule such as DNA can comprise guanine, (G), adenine (A), thymine (T), uracil (U), cytosine (C), or bases that are capable of base pairing reliably with a complementary nucleotide. 7-deaza-adenine, 7-deaza-guanine, adenine, guanine, cytosine, thymine, uracil, 2-deaza-2-thio-guanosine, 2-thio-7-deaza-guanosine, 2-thio-adenine, 2-thio-7-deaza-adenine, isoguanine, 7-deaza-guanine, 5,6-dihydrouridine, 5,6-dihydrothymine, xanthine, 7-deaza-xanthine, hypoxanthine, 7-deaza-xanthine, 2,6 diamino-7-deaza purine, 5-methyl-cytosine, 5-hydroxymethylcytosine, 5-propynyl-uridine, 5-propynyl-cytidine, 2-thio-thymine or 2-thio-uridine are examples of such bases. An oligonucleotide can comprise an LNA, a PNA, a UNA, or an morpholino oligomer, for example. The oligonucleotides used herein may contain natural or non-natural nucleotides or linkages.

In an aspect, the present disclosure provides a method for identifying a cytosine base. The method comprises: a) deaminating a cytosine base of a double-stranded polynucleotide in a presence of a helicase to yield a deaminated cytosine base; b) sequencing at least a portion of the double-stranded polynucleotide comprising the deaminated cytosine base or double-stranded derivative thereof to obtain sequencing data; and c) processing the sequencing data to identify the cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some embodiments, the sequencing comprises sequencing at least a portion of both strands of the double-stranded polynucleotide or double-stranded derivative thereof.

In some embodiments, the deaminating is performed with a deaminase. In some embodiments, where the deaminase is an apolipoprotein B mRNA editing enzyme, catalytic polypeptide-like (APOBEC) enzyme, or a fragment thereof. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is UvrD helicase, *Geobacillus sterothermophilus* Bad protein, a PcrA helicase, or a fragment thereof.

In some embodiments, the method further comprises, subjecting the double-stranded polynucleotide comprising the deaminated cytosine base to one or more reactions to generate the double-stranded derivative thereof, where (c) comprises sequencing at least a portion of the double-stranded derivative thereof to obtain the sequencing data. In some embodiments, the method further comprises providing a sample double-stranded polynucleotide comprising a forward strand and a reverse strand.

In some embodiments, the method further comprises, separating the forward strand from the reverse strand. In some embodiments, the method further comprises using the forward strand in a nucleic acid extension reaction to generate the double-stranded polynucleotide. In some embodiments, the deaminating is performed with a deaminase. In some embodiments, where the deaminase is an apolipoprotein B mRNA editing enzyme, catalytic polypeptide-like (APOBEC) enzyme, or a fragment thereof. In some embodiments, the helicase comprises an amino acid sequence that is at least about 70%, at least about 75%, at least about 80%, at least about 85%, at least about 90%, at least about 93%, at least about 95%, at least about 97%, at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In some embodiments, the cytosine base is a methylcytosine base or a hydroxymethyl cytosine base. In some embodiments, the method further comprises subjecting the double-stranded polynucleotide comprising the deaminated cytosine base to one or more reactions to generate the double-stranded derivative thereof, where (c) comprises sequencing at least a portion of the double-stranded derivative thereof to obtain the sequencing data. In some embodiments, (c) comprises processing the sequencing data to identify the cytosine base as a cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In some embodiments, the forward strand comprises a methylated cytosine base and the method further comprises using the forward strand in a nucleic acid extension reaction that generates a modified double-stranded polynucleotide comprising (i) the forward strand comprising the methylated cytosine base and (ii) an additional reverse strand comprising the cytosine base. In some embodiments, the method further comprises, converting the methylated cytosine base to glucosylated hydroxymethylcystosine.

In some embodiments, the methylated cytosine base is a methylcytosine base and the converting comprises subjecting the methylcytosine base to oxidation conditions to generate a hydroxymethylcytosine base and subjecting the hydroxymethylcytosine base to glucosylation conditions to generate the glucosylated hydroxymethylcytosine. In some embodiments, the methylated cytosine base is hydoxymethylcytosine and the converting comprises subjecting the hydroxymethylcytosine base to glucosylation conditions to generate the glucosylated hydroxymethylcytosine.

In some embodiments, the deaminating is performed with a deaminase. In some embodiments, the deaminase is an apolipoprotein B mRNA editing enzyme, catalytic polypeptide-like (APOBEC) enzyme, or a fragment thereof. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence to UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In some embodiments, the method further comprises, subjecting the double-stranded polynucleotide comprising the deaminated cytosine base to one or more reactions to generate the double-stranded derivative thereof, where (c) comprises sequencing at least a portion of the double-stranded derivative thereof to obtain the sequencing data. In some embodiments, the method further comprises processing the sequencing data to identify the methylated cytosine base as a methylated cytosine base with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In another aspect, the present disclosure provides a method for identifying a cytosine base. The method comprises: a) deaminating a cytosine base of a double-stranded polynucleotide, in a presence of a helicase, with a deaminase to yield a deaminated cytosine base; b) sequencing at least a portion of the double-stranded polynucleotide comprising the deaminated cytosine base or double-stranded derivative thereof to obtain sequencing data; and c) processing the sequencing data to identify the cytosine base.

In some embodiments, the sequencing comprises sequencing at least a portion of both strands of the double-stranded polynucleotide or double-stranded derivative thereof. In some embodiments, the deaminase is an apolipoprotein B mRNA editing enzyme, catalytic polypeptide-like (APOBEC) enzyme, or a fragment thereof. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In some embodiments, the method further comprises, providing a sample double-stranded polynucleotide comprising a forward strand and a reverse strand. In some embodiments, the method further comprises, separating the forward strand from the reverse strand. In some embodiments, the separating comprises subjecting the forward strand to a nucleic acid extension reaction that generates the double-stranded polynucleotide. In some embodiments, the deaminase is an apolipoprotein B mRNA editing enzyme, catalytic polypeptide-like (APOBEC) enzyme, or a fragment thereof. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In some embodiments, the cytosine base is a methylcytosine base or a hydroxymethyl cytosine base. In some embodiments, the method further comprises, subjecting the double-stranded polynucleotide comprising the deaminated cytosine base to one or more reactions to generate the double-stranded derivative thereof, where (c) comprises sequencing at least a portion of the double-stranded derivative thereof to obtain the sequencing data. In some embodiments, the forward strand comprises a methylated cytosine base and the separating comprises using the forward strand in a nucleic acid extension reaction that generates a modified double-stranded polynucleotide comprising (i) the forward strand comprising the methylated cytosine base and (ii) an additional reverse strand comprising the cytosine base. In some embodiments, the method further comprises, converting the methylated cytosine base to glucosylated hydroxymethylcystosine. In some embodiments, the methylated cytosine base is a methylcytosine base and the converting comprises subjecting the methylcytosine base to oxidation conditions to generate a hydroxymethylcytosine base and subjecting the hydroxymethylcytosine base to glucosylation conditions to generate the glucosylated hydroxymethylcytosine. In some embodiments, the methylated cytosine base is hydoxymethylcytosine and the converting comprises subjecting the hydroxymethylcytosine base to glucosylation conditions to generate the glucosylated hydroxymethylcytosine.

In some embodiments, the deaminase is an apolipoprotein B mRNA editing enzyme, catalytic polypeptide-like (APOBEC) enzyme, or a fragment thereof. In some embodiments, the helicase comprises an amino acid sequence of at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof. In some embodiments, the method further comprises, subjecting the double-stranded polynucleotide comprising the deaminated cytosine base to one or more reactions to generate the double-stranded derivative thereof, where (c) comprises sequencing at least a portion of the double-stranded derivative thereof to obtain the sequencing data.

An additional aspect of the disclosure provides a kit. The kit can comprise a deaminase; a helicase; and packaging and instructions therein to use the kit. In some embodiments, the deaminase is an apolipoprotein B mRNA editing enzyme, catalytic polypeptide-like (APOBEC) enzyme, or a fragment thereof. In some embodiments, the kit further comprises a methylcytosine dioxygenase. In some embodiments, the methylcytosine dioxygenase comprises a ten eleven translocation (TET) enzyme or fragment thereof. In some embodiments, the TET enzyme is TET1, TET2 or TET3. In some embodiments, the kit further comprises a deoxyribonucleic acid (DNA) glucosyltransferase. In some embodiments, the DNA glucosyltransferase comprises DNA beta-glucosyltransferase. In some embodiments, the kit further comprises a DNA methyltransferase. In some embodiments, the DNA methyltransferase comprises DNA methyltransferase 1 (DNMT1). In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In another aspect, the present disclosure provides a method for identifying a cytosine base. The method comprises: a) contacting a polynucleotide comprising a cytosine base with one or more reagents that collectively transform the cytosine base to an altered base derived from the cytosine base, thereby generating a modified polynucleotide comprising the altered base; b) sequencing at least a portion of the modified polynucleotide comprising the altered base or derivative thereof to obtain sequencing data with a coverage of no more than 30-fold, of no more than 25-fold, of no more than 20-fold, of no more than 15-fold, or no more than 10-fold, of no more than 5-fold, or of no more than 2-fold; and c) processing the sequencing data to identify the cytosine base as cytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In some embodiments, the modified polynucleotide or derivative thereof is a double-stranded polynucleotide. In some embodiments, the sequencing comprises sequencing at least a portion of both strands of the double-stranded polynucleotide. In some embodiments, the cytosine base is a methylated cytosine base. In some embodiments, the method further comprises processing the sequencing data to identify the methylated base as cytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In some embodiments, the one or more reagents comprise an oxidizing agent. In some embodiments, the oxidizing agent comprises a ten eleven translocation (TET) enzyme or fragment thereof. In some embodiments, the TET enzyme is TET1, TET2 or TET3. In some embodiments, the one or more reagents comprise a DNA-glucosyltransferase. In some embodiments, the one or more reagents comprise a deaminase. In some embodiments, the deaminase is an apolipoprotein B mRNA editing enzyme, catalytic polypeptide-like (APOBEC) enzyme, or a fragment thereof. In some embodiments, the one or more reagents comprise a helicase. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof. In some embodiments, the one or more reagents comprise a DNA methyltransferase.

In some embodiments, the method further comprises, providing a sample double-stranded polynucleotide comprising a forward strand comprising the polynucleotide and a reverse strand. In some embodiments, the method further comprises, separating the forward strand from the reverse strand. In some embodiments, the separating comprises using the forward strand in a nucleic acid extension reaction that generates a double-stranded polynucleotide comprising the polynucleotide.

In some embodiments, the methylated base is a methylated cytosine base. In some embodiments, the one or more reagents comprise a deaminase and a helicase. In some embodiments, the helicase comprises an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

In some embodiments, the sequencing comprises sequencing at least a portion of both strands of the double-stranded polynucleotide or double-stranded derivative thereof. In some embodiments, the sequencing data to identify the methylated cytosine base as cytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

In some embodiments, the polynucleotide is derived from population of polynucleotides, and where a base frequency of the methylated cytosine base in the population of polynucleotides is less than or equal to 75%, less than or equal to 70%, less than or equal to 65%, less than or equal to 60%, less than or equal to 55%, less than or equal to 50%, less than or equal to 45%, less than or equal to 40%, less than or equal to 35%, less than or equal to 30%, less than or equal to 25%, less than or equal to 20%, less than or equal to 15%, less than or equal to 10%, less than or equal to 7%, less than or equal to 5%, less than or equal to 3%, or less than or equal to 1% or lower at a given locus.

In some embodiments, the methylated cytosine base comprises a methylcytosine base or a hydroxymethylcytosine base. In some embodiments, the methylated cytosine base comprises a methylcytosine base and the one or more reagents comprise an oxidating agent, a DNA glucosyltransferase, a deaminase and a helicase, including examples of such reagents provided elsewhere herein. In some embodiments, the methylated cytosine base comprises a hydroxymethylcytosine base and the one or more reagents comprise an oxidating agent, a DNA glucosyltransferase, a methyltransferase, a deaminase and a helicase, including examples of such reagents provided elsewhere herein. In some embodiments, the sequencing comprises sequencing at least a portion of both strands of the double-stranded polynucleotide or double-stranded derivative thereof.

In some embodiments, processing the sequencing data to identify the methylated cytosine base as methylcytosine or hydroxymethylcytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. In some embodiments, the method further comprises, processing the sequencing data to identify the methylated cytosine base as methylcytosine or hydroxymethylcytosine with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

Compositions described herein can be utilized in methods described herein to both detect and identify a base at a given locus and also detect and identify the methylation or other modification status of the base. For example, methods described herein can be implemented to identify a base at a given locus with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy. Moreover, methods described herein can be implemented identify a methylated (e.g., methylated cytosine, such as methylcytosine, hydroxymethylcytosine) or other modified base as methylated or otherwise modified with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

Compositions described herein can be utilized in methods described herein to detect and identify the methylation or other modification status of the base, with a sequencing coverage of no more than 30-fold, of no more than 25-fold, of no more than 20-fold, of no more than 15-fold, or no more than 10-fold, of no more than 5-fold, or of no more than 2-fold with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

As described elsewhere herein, methods and compositions described can be useful in detecting modified (e.g., methylated cytosine bases, including methylcytosine and hydroxymethyl cytosine) bases at relatively low frequency at a locus in a population of nucleic acids at high accuracy. Such methylated bases can occur at relatively rare frequencies at a given locus. In some embodiments, a modified base that is detected and identified has a base frequency at a given locus in a population of polynucleotides of less than or equal to 75%, less than or equal to 70%, less than or equal to 65%, less than or equal to 60%, less than or equal to 55%, less than or equal to 50%, less than or equal to 45%, less than or equal to 40%, less than or equal to 35%, less than or equal to 30%, less than or equal to 25%, less than or equal to 20%, less than or equal to 15%, less than or equal to 10%, less than or equal to 7%, less than or equal to 5%, less than or equal to 3%, or less than or equal to 1% or lower. Such a modified base can be detected and identified with an accuracy of at least about 50%, at least about 55%, at least about 60%, at least about 65%, at least about 70%, at least about 75%, at least about 80%, at least about 85%, at least about 90%, at least about 95%, at least about 99%, at least about 99.9%, at least about 99.99%, at least about 99.999%, at least about 99.9999% or greater accuracy.

Methods described herein may employ a helicase, including in combination with a deaminase in a deamination operation. Such a helicase may comprise an amino acid sequence that is at least about 70%, at least about 75%, at least about 80%, at least about 85%, at least about 90%, at least about 93%, at least about 95%, at least about 97%, or at least about 99% homologous to the amino acid sequence of UvrD helicase, *Geobacillus sterothermophilus* Bad protein, a PcrA helicase, or a fragment thereof. In some embodiments, the helicase is a UvrD helicase, *Geobacillus sterothermophilus* Bad protein, a PcrA helicase, or a fragment thereof.

Methods described herein may employ a deaminase. In some cases, the deaminase is a cytidine deaminase. The cytosine deaminase can be an apolipoprotein B mRNA editing enzyme, catalytic polypeptide-like (APOBEC) enzyme (e.g., APOBEC3A), or a fragment thereof.

EXAMPLES

Example 1: Preparation of a Polynucleotide for Two-Base Sequencing

This example shows a method of preparing a polynucleotide for sequencing using a hairpin double-stranded DNA construct. For analysis of cell-free DNA (cfDNA), a 10 milliliter (ml) sample of peripheral blood is drawn from a patient and centrifuged at 2000×g for 15 minutes, and the plasma fraction comprising cfDNA is collected. A hairpin polynucleotide comprising a 50 bp targeting sequence complementary to the 3' end of a cfDNA polynucleotide of interest (e.g., first polynucleotide) and a 3' sequencing adapter comprising a 50 bp targeting sequence complementary to the 5' end of the cfDNA polynucleotide of interest are mixed with the collected cfDNA and used to capture the cfDNA polynucleotide. A 5' sequencing adapter is hybridized to a portion of the 3' sequencing adapter overhanging the 5' end of the cfDNA, and sulfolobus DNA polymerase IV is used to fill gaps between the 5' sequencing adapter and the cfDNA polynucleotide. DNA polymerase is used to create a second polynucleotide using the 3' end of the hairpin polynucleotide as a primer and the cfDNA polynucleotide (e.g., the first polynucleotide as a template) (e.g., as shown in FIG. 5).

If genomic DNA is used, double-stranded DNA polynucleotide (comprising a forward polynucleotide and a reverse polynucleotide) is extracted from a cellular sample and fragmented. Tagmentation of genomic DNA is performed using Tn5 transposase and hairpin polynucleotides comprising Tn5 transposase binding sites at the 5' and 3' ends of the hairpin to form double-stranded DNA polynucleotides comprising two hairpin polynucleotides and two first polynucleotides (e.g., a forward polynucleotide and a reverse polynucleotide) (e.g., as shown in FIG. 10). Alternatively, hairpin polynucleotides are ligated directly to a double-stranded DNA polynucleotide comprising hybridized first polynucleotides to form double-stranded DNA polynucleotides comprising two hairpin polynucleotides (e.g., as shown in FIG. 19A or operations 1001 and 1002 of FIG. 19B).

Figures 19A, 19B:
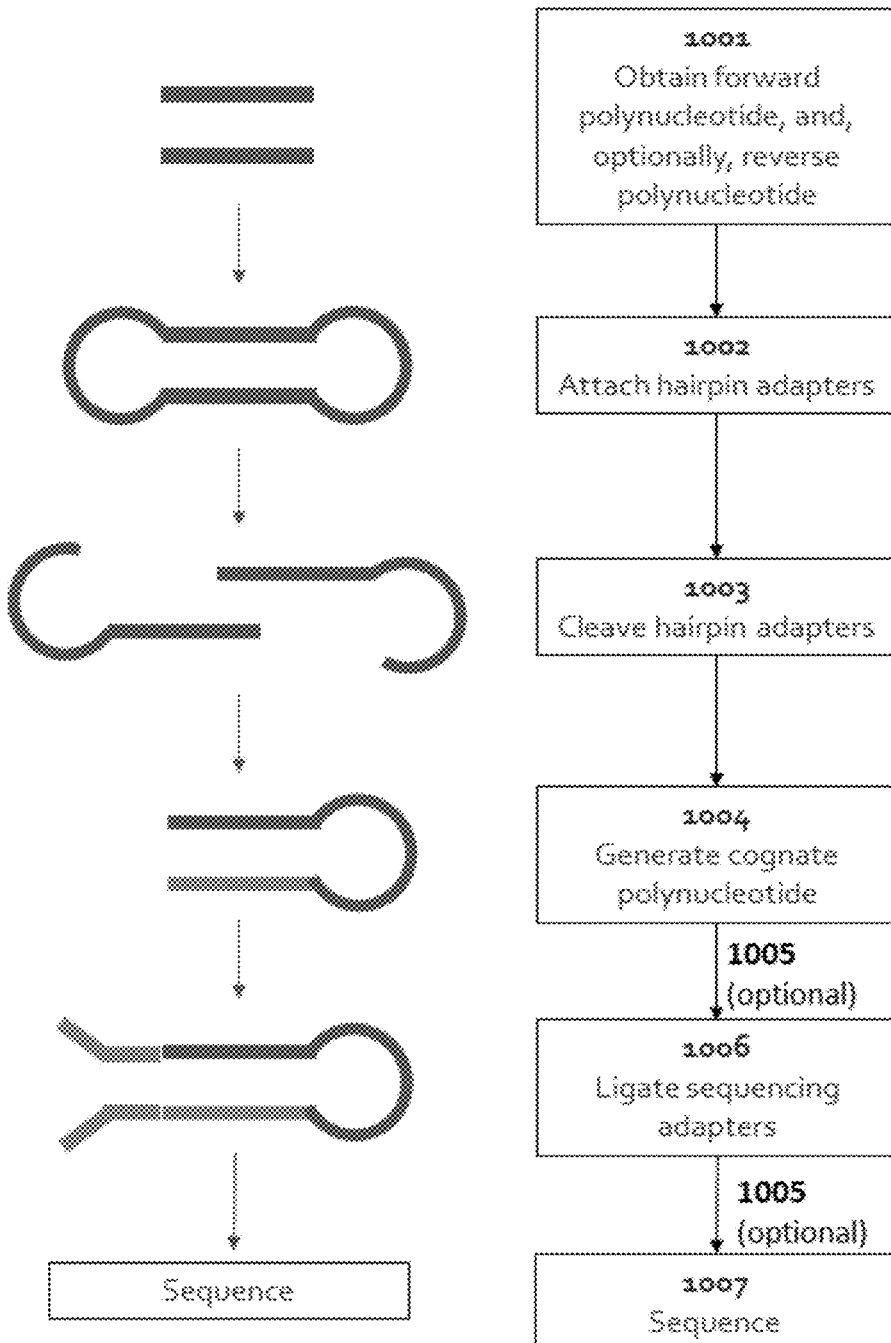
FIGS. 19A-19E show operations for identifying a base in a polynucleotide, in accordance with embodiments.
Figure 19C:
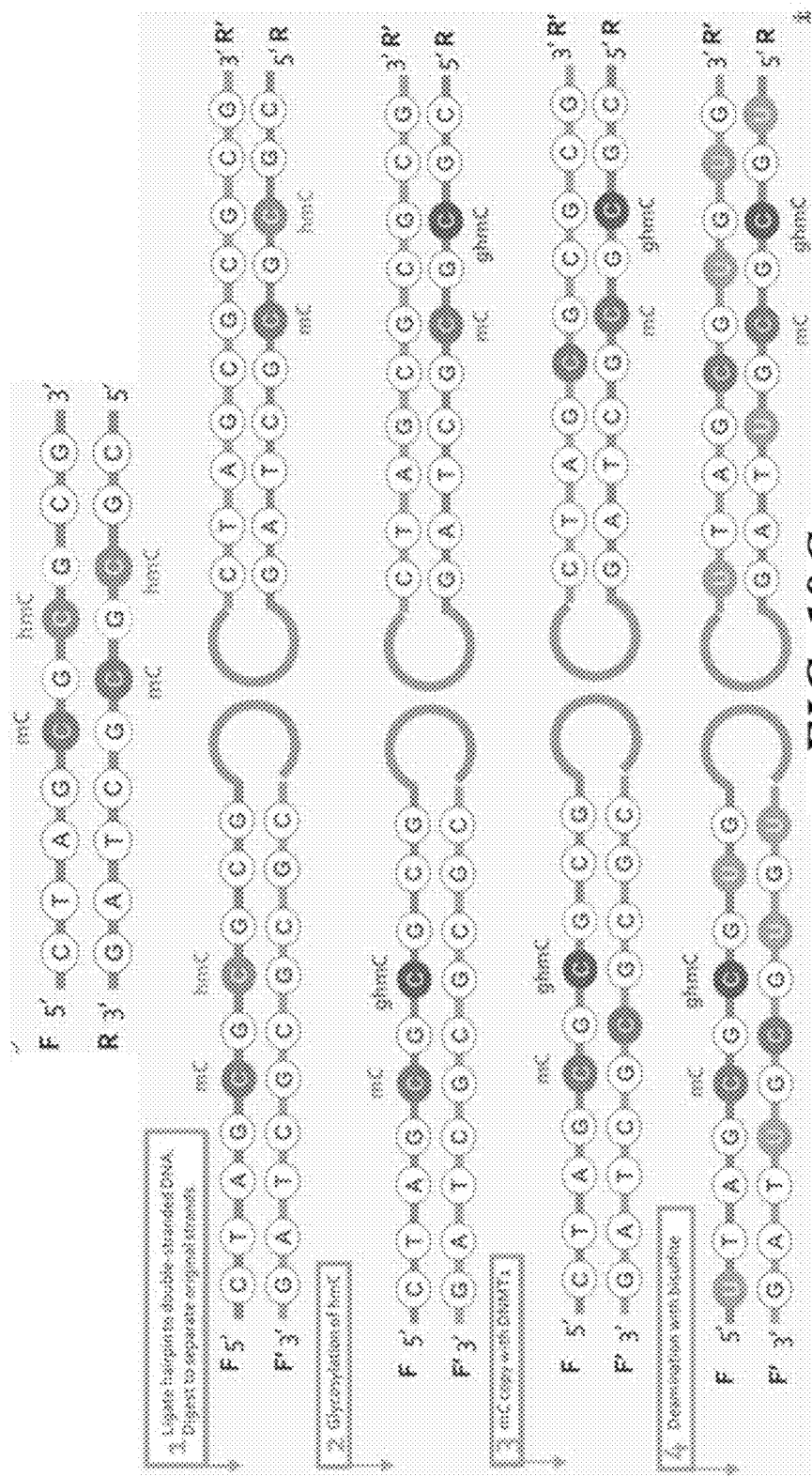

Double-stranded polynucleotides are enzymatically cleaved at the 3' end of the hairpin polynucleotide to yield two polynucleotides comprising a first polynucleotide (e.g., a forward polynucleotide and a reverse polynucleotide, respectively) and a hairpin polynucleotide (e.g., as shown in FIG. 19A or operation 1003 of FIG. 19B, or operation 1 of FIG. 19C). A second polynucleotide (e.g., a cognate polynucleotide) is generated by performing polymerase chain reaction using the free 3' end of the hairpin polynucleotide as a primer and the first polynucleotide as a template (e.g., as shown in FIG. 19A, operation 1004 of FIG. 19B, and operation 1 of FIG. 19C). Sequencing adapters are then ligated to the 5' end of the first polynucleotide and the 3' end of the second polynucleotide before chemical processing (e.g., as presented in Examples 3-11, FIG. 1B, and operations 1005 and 1006 of FIG. 19B). Alternatively, sequencing adapters are ligated to the 5' end of the first polynucleotide and the 3' end of the second polynucleotide after chemical processing (e.g., as presented in Examples 3-11, FIG. 1A, operations 1005 and 1006 of FIG. 19B, and operations 2-4 of FIG. 19C).

Figure 19D:
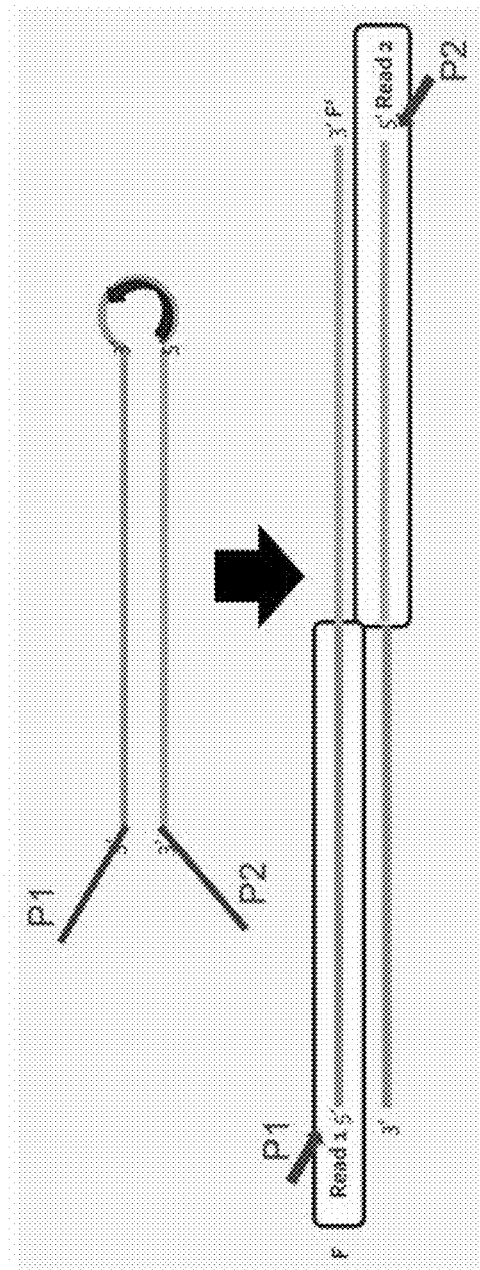

Double-stranded polynucleotides comprising a hairpin polynucleotide, a first polynucleotide (e.g., forward or reverse polynucleotide), a second polynucleotide (e.g., cognate polynucleotide), and 5' and 3' sequencing adapters can be opened by melting. In some cases, a first polynucleotide of a double-stranded polynucleotide (e.g., with or without a hairpin polynucleotide) can be separated enzymatically, e.g., using a helicase. The first and second polynucleotides can be subjected to polymerase chain reaction on the opened construct to generate a polynucleotide comprising a polynucleotide (e.g., read polynucleotide) complementary to the second polynucleotide (e.g., as shown in FIG. 19D). The first polynucleotide (e.g., read 1) and read polynucleotide (e.g., read 2) are sequenced to determine values (e.g., identities) for a first base at a locus of the first polynucleotide and for a second base at or proximal to (e.g., in an adjacent position in the sequence of the polynucleotide relative to) a corresponding locus of the second polynucleotide. A value for the true base present in the cfDNA or genomic DNA at the locus is determined using a computer program based on the determined first and second bases (e.g., using one of the tables shown in FIGS. 20A-F).

Example 2: Two-Base Sequencing with 4-Letter Base Discrimination

This example shows the use of two-base sequencing comprising evaluation of a base of a cfDNA molecule using a 4-letter base discrimination sequencing assay.

A double-stranded DNA polynucleotide comprising a first polynucleotide (which comprises a cell-free DNA original polynucleotide), a second polynucleotide, and adapter polynucleotides ligated to the 5' and 3' ends of the first and second polynucleotides is sequenced using next generation sequencing.

Alternatively, double-stranded DNA polynucleotide comprising a first polynucleotide (e.g., which comprises a cell-free DNA original polynucleotide), a second polynucleotide, a hairpin polynucleotide, and adapter polynucleotides is provided as described in Example 1. The double-stranded DNA polynucleotide is opened by heating to its melting temperature, and the first polynucleotide and the second polynucleotide are sequenced. Separation of the first and second polynucleotides of the double-stranded DNA polynucleotide can be improved by contacting the double-stranded DNA polynucleotide with an intercalating agent, a single-stranded DNA binding protein, and/or a helicase, in addition to or in place of heating the double-stranded DNA polynucleotide.

A value for the true base at a locus of the first polynucleotide and error calling are determined using a computer to process sequencing data according to the table found in FIG. 20A, wherein the "F strand" and "F" values represent a determined value of a base of the first polynucleotide at the locus and the "F' strand" and "F'" values represent a determined value of a base of the second polynucleotide at the corresponding locus on the second polynucleotide.

Example 3: Two-Base Sequencing with 5-Letter Base Discrimination Comprising Bisulfite Treatment This example shows the use of two-base sequencing comprising evaluation of a base of a cfDNA molecule using a 5-letter base discrimination (adenine, guanine, thymine, cytosine, and methylated cytosine bases) sequencing assay and bisulfite conversion.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA polynucleotide is treated with bisulfite before it is opened by heating to its melting temperature, and the first polynucleotide and the second polynucleotide are sequenced.

A value for the true base at a locus of the first polynucleotide and error calling are determined using a computer to process sequencing data according to the table found in FIG. 20B, wherein the "F strand" and "F" values represent a determined value of a base of the first polynucleotide at the locus and the "F' strand" and "F'" values represent a determined value of a base of the second polynucleotide at the corresponding locus on the second polynucleotide.

Example 4: Two-Base Sequencing Comprising Oxidative Bisulfite Treatment

This example shows the use of oxidative bisulfite treatment in two-base sequencing for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The population of provided double-stranded DNA polynucleotides (comprising the first and second polynucleotides) is divided into two groups: a first group is exposed to the oxidizing agent potassium ruthenate, and the second group is not exposed to an oxidizing agent. Both groups of double-stranded DNA polynucleotides are then sequenced using bisulfite sequencing.

Data is screened for errors prior to alignment using a computer to process sequencing data according to the table found in FIG. 20C, wherein the "F strand" and "F" values represent a determined value of a base of the first polynucleotide at the locus and the "F' strand" and "F'" values represent a determined value of a base of the second polynucleotide at the corresponding locus on the second polynucleotide, yielding higher confidence in determined values for the base at the locus of the first polynucleotide than oxidative bisulfite sequencing. A value for the true base at a locus of the first polynucleotide is determined using oxidative bisulfite sequencing methods (e.g., using differential analysis of reads from the first group and the second group to determine the presence of 5-hydroxymethylcytosine and using the sequencing data from the second group to determine the presence of 5-methylcytosine).

Alternatively, the population of double-stranded DNA polynucleotides is not divided into groups, and all of the double-stranded DNA is contacted with the oxidizing agent (potassium ruthenate) before being subjected to bisulfite sequencing. Data is screened for errors prior to alignment using a computer to process sequencing data according to the table found in FIG. 20C, wherein 5-methylcytosine, adenine, guanine, and thymine are distinguished from one another and from a fifth group of bases, which may be cytosine or 5-hydroxymethylcytosine (e.g., 5-letter sequencing).

Example 5: Two-Base Sequencing with 6-Letter Base Discrimination Comprising Treatment with Potassium Ruthenate This example shows the use of potassium ruthenate treatment in two-base sequencing for determining a value of a base in an original polynucleotide of a sample.

Figure 2C:
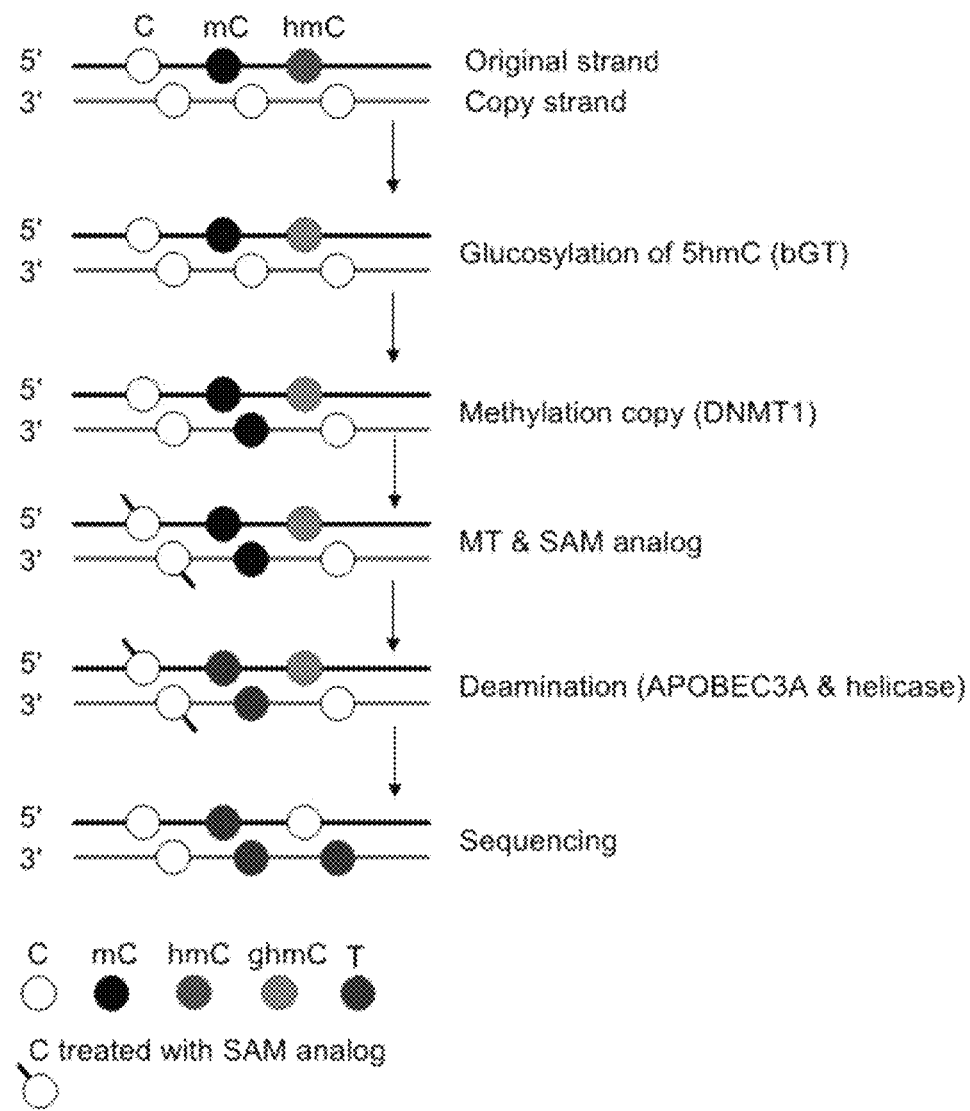
Figure 2D:
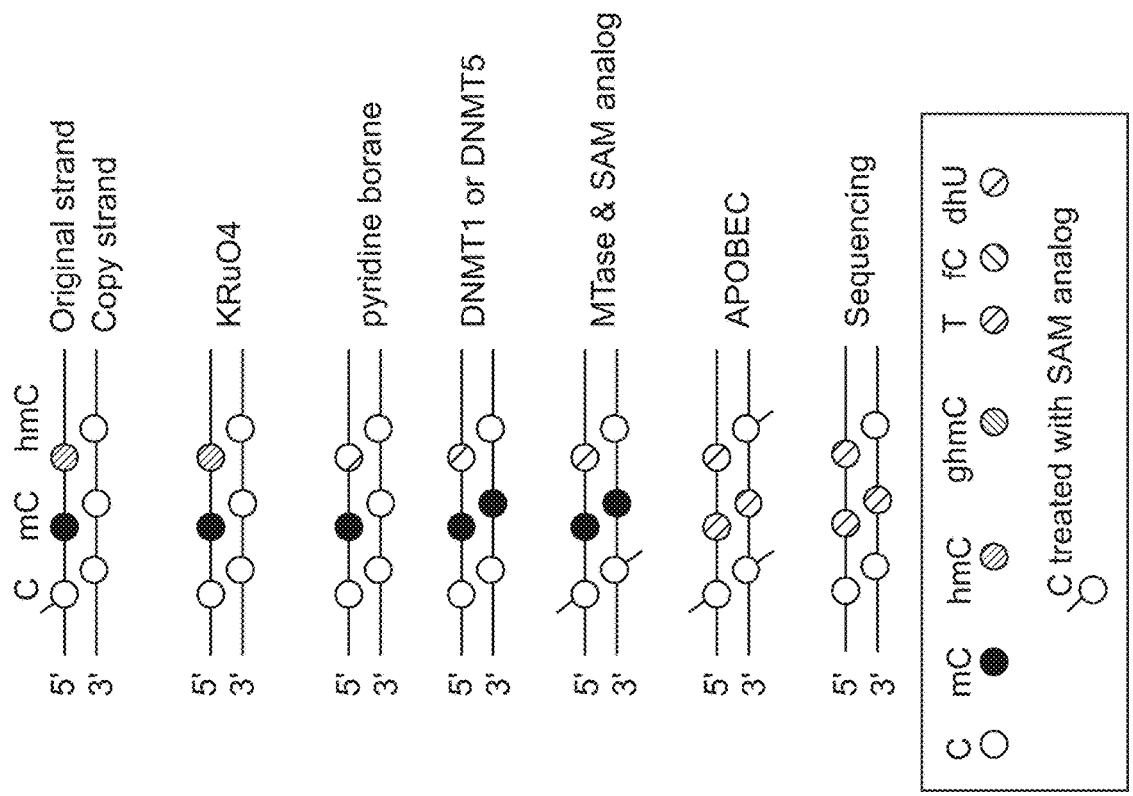
Figure 2D:
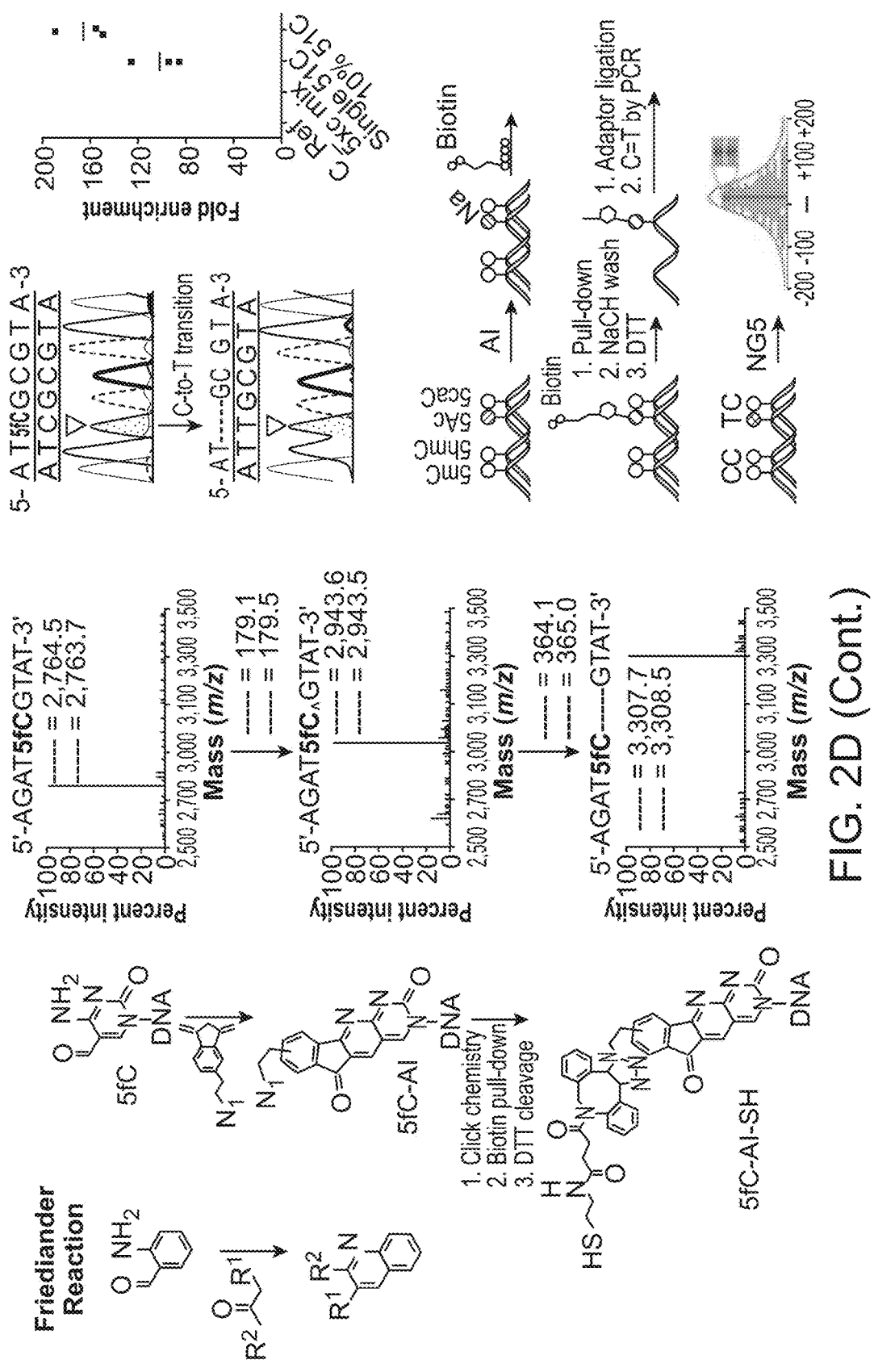

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA polynucleotide (comprising the first and second polynucleotides) is exposed to the oxidizing agent potassium ruthenate (e.g., as shown in FIG. 2D). Then the double-stranded DNA is exposed to the reducing agent pyridine borane. The double-stranded DNA is then exposed to DNMT1. In some cases, DNMT5 is substituted for DNMT1 at this operation. The double-stranded DNA is exposed to a solution comprising an engineered DNA methyltransferase and a SAM analog. The double-stranded DNA is then separated using a helicase (or single-stranded DNA-binding protein) and deaminated using APOBEC3A. A read polynucleotide is generated using PCR while the double-stranded DNA is separated, and the first polynucleotide and read polynucleotide are sequenced. Strand-displacing PCR reagents and/or heating can be used to separate the first and second polynucleotides to perform PCR in cases where the helicase is no longer present/active.

A value for the true base at a locus of the first polynucleotide and error calling are determined using a computer to process sequencing data according to the table found in FIG. 20D, wherein the "F strand" and "F" values represent a determined value of a base of the first polynucleotide at the locus and the "F' strand" and "F'" values represent a determined value of a base of the second polynucleotide at the corresponding locus on the second polynucleotide.

Example 6: Two-Base Sequencing with 6-Letter Base Discrimination Comprising TET Treatment This example shows an alternate method comprising the use of TET treatment in two-base sequencing for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA polynucleotide (comprising the first and second polynucleotides) is exposed to the oxidizing agent potassium ruthenate (e.g., as shown in FIG. 3). The double-stranded DNA is then exposed to DNMT1. The double-stranded DNA is exposed to a solution comprising the oxidizing agent TET. In some cases, a biologically active fragment of TET can be used. The double-stranded DNA is then exposed to pic-borane before hairpin polynucleotides are melted, a read polynucleotide is generated using PCR, and the first polynucleotide and read polynucleotide are sequenced.

A value for the true base at a locus of the first polynucleotide and error calling are determined using a computer to process sequencing data according to the table found in FIG. 20D, wherein the "F strand" and "F" values represent a determined value of a base of the first polynucleotide at the locus and the "F' strand" and "F'" values represent a determined value of a base of the second polynucleotide at the corresponding locus on the second polynucleotide.

Example 7: Alternate Method for Two-Base Sequencing with 6-Letter Base Discrimination Comprising TET Treatment This example shows the use of two-base sequencing comprising treatment with a glycosylation agent and a methyltransferase for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA polynucleotide (comprising the first and second polynucleotides) is exposed to DNA methyltransferase-5 (DNMT5) (e.g., as shown in FIG. 4) or DNMT1. If additional sensitivity in distinguishing 5-methylcytosine from 5-hydroxymethylcytosine is applicable, the first polynucleotide can be contacted with b-glucosyltransferase before contacting the double-stranded DNA polynucleotide with DNA methyltransferase. In cases where b-glucosyltransferase is used, DNMT1 or DNMT5 can be used as the methyltransferase. The double-stranded DNA polynucleotide is exposed to a solution comprising the oxidizing agent TET after contacting the double-stranded DNA polynucleotide with the methyltransferase. In some cases, a biologically active fragment of TET can be used. The double-stranded DNA polynucleotide is then exposed to borane to chemically reduce caC residues before treatment with a mild acid (alternatively, a mild base can be used). Hairpin polynucleotides are then melted, a read polynucleotide is generated using PCR, and the first polynucleotide and read polynucleotide are sequenced.

A value for the true base at a locus of the first polynucleotide and error calling are determined using a computer to process sequencing data according to the table found in FIG. 20D, wherein the "F strand" and "F" values represent a determined value of a base of the first polynucleotide at the locus and the "F' strand" and "F'" values represent a determined value of a base of the second polynucleotide at the corresponding locus on the second polynucleotide.

Example 8: Two-Base Sequencing with 6-Letter Base Discrimination Comprising β-glucosyltransferase Treatment This example shows the use of two-base sequencing comprising treatment with a glycosylation agent and a methyltransferase for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA is exposed to β-glucosyltransferase, as shown in FIG. 1B (or, alternatively, as shown in FIG. 1A). The double-stranded DNA polynucleotide is then exposed to DNMT1 to transfer unprotected 5-methylcytosine tags to cytosines proximal to the corresponding locus on the second polynucleotide. The double-stranded DNA is then deaminated by exposure to bisulfite before hairpins are melted, a read polynucleotide is generated using PCR, and the first polynucleotide and read polynucleotide are sequenced.

A value for the true base at a locus of the first polynucleotide and error calling are determined using a computer to process sequencing data according to the table found in FIG. 20E, wherein the "F strand" and "F" values represent a determined value of a base of the first polynucleotide at the locus and the "F' strand" and "F'" values represent a determined value of a base of the second polynucleotide at the corresponding locus on the second polynucleotide.

Figure 20F:
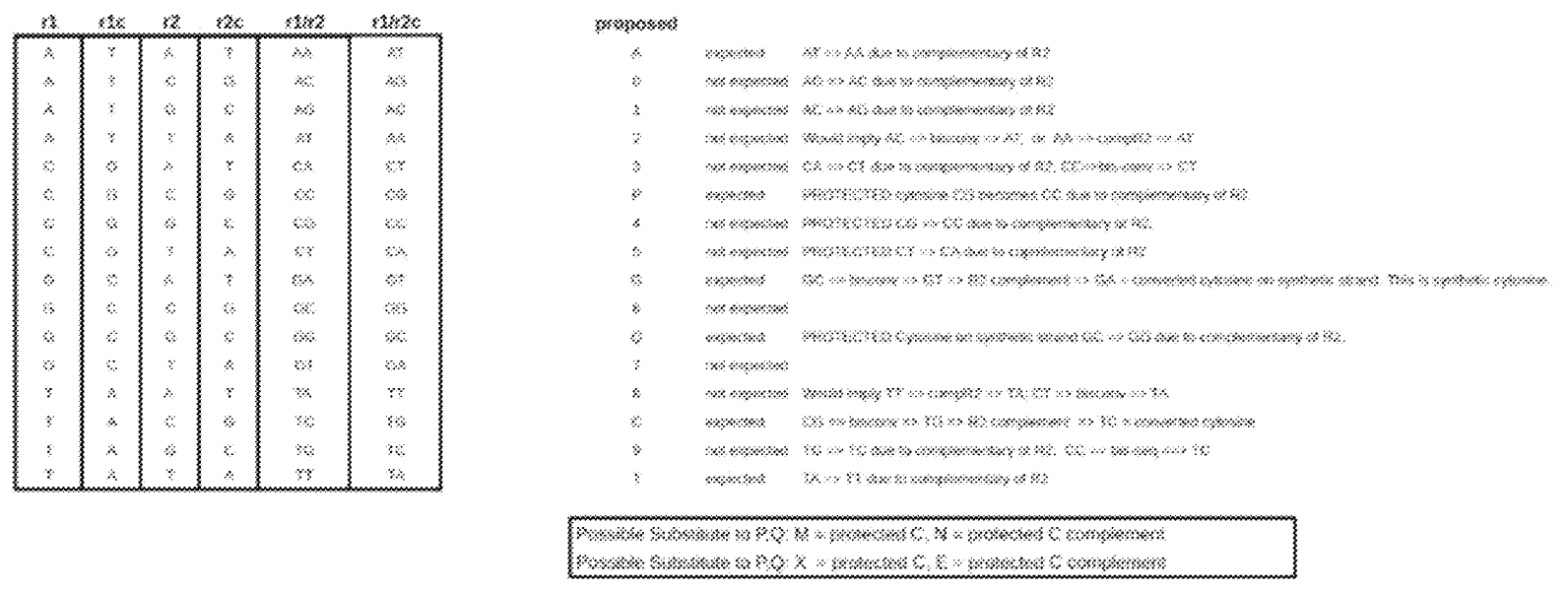
Figure 21:
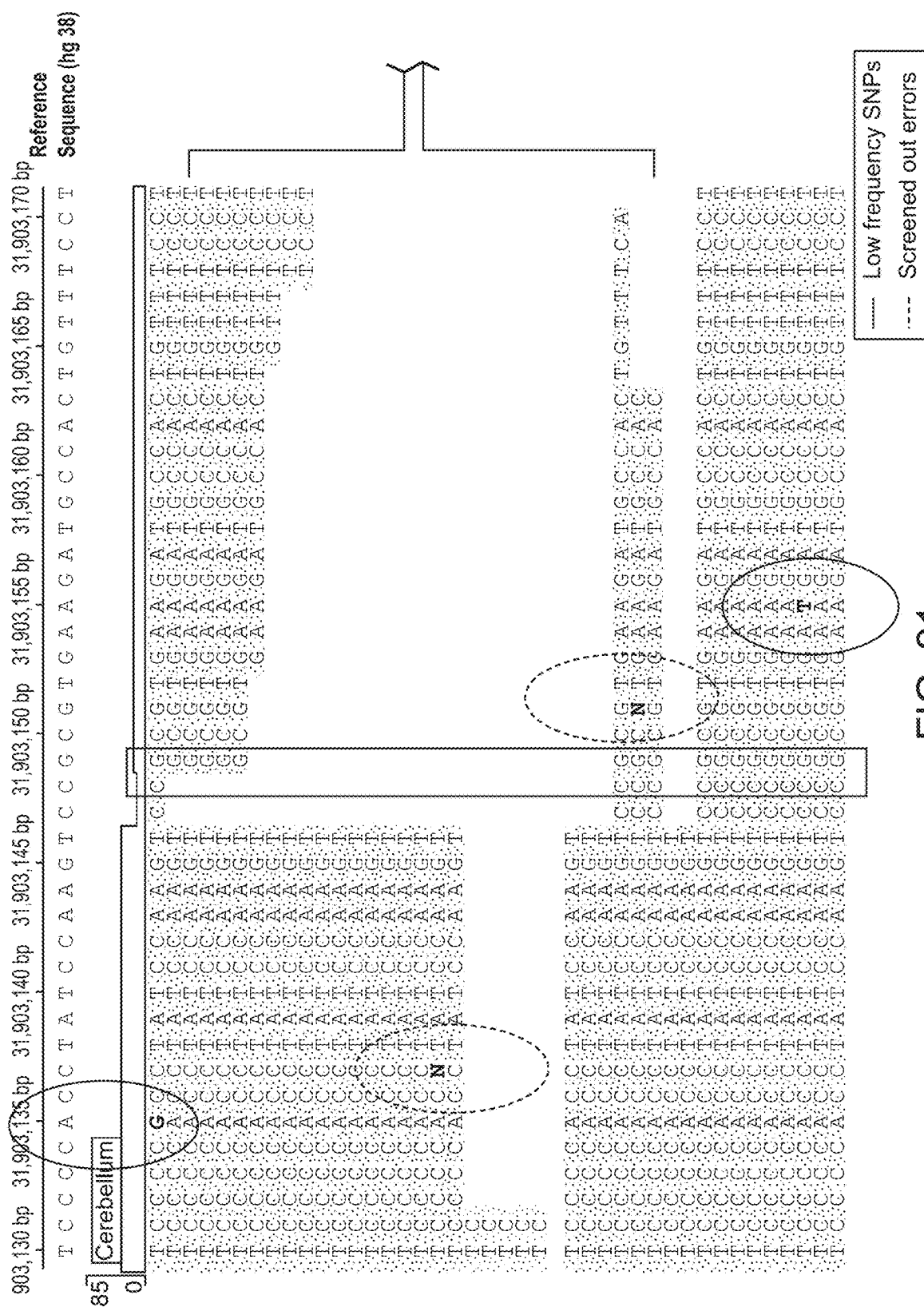
FIG. 21 shows experimental data produced in the determination of a value of a base of a polynucleotide, in accordance with embodiments.
Figure 21:
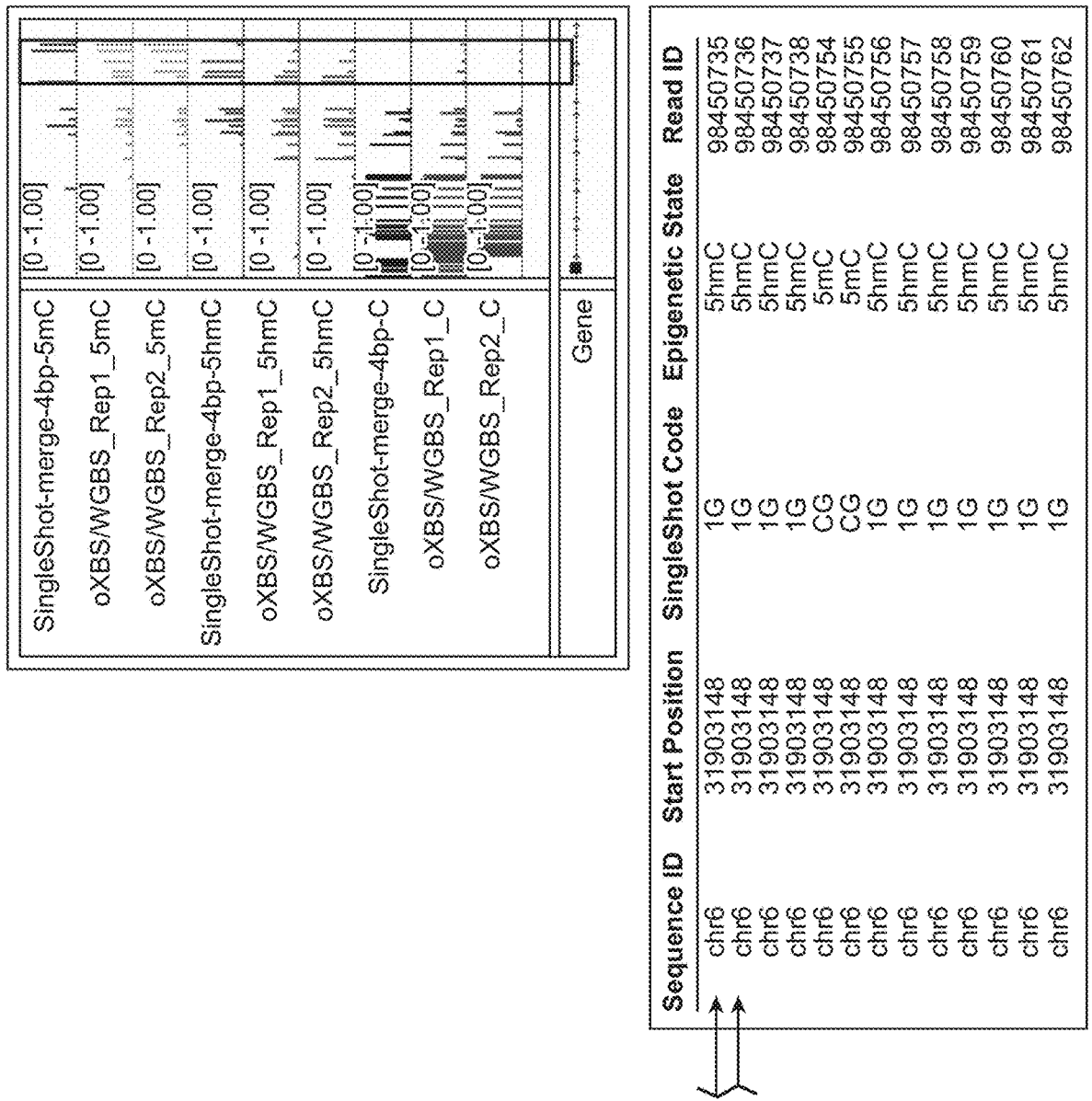

Alternately, a value for the true base is determined according to the table found in FIG. 20F, wherein "r1" represents the detected base value on the first polynucleotide, "r2" represents the detected base value on the read polynucleotide, "r2c" represents the base value on the second polynucleotide, "r1/r2" represents the combination of the detected base values for the first polynucleotide and the read polynucleotide, "r1/r2c" represents the combination of the base values for the first polynucleotide and the second polynucleotide, "A" represents adenine, "G" represents guanine, "T" represents thymine, "C" represents cytosine, and the number 0 through 9 represent individual error calls. Experimental data using this method can be seen in FIG. 21. Shown in purple are sequencing events that resulted in error calls (e.g., sequencing errors identified as miscalls); shown in red are base mismatches identified as true low frequency mutations. Methylation levels (e.g., hydroxymethylation levels are quantified in the table of FIG. 21).

Example 9: Alternate Method of Two-Base Sequencing with 6-Letter Base Discrimination Comprising β-glucosyltransferase Treatment This example shows the use of two-base sequencing comprising treatment with a glycosylation agent and a methyltransferase for determining a value of a base in an original polynucleotide of a sample.

Figure 19E:
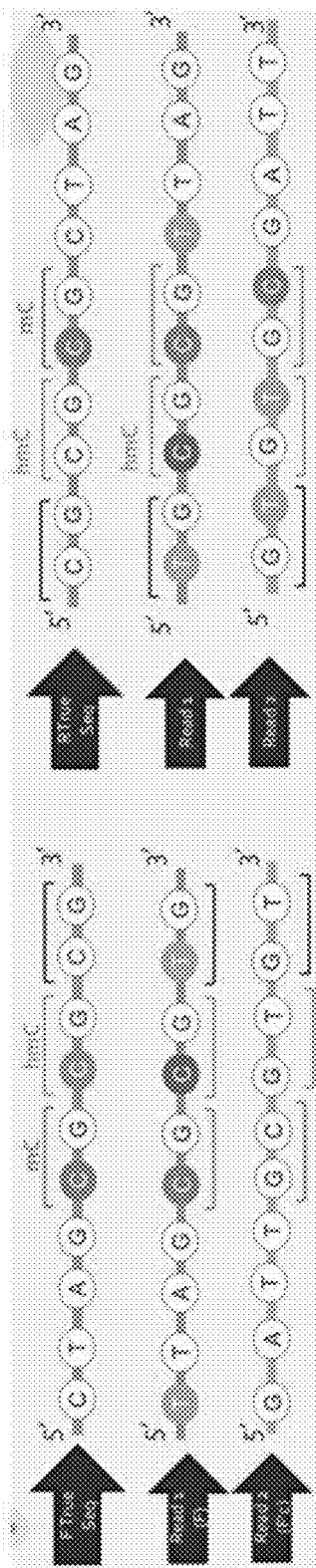

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA is exposed to β-glucosyltransferase (bGT) (e.g., as shown in FIG. 2A). The double-stranded DNA polynucleotide is then exposed to DNMT1 to transfer unprotected 5-methylcytosine tags to cytosines proximal to the corresponding locus on the second polynucleotide. Double-stranded DNA polynucleotides are then oxidized with TET and exposed to bGT a second time. In some cases, it can be expedient to contact the first and second polynucleotides with a solution comprising the oxidizing agent (e.g., TET) and bGT; however, the first and second polynucleotides can be exposed to TET and then bGT, serially. The double-stranded DNA is then separated using a helicase (or single-stranded DNA-binding protein) and deaminated using APOBEC3A, or fragments thereof. A read polynucleotide is generated using PCR while the double-stranded DNA is separated, and the first polynucleotide and read polynucleotide are sequenced (e.g., as shown in FIG. 19E). Strand-displacing PCR reagents and/or heating can be used to separate the first and second polynucleotides to perform PCR in cases where the helicase is no longer present/active.

A value for the true base at a locus of the first polynucleotide and error calling are determined using a computer to process sequencing data according to the table found in FIG. 20E, wherein the "F strand" and "F" values represent a determined value of a base of the first polynucleotide at the locus and the "F' strand" and "F'" values represent a determined value of a base of the second polynucleotide at the corresponding locus on the second polynucleotide.

Alternately, a value for the true base is determined according to the table found in FIG. 20F, wherein "r1" represents the detected base value on the first polynucleotide, "r2" represents the detected base value on the read polynucleotide, "r2c" represents the base value on the second polynucleotide, "r1/r2" represents the combination of the detected base values for the first polynucleotide and the read polynucleotide, "r1/r2c" represents the combination of the base values for the first polynucleotide and the second

Example 10: Two-Base Sequencing with 6-Letter Base Discrimination Comprising β-glucosyltransferase and SAM Analog Treatment This example shows the use of two-base sequencing comprising treatment with a glycosylation agent and a methyltransferase for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA is exposed to β-glucosyltransferase (bGT) (e.g., as shown in FIG. 2C). The double-stranded DNA polynucleotide is then exposed to DNMT1 to transfer unprotected 5-methylcytosine tags to cytosines proximal to the corresponding locus on the second polynucleotide. Double-stranded DNA polynucleotides are then exposed to a solution comprising S-adenosylmethionine (SAM) analog and a DNA methyltransferase. The double-stranded DNA is then separated using a helicase (or single-stranded DNA-binding protein) and deaminated using APOBEC3A, or fragments thereof. A read polynucleotide is generated using PCR while the double-stranded DNA is separated, a read polynucleotide is generated using PCR, and the first polynucleotide and read polynucleotide are sequenced. Strand-displacing PCR reagents and/or heating can be used to separate the first and second polynucleotides to perform PCR in cases where the helicase is no longer present/active.

A value for the true base at a locus of the first polynucleotide and error calling are determined using a computer to process sequencing data according to the table found in FIG. 20E, wherein the "F strand" and "F" values represent a determined value of a base of the first polynucleotide at the locus and the "F' strand" and "F'" values represent a determined value of a base of the second polynucleotide at the corresponding locus on the second polynucleotide.

Alternately, a value for the true base is determined according to the table found in FIG. 20F, wherein "r1" represents the detected base value on the first polynucleotide, "r2" represents the detected base value on the read polynucleotide, "r2c" represents the base value on the second polynucleotide, "r1/r2" represents the combination of the detected base values for the first polynucleotide and the read polynucleotide, "r1/r2c" represents the combination of the base values for the first polynucleotide and the second polynucleotide, "A" represents adenine, "G" represents guanine, "T" represents thymine, "C" represents cytosine, and the number 0 through 9 represent individual error calls.

Example 11: Two-Base Sequencing with 6-Letter Base Discrimination Comprising β-glucosyltransferase and SAM Analog Treatment This example shows the use of two-base sequencing comprising treatment with a glycosylation agent and a methyltransferase for determining a value of a base in an original polynucleotide of a sample.

A double-stranded DNA polynucleotide comprising a first polynucleotide (e.g., which comprises a cell-free DNA original polynucleotide) a second polynucleotide, a hairpin polynucleotide, and adapter polynucleotides is provided as described in Example 1. The double-stranded DNA polynucleotide is exposed to DNMT1 to transfer unprotected 5-methylcytosine tags to cytosines proximal to the corresponding locus on the second polynucleotide (e.g., as shown in FIG. 2B). The double-stranded DNA is then exposed to β-glucosyltransferase (bGT). Double-stranded DNA polynucleotides are then exposed to a solution comprising S-adenosylmethionine (SAM) analog and a DNA methyltransferase. The double-stranded DNA is then separated using a helicase (or single-stranded DNA-binding protein) and deaminated using APOBEC3A, or fragments thereof. A read polynucleotide is generated using PCR while the double-stranded DNA is separated, a read polynucleotide is generated using PCR, and the first polynucleotide and read polynucleotide are sequenced. Strand-displacing PCR reagents and/or heating can be used to separate the first and second polynucleotides to perform PCR in cases where the helicase is no longer present/active.

A value for the true base at a locus of the first polynucleotide and error calling are determined using a computer to process sequencing data according to the FIG. 2B.

Example 12: Two-Base Sequencing with 5-Letter Base Discrimination Comprising TET Treatment and β-glucosyltransferase Treatment This example describes the processing of double-stranded nucleic acids with an oxidizing agent (e.g., a TET enzyme), a glycosylation agent (e.g., a glucosyltransferase, such as, for example, β-glucosyltransferase, a deaminating agent (a deaminase) and a helicase to identify modified (e.g., methylated) bases in a nucleic acid molecule. In particular, this example differentiates and identifies methylated cytosine bases (e.g., methylcytosine, including 5-methylcytosine; hydroxymethylcytosine, including 5-hydroxymethyl cytosine) from unmethylated cytosine bases. Such differentiation and identification can be at single base resolution.

Figure 23:
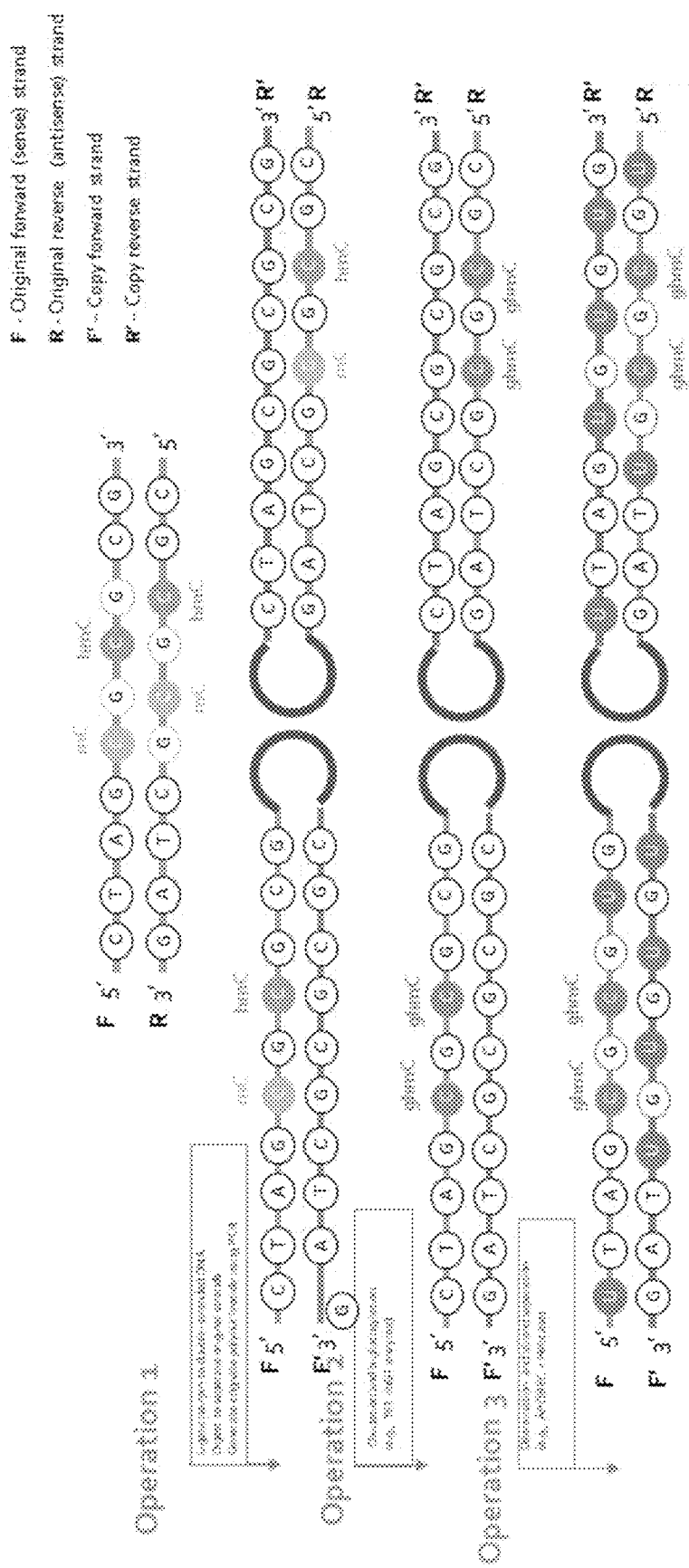
FIG. 23 shows operations for identifying a base in a polynucleotide, in accordance with embodiments.

In some cases, as depicted in FIG. 23, two double-stranded polynucleotides (e.g., double-stranded DNA) comprising a first strand and a second strand that are hybridized together and also separately linked together (e.g., via one or more hairpin adapters). In some cases, the first strand is linked to a hairpin adapter at a 3' end of the first strand, and the hairpin adapter linked to the second strand at a 5' end of the second strand (see left half of FIG. 23). In some cases, the first strand is linked to a hairpin adapter at a 5' end of the first strand, and the hairpin adapter linked to the second strand at a 3' end of the second strand (see right half of FIG. 23). Examples for generating such double-stranded polynucleotides having hybridized and linked strands from an original polynucleotide, including an original double-stranded polynucleotide, are described elsewhere herein, including with respect to Example 1, FIG. 1A, FIG. 1B, FIG. 19A and FIG. 19B. Operation 1 of FIG. 23 also provides example operations for generating such double-stranded polynucleotides. Sequencing adapters can be added prior to, during or after the processing operations described below are performed. In this example, as depicted in FIG. 23, the provided double-stranded polynucleotides (the first shown to the left on FIG. 23, the second shown to the right on FIG. 23) comprise methylcytosine (mC in FIG. 23, e.g., 5-methylcytosine) and hydroxymethylcytosine (hmC in FIG. 23, e.g., 5-hydroxymethylcytosine) bases and one original strand of the original double-stranded polynucleotide from which they are derived. The methylated bases are on the original strand.

With reference to FIG. 23, the double-stranded polynucleotides are exposed to the oxidizing agent, which can be an oxidase, such as, for example, a TET enzyme. In some cases, a biologically active fragment of an oxidase (e.g., a TET) is used. The oxidizing agent converts the methylcytosine bases to hydroxymethylcytosine.

Prior to, simultaneous with, or following treatment with the oxidizing agent, the double-stranded polynucleotides are exposed, in the presence of a glucose source (e.g., uridinediphosphate glucose (UDPG)), to a glycosylation agent (e.g., β-glucosyltransferase (bGT) as shown in Operation 2 in FIG. 23) that can glycosylate hydroymethylcytosine to glycosylhydroxymethylcytosine (ghmC in FIG. 23). Such glycosylation can protect the hydroxmethylcytosine from the activity of other agents, including the deaminating agent described below. Methylcytosine bases can be glycosylated after transformation to hydroxymethylcytosine via the oxidizing agent.

Next, the double-stranded polynucleotides are exposed to a deaminating agent and a helicase as in Operation 3 of FIG. 23. In this example, the deaminating agent is a deaminase (e.g., cytosine deaminase), such, as, for example, APOBEC (e.g., APOBEC3A as in FIG. 23) or a fragment thereof. The helicase separates at least a portion of the strands of the double-stranded polynucleotides from each other and the deaminase removes amine groups from cytosine bases that have not been glycosylated (e.g., those glycosylated originally were methylcytosine or hydroxymethylcytosine). Such deaminated cytosine bases are transformed to uracil, with glycosylated cytosine bases remaining glycosylated cytosine.

The processed double-stranded polynucleotides can then be treated to add sequencing adapters (if not already added previously) and then sequenced. In some cases, the processed double-stranded polynucleotides are further processed, after processing, such as, for example, subjected to amplification, prior to sequencing.

During sequencing, and as an example depicted in FIG. 25, called cytosine bases on one strand and corresponding (e.g., via physical proximity) to guanine calls in the other strand are used to identify cytosine bases that were methylated (e.g., were either methylcytosine or hydroxymethylcytosine) in the original double-stranded polynucleotide from which the treated double-stranded polynucleotides were derived. Moreover, generated uracil bases (in some cases, called thymine during sequencing, as a result of amplification after processing of the double-stranded polynucleotides) on one strand and corresponding (e.g., via physical proximity) to guanine on the other strand are used to identify cytosine bases that were not methylated in the original double-stranded polynucleotide from which the treated double-stranded polynucleotides were derived. Other base calling pairings, between strands, for adenine, thymine and guanine base calls are also shown in FIG. 25, along with pairings that represent a sequencing error. Pairing of calls can improve accuracy of sequencing calls and also reduce sequencing depth needed to achieve such improved accuracy, as is described elsewhere herein. A computer can be used to aid in analyzing sequencing data to make base calls.

Example 13: Two-Base Sequencing with 4-Letter Base Discrimination Comprising APOBEC and Helicase Treatment This example describes the processing of double-stranded nucleic acids with a deaminating agent (a deaminase) and a helicase to identify bases in a nucleic acid molecule. Identification of bases and differentiation of bases from other bases can be at single base resolution.

Figure 24:
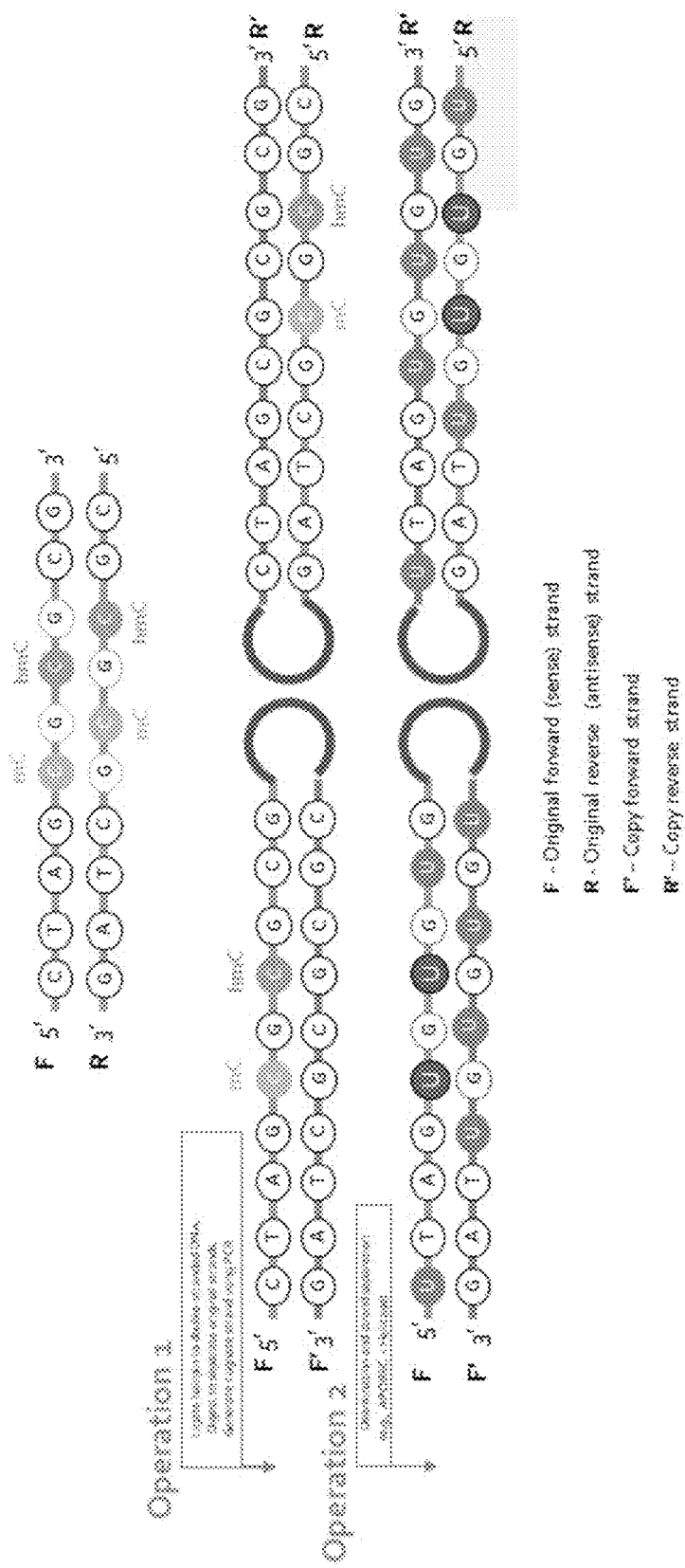
FIG. 24 shows operations for identifying a base in a polynucleotide, in accordance with embodiments.

Prior to processing and as depicted in FIG. 24, two double-stranded polynucleotides (e.g., double-stranded DNA) comprising a first strand and a second strand that are hybridized together and also separately linked together (e.g., via one or more hairpin adapters). In some cases, the first strand is linked to a hairpin adapter at a 3' end of the first strand, and the hairpin adapter linked to the second strand at a 5' end of the second strand (see left half of FIG. 24). In some cases, the first strand is linked to a hairpin adapter at a 5' end of the first strand, and the hairpin adapter linked to the second strand at a 3' end of the second strand (see right half of FIG. 24). Examples for generating such double-stranded polynucleotides having hybridized and linked strands from an original polynucleotide, including an original double-stranded polynucleotide, are described elsewhere herein, including with respect to Example 1, FIG. 1A, FIG. 1B, FIG. 19A and FIG. 19B. Operation 1 of FIG. 24 also provides example operations for generating such double-stranded polynucleotides. Sequencing adapters can be added prior to, during or after the processing operations described below are performed. In this example, as depicted in FIG. 24, the provided double-stranded polynucleotides (the first shown to the left on FIG. 24, the second shown to the right on FIG. 23) comprise methylcytosine (mC in FIG. 24, e.g., 5-methylcytosine) and hydroxymethylcytosine (hmC in FIG. 24, e.g., 5-hydroxymethylcytosine) bases and one original strand of the original double-stranded polynucleotide from which they are derived.

With reference to FIG. 24, the double-stranded polynucleotides are exposed to a deaminating agent and a helicase as in Operation 2 of FIG. 24. In this example, the deaminating agent is a deaminase (e.g., cytosine deaminase), such, as, for example, APOBEC (e.g., APOBEC3A as in FIG. 24) or a fragment thereof. The helicase separates at least a portion of the strands of the double-stranded polynucleotides from each other and the deaminase removes amine groups from cytosine bases, including those that are methylated. Such deaminated cytosine bases are transformed to uracil.

The processed double-stranded polynucleotides can then be treated to add sequencing adapters (if not already added previously) and then sequenced. In some cases, the processed double-stranded polynucleotides are further processed, after processing, such as, for example, subjected to amplification, prior to sequencing. While methylated bases are shown in FIG. 24, the example of FIG. 24 can be equally applied to an unmethylated cytosine base(s) and its/their detection.

During sequencing, and as an example depicted in FIG. 26, generated uracil bases (in some cases, called as thymine during sequencing as a result of amplification after processing of the double-stranded polynucleotides) on one strand and corresponding (e.g., via physical proximity) to guanine on the other strand are used to identify cytosine bases, including those that were methylated, in the original double-stranded polynucleotide from which the treated double-stranded polynucleotides were derived. Other base calling pairings, between strands, for adenine, thymine and guanine base calls are also shown in FIG. 26, along with pairings that represent a sequencing error. Pairing of calls can improve accuracy of sequencing calls and also reduce sequencing depth needed to achieve such improved accuracy, as is described elsewhere herein. A computer can be used to aid in analyzing sequencing data to make base calls.

Example 14: Sequencing Error Suppression Using Two-Base Sequencing Methods for Improved Genomic Variant Calling NA24385 (Ashkenazi Jewish child) and NA24631 (Han Chinese child) cell line samples were prepared for high-throughput sequencing and sequenced to a sequencing depth of ~80× (NA24385) and ~90× (NA24631) on the NovaSeq Illumina sequencing platform (FIG. 28). Short single-end reads were generated (~111 bp length for both NA24385 and NA24631 samples) using the 4-letter base-calling methods described in Example 2, where a value for the true base at a locus of the first polynucleotide and error calling were determined using a computer to process sequencing data according to the table found in FIG. 20A, wherein the "F strand" and "F" values represent a determined value of a base of the first polynucleotide at the locus and the "F' strand" and "F'" values represent a determined value of a base of the second polynucleotide at the corresponding locus on the second polynucleotide A processing pipeline for the single-end reads was implemented to call genomic variants from the sequencing read-out data. First, the quality of the raw paired-end reads obtained from the sequencing experiment were checked by FastQC, and low-quality reads were removed by fastp. Single-end reads were then produced using the 4-letter base-calling approach described in Example 2. The single-end reads (approximately 2.2 billion reads for the NA24385 sample and 2.4 billion for the NA24631 sample) were mapped to the reference genome GRCh38DH by BWA-mem v0.7.15 (FIG. 28) Aligned reads were converted to BAM files and sorted based on genome position after marking duplicates using Picard modules. The raw BAM files were refined by Base Quality Score Recalibration (BQSR) using default parameters except for the binning of quality scores which occurred at Q10, Q20, Q30, and Q40 as recommended by a 2018 variant calling pipeline standard (doi.org). After de-duplication, both NA24385 and NA24631 samples showed a read depth of ~30X coverage (FIG. 28). Germline variant calling (SNPs and indels) was performed with the HaplotypeCaller module of GATK (version 4.1.9.0). Variants were filtered using a GATK hard-filtering approach. The following filter expression: "QD<2.0||FS>30.0||SOR>3.0||MQ<40.0||MQRankSum<−3.0||ReadPosRankSum<−3.0" was used to filter out variants that have annotation values above or below the set thresholds. Further metrics of the sequencing results are presented in FIG. 28.

Approximately 3.3 million SNPs were detected in the NA24385 and NA24631 samples. 97.1% and 97.2% of the detected SNPs in the NA24385 and NA24631 samples respectively were present in the dbSNP database (FIG. 29). The performance of the variant calling pipeline for SNP detection was evaluated based on the transition (Ti) and transversion (Tv) conversion ratio of novel SNPs (1.93 and 2.10 for NA24385 and NA24631 samples respectively) and known SNPs (2.074 and 2.069 for NA24385 and NA24631 samples respectively) (FIG. 29). The Ti/Tv ratio is expected to be ~2-2.1 when considering SNPs at a genome wide level.

Approximately 640,000 indels were detected by the variant calling pipeline, out of which 93.9% of the indels detected in the NA24385 and about 94.2% of the indels detected in the NA24631 samples intersected with the indels in the dbSNP database (FIG. 29). The ratio of Insertion/Deletion for known indels was ~0.9 for both NA24385 and NA24631 samples matching the expected value of the ratio at ~1. The ratio of Insertion/Deletion for novel indels was 0.93 for NA24385 and 0.96 for the NA24631 samples which closely matched the expected ratio at ~1, further validating the quality of the sequencing data that were obtained (FIG. 29).

The results of the sequencing experiment were evaluated by comparing identified SNPs and indels with gold-standard variants defined in the NIST dataset (FIG. 30). Briefly, the heterozygote SNP variants in the NIST database were detected with 91.9% and 94.2% sensitivity in the NA24385 and NA24631 samples respectively (FIG. 30). The homozygote SNP variants in the NIST database were detected with 92.0% and 94.7% sensitivity in the NA24385 and NA24631 samples respectively (FIG. 30). The PPV for detection of heterozygote and homozygote SNP variants was 99% and 99.9% respectively in the NA24385 sample (FIG. 30). The PPV for detection of heterozygote and homozygote SNP variants was 98.9% and 99.9% in the NA24631 sample respectively (FIG. 30). The genotype concordance for SNPs detected was 99.9% for both the NA24385 and NA24631 samples. The non-reference genotype concordance was measured at 91.4% and 93.8% for the NA24385 and NA24631 samples respectively (FIG. 30).

In comparison, the heterozygote indels in the NIST database were detected with 84.9% sensitivity and 88.6% in the NA24385 and NA24631 samples respectively (FIG. 30). The homozygote indel variants in the NIST database were detected with 84.3% sensitivity and 90.2% sensitivity in the NA24385 and NA24631 samples respectively (FIG. 30) The PPV for detection of homozygote indels was 99.4% and 99.3% in the NA24385 and NA24631 samples respectively. The PPV for detection of heterozygote indels was 96.7% and 97.4% in the NA24385 and NA24631 samples respectively. The genotype concordance for indel detection was 99.9% for both the NA24385 and NA24631 samples. The non-reference indel genotype concordance was measured at 82.5% and 87.5% for the NA24385 and NA24631 samples respectively, particularly highlighting the ability of the two-base sequencing methods herein to effectively capture homozygote alternative and heterozygous genotypes (FIG. 30).

The performance of the variant calling pipeline for SNP detection was further evaluated based on heterozygous (Het) and homozygous (Hom) detection, transition (Ti) and transversion (Tv) conversion of both novel and known SNPs and genotype concordance for SNPs based on intersection of the test and 'gold standard' NIST datasets. Sensitivity metrics (True Positive (TP)/(True Positive (TP)+False Negative (FN)) and Positive Predictive Value (PPV)(True Positive (TP)/(True Positive (TP)+False Positive (FP)) for detection of heterozygous and homozygous variants was calculated. Sensitivity metrics for Het/Hom detection and Ti/Tv ratios were calculated as described by Wang et al., 2014. TP is defined as a true positive variant that exists in NIST data set and also is detected by the pipeline; FP is a false positive variant that does not exist in the NIST data set and is detected by the pipeline; FN is a false negative variant that exists in the NIST dataset and is not detected by the pipeline Depth of coverage, which is the total number of bases sequenced and aligned at a given reference base position, was calculated by the Picard module RawWgsMetrics. The genotype (allele) concordance, which is the intersection of the 'test' and 'truth' datasets, was determined by the GenotypeConcordance module of Picard. Picard modules were run using the Picard tool implemented in GATK version 4.1.9.0. The ability of the pipeline to capture the non-reference genotype concordance, e.g., the ability to capture homozygote alternative and heterozygous genotypes was also calculated.

Next, results from the sequencing experiments were compared with publicly available (Illumina sequencing) data on the same samples (denoted NIST). Ins/Del ratio was calculated (represents the ratio of number of insertions to number of deletions and is expected to be under 1) for indels previously known in the dbSNP database and novel indels. While the total number of indels detected (642K and 639K for the NA24385 and NA24631 samples) was less than the number of indels present in the Illumina database (1.25 million and 1.12 million for the NIST NA24385 and NIST NA24631 respectively), a higher percentage of the indels detected by the two-base methods here intersected with the indels present in the dbSNP database compared to the standard publicly available data (FIG. 31) (93.9% vs 47.5% for the NA24385 samples and 94.2% vs 51.6% on the NA24631 samples). For the NIST NA24385 and NIST NA24631 samples, the Ins/Del ratios for the novel indels were much higher, suggesting that the sequencing results obtained on the NA24385 and NA24631 samples using two-base sequencing methods herein out-performed standard Illumina data available from NIST (FIG. 31).

Furthermore, comparison of the genotype concordance metric from the sequencing experiment to the publicly available data (standard Illumina data) on the same samples showed that the sequencing results on the NA24385 and NA24631 samples using the two-base sequencing methods outperformed standard Illumina data available from NIST. For example, the genotype concordance of the non-reference SNPs obtained using the two-base sequencing systems herein was 91.4% in the NA24385 sample, compared to genotype concordance of 82.2% of the non-reference SNPs for the NA24385 sample in the NIST database (FIG. 32). Similarly, the genotype concordance of the non-reference indels obtained in the NA24385 sample using the two-base sequencing systems herein was 82.5%, compared to genotype concordance of 38.3% of the non-reference indels for the NA24385 sample in the NIST database (FIG. 32).

In order to assess the low coverage performance of the two-base sequencing methods and systems herein, the Coirell maintained NIST reference material DNA samples NA24385 and NA24631 were prepared using the workflow exemplified in Example 8 and whole-genome sequenced using an Illumina NovaSeq 6000 system. After obtaining the raw sequencing data, quality control was conducted, and reads were mapped to the hg38 reference genome. After removing duplicated reads using Picard, the average depth of NA24385 and NA24631 was 30.1× and 29.6×, respectively (FIG. 28). The NA24385 bam file was down-sampled to 6× coverage and germline variants were called using the HaplotypeCaller module of GATK. The analysis on the down-sampled bam-file was conducted both with (5×) and without duplicate marking (6×) (FIG. 34) and the detailed information of the variant calling analysis is present in FIG. 35. For the deduplicated (5×) sample, 96.3% of SNPs and 95.7% of indels were known variants found in the dbSNP database.

In order to investigate the ability of two-base sequencing methods to detect low allele fraction variants, a "mix-in" sample with a 1% variant allele fraction was created. Specifically, NA24385 was subsampled to ~1× coverage (corresponding to three "chunks" of each 10 million read pairs) and merged with the full depth NA24631 sample to create a mix-in sample with a coverage of 92.3× (FIG. 33A and FIG. 33B) A somatic variant calling pipeline was run using the Mutect2 module of GATK by specifying the mix-in sample as "tumor" sample and NA24631 as "normal" sample. The variant calls made on the mix-in sample was assessed for sensitivity (number of calls made that overlap with calls made against the full NA24385 but do not overlap with calls made on the full NA24631) and specificity (related to the number of calls made that do not overlap the calls made against either the full NA24385 or NA24631). There were 4,464,429 total variant calls made on the full NA24385 of which, 2,687,773 variant calls were present in NA24631 (and 1,776,656 were not). A sensitivity of 12.3% was observed for the 1% mix-in sample where out of the total of 1,776,656 variants unique to NA24385, 218,574 of these were called in the mix-in sample. There were 19,161 total somatic calls made on the mix-in that did not have any read evidence in either NA24385 or NA24631 providing a specificity exceeding 99.999%.

Figure 36A:
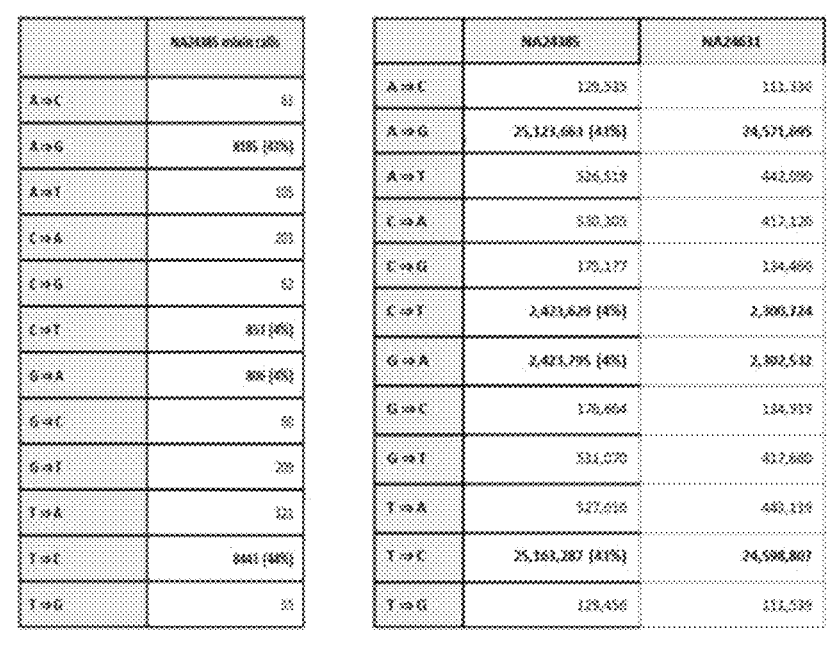

Analysis of the (1) miscalls from the mix-in sample that did not have any read evidence in NA24385 or NA24631 (FIG. 36A) and (2) singleton errors from the NA24385 and NA24631 sequencing reads (FIG. 36B) showed that A<→G and C<→T false positives were more frequent than any other type of errors. Singleton errors were defined as genomic sites with a coverage of at least 20 reads carrying the hg38 reference allele and exactly one read harboring an alternative allele. The bias in miscall and singleton error types is expected, given that A<→G and C<→T errors of sequencing reads analyzed using the two-base sequencing analysis methods may occur due to one base miscall while the other types of sequencing errors may occur due to two base miscalls. For example, an A base resolved by the two-base sequencing method here is given by an A on the original strand and a T on the copy strand. A T base resolved by the two-base sequencing method here is given by a T on the original strand and an A on the copy strand. As such for an A to be miscalled as a T, in the original strand, an A may be miscalled as a T, while simultaneously miscalling the T in the copy strand as an A. On the other hand, for other miscalls, e.g., A→G or C→T, may occur due to one sequencing error. As an example, an A base resolved by the two-base sequencing method here is given by an A on the original strand and a T on the copy strand. A G base resolved by the two-base sequencing method is given by a G on the original strand and a T on the copy strand. As such, for an A to be miscalled as a G, it means that in the original strand, the A has been miscalled as a G. However, since the T on the copy strand is already a T, a single sequencing error can result in an A→G miscall (FIG. 27 and FIG. 37).

Figure 38:
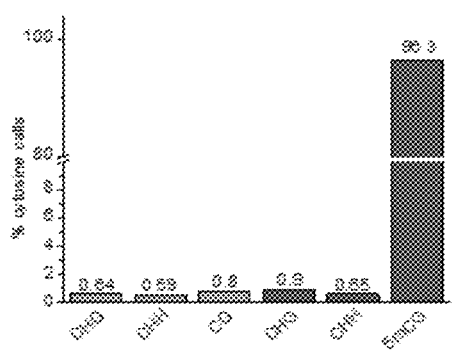
FIG. 38 shows the rate of false-positive methylation calling in normal control paired end libraries or two-base sequencing libraries deaminated with APOBEC, or a fragment thereof, alone.

Example 15: Increased Efficiency of Deamination Using a Combination of APOBEC3A and Helicase Leads to Reduction in Sequencing Errors The false-positive rate of methylation calls in the two-base sequencing methods (and bisulphite sequencing) can be partially determined by the proportion of unconverted cytosines that is attributable to incomplete deamination by the APOBEC enzyme. APOBEC3A deamination functions to make libraries single-stranded and can be inhibited by the presence of inter- or intra-molecular dsDNA and can apply in both normal paired-end libraries and two-base sequencing. In order to confirm that false-positive rates due to APOBEC3A are similar to those reported in the literature (for example, FP rate of 0.25% as per Sun, Z. et.al, 2021), a control normal paired-end library was prepared from 100 ng of human cerebellum gDNA with contain small amounts (0.5%) of unmethylated pUC19 and methylated lambda phage DNA (wherein the CpG context of the lambda phage DNA was methylated using the enzyme M.SssI). After NGS adapters are ligated the library was treated with TET and subsequently heat and formamide treatment used to denature the library followed by APOBEC3A treatment for 3 hours at 37° C. Following PCR, NGS sequencing, mapping and deduplication, Cytosine and Thymine reads were resolved in the original forward strand of the sequencing libraries. The sequencing reads were interpreted based on the CpG, CHH or CHG context (C=failed deamination in a non-CpG context whereas C=methylated cytosine in a CpG context) using the MethylDackel software. The results of the sequencing showed that the false positive rate of methylation-calling in the control samples are on par (e.g. Cytosine calls in CpG context are ~0.8%, FIG. 38) with false-positive rates in the recorded literature, e.g., EM-SEQ method (FP rate of 0.25% as per Sun, Z. et.al, 2021), Bisulphite sequencing (FP rate of 1.7/6-0.6% as per Holmes. et.al, 2014) or Tet-assisted pyridine-borane sequencing (FP rate of 0.23% as per Liu, Y. et. al, 2019) (FIG. 38).

In order to assess the rate of de-novo methylation that can occur in two-base sequencing, libraries were prepared as mentioned above (Libraries were prepared by mechanical shearing of 500 ng cerebellum gDNA containing 0.5% pUC19 and methylated lambda gDNA to a size of ~250 bp). Given that the cognate strand in these libraries may snap back to form the hairpin faster than APOBEC3A is able to deaminate the library, a helicase may be used in combination with APOBEC3A, or a fragment thereof.

Figure 43:
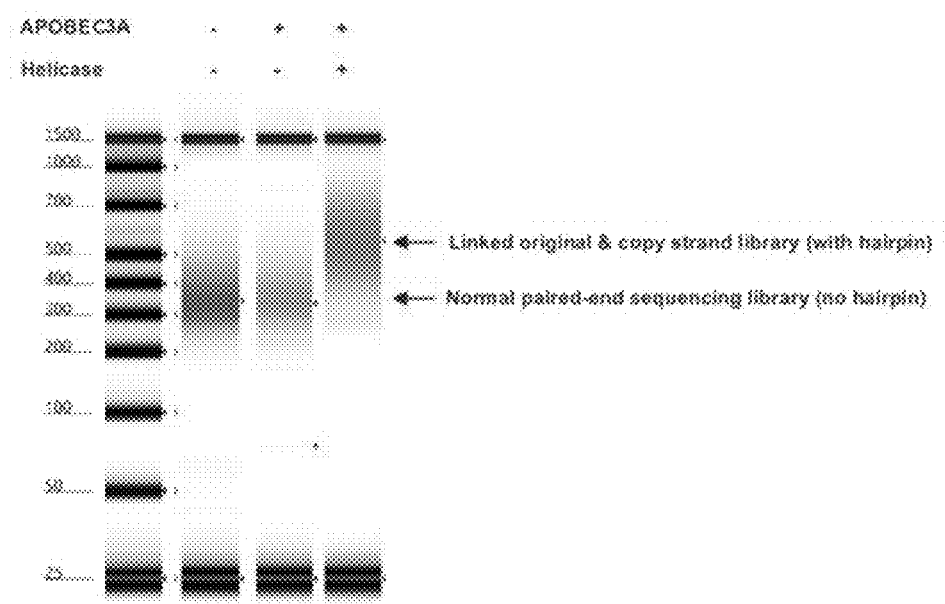
FIG. 43 depicts example library sizes recovered in a PCR (12 cycles of PCR) before sequencing.
Figure 44:
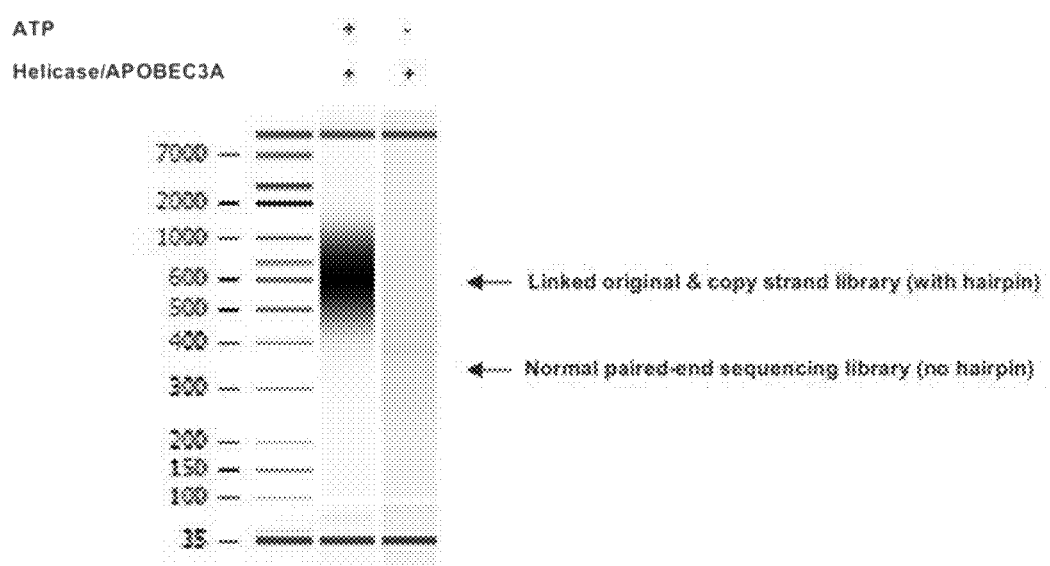
FIG. 44 depicts example library sizes recovered in a PCR (8 cycles of PCR) before sequencing.

Combining the helicase with APOBEC3A can be used to recover a sequencing library with paired original and copy strands joined with a hairpin. Upon leaving out the helicase, or both helicase and APOBEC3A, normal paired-end libraries that do not have the ligated hairpin can be amplified. Upon addition of both, longer libraries can be recovered that contain an original deaminated stand with its corresponding deaminated copy strand linked with a hairpin (as confirmed by sequencing) (FIG. 43). The recovery of longer deaminated libraries whereby an original strand is linked to a copy strand can be an active process involving turnover of ATP by the helicase which allows APOBEC3A to deaminate the linked duplex. In the absence of ATP, a normal paired-end library (which is present in the minority) can be amplified (FIG. 44).

Figure 39:
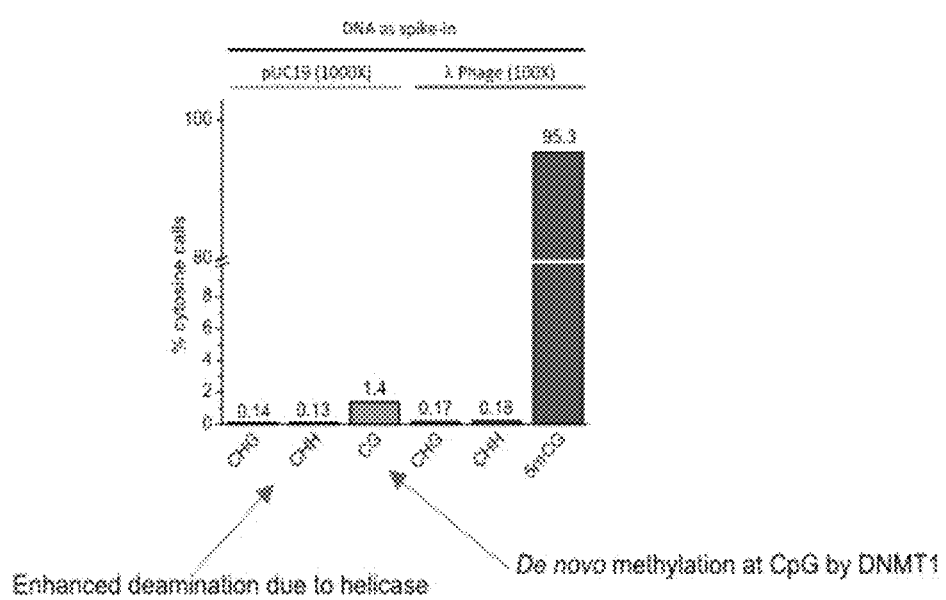
FIG. 39 shows suppression of false-positive methylation calls in two-base sequencing libraries deaminated using a combination of APOBEC3A and helicase, or fragments thereof.

To carry out two-base sequencing and to be able to measure false positive rates due to deamination failure, a hairpin was adapted, followed by copy strand synthesis, followed by TET and βGT treatment. A combination of helicase (e.g. UvrD, PcrA or Bad helicase nuclease-dead, wherein the E. coli UvrD helicase for example is present at a 100-fold molar excess to the DNA) and APOBEC3A was used in the presence of 2.5 mM ATP for 3 hours at 37° C. After mapping and deduplication, Cytosine and Thymine reads were resolved in the original forward strand of the sequencing libraries prepared for two-base sequencing. The sequencing reads were interpreted based on the CpG, CHH or CHG context (C=failed deamination in a non-CpG context whereas C=methylated cytosine in a CpG context) using the MethylDackel software. The results of the sequencing showed that the false positive rate of methylation-calling in the control samples (two-base sequencing libraries treated with APOBEC3A alone or normal paired-end libraries treated with APOBEC3A alone) is significantly higher than the deamination rates measured for other methods (e.g., in CpG context, the false positive rate due to deamination is ~0.062%) (FIG. 39). Hence, the helicase works in conjunction with APOBEC3A to increase the deamination rate, and thereby decrease the false-positive rate of methylation calls below a level achieved with bioinformatic filtering (as shown in Schutsky et. al, 2018 incorporated herein in its entirety). In the absence of a helicase, APOBEC3A may not deaminate hairpin libraries.

Figure 40:
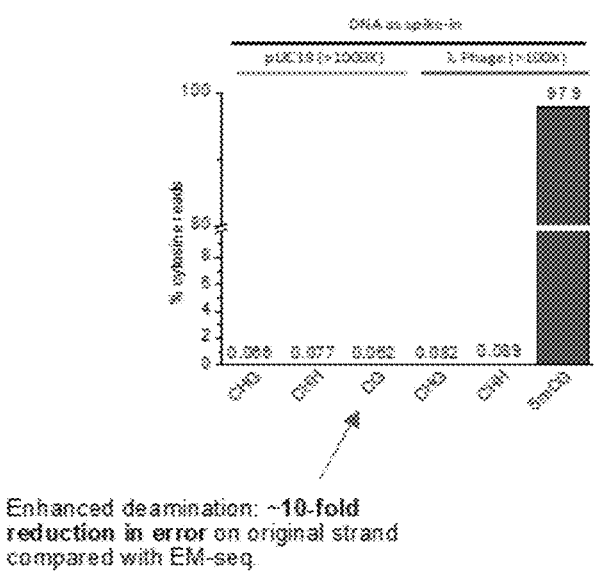
FIG. 40 shows suppression of false-positive methylation calls in two-base sequencing libraries deaminated using a combination of APOBEC3A and helicase, or fragments thereof.

During preparation of two-base sequencing libraries for 6-base discrimination (e.g., two-base sequencing that distinguishes 5-methyl cytosine from 5-hydroxymethyl cytosine, and e.g., wherein DNMT1 adds a methylation mark to a base in the cognate strand that is opposite to the methylated base in the original strand), a sequencing library that differs in the use of DNMT1 enzymatic processing operation was prepared using the two-base sequencing library preparation methods herein (e.g., wherein a hairpin is used to link the original forward strand and the cognate strand during library preparation). The libraries were prepared in the presence of DNMT1 before TET and βGT treatment. After mapping and deduplication, Cytosine and Thymine reads were resolved in the original forward strand of the sequencing libraries prepared for two-base sequencing. The MethylDackel software was used to determine deamination rates. Here, while deamination rates in CHH and CHG exceeds other non-helicase/APOBEC3A methods such as the result in FIG. 38, deamination at CpG drops (FIG. 40).

Figure 41A:
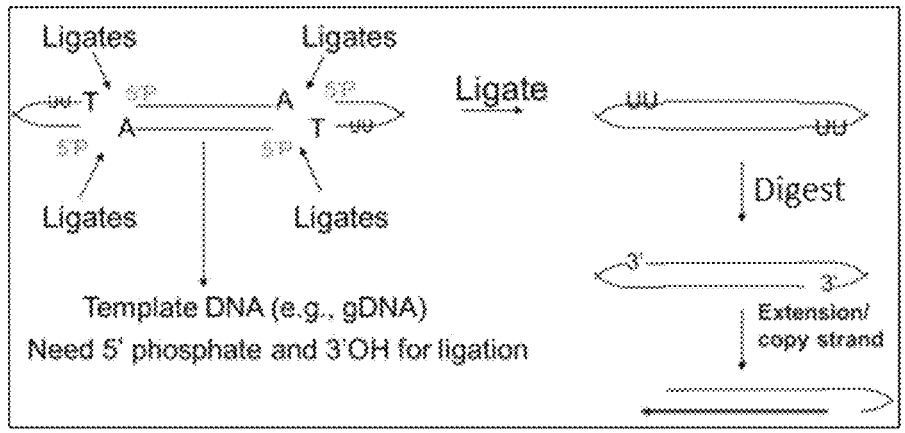
FIG. 41A depicts an example workflow involving the use of Uracil DNA glycosylase (UDG) and DNA glycosylase-lyase Endonuclease VIII to generate a nick on a hairpin adapter (that contains uridines).
Figure 41B:
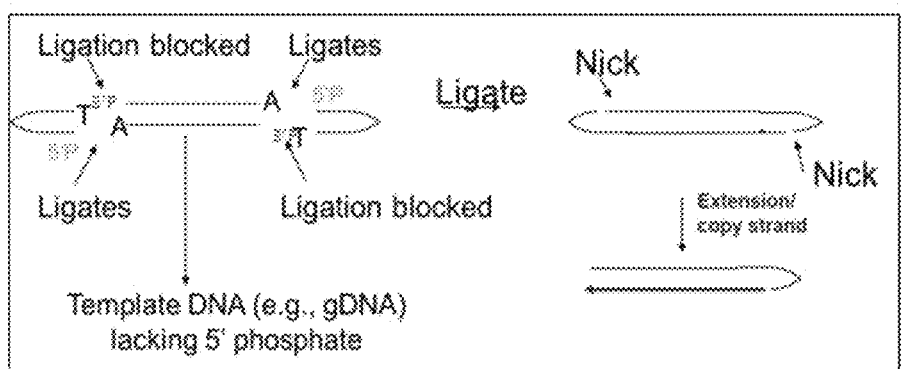
FIG. 41B depicts an example workflow that does not involve the use of Uracil DNA glycosylase (UDG) and DNA glycosylase-lyase Endonuclease VIII and the use of a hairpin adapter lacking uridines (but with 3' phosphate) and template DNA lacking 5' phosphate.

Example 16: Workflow for Generation of Libraries for Two-Base Sequencing without the Utilization of Uracil DNA Glycosylase (UDG) and DNA Glycosylase-Lyase Endonuclease VIII In this workflow, genomic DNA (gDNA) samples were prepared for library preparation in the following manner. First, gDNA (containing 0.5% pUC19 and methylated lambda gDNA) was fragmented to 250 bp by sonication in a microtube-50 using a Covaris M220 in low-TE buffer (10 mM Tris-HCl, 0.1 mM EDTA). The gDNA was quantified by dsDNA Qubit and the size distribution was checked using the Bioanalyzer or Tapestation. Synthetic controls (80 bp and 166 bp) were spiked in at 0.5% of amount of input DNA. For conditions a+b (FIGS. 42A-B), the gDNA was end repaired and A-tailed so that the 5'ends of the DNA were 5'phosphorylated and available for ligation. For conditions c+d (FIGS. 42A-B), gDNA samples were modified to lack the 5' phosphate and so were unable to be ligated at their 5'end. This was done by two different methods; c) T4 Polynucleotide Kinase (T4 PNK) was used to catalyze the exchange of phosphate groups between 5'-phosphate of the fragmented gDNA and ADP (exchange reaction), generating a gDNA sample lacking the 5' phosphate or d) rSAP phosphatase was used to actively remove any phosphates from the ends of the DNA. Conditions c+d (FIGS. 42A-B) were then end repaired and A-tailed using T4 DNA polymerase and Taq respectively. All samples then proceeded to hairpin adapter ligation. The hairpin adaptor ligation reactions were assembled in the same tube as the end-repair and A-tailing reactions. For conditions b–d (FIGS. 42A-B) the hairpin containing a 3'phosphate was used (FIG. 41B), in comparison condition a (FIGS. 42A-B) ligated a 3'OH hairpin containing uracils for cleavage (FIG. 41A). The ligation of the 3' end of the hairpin to the 5' ends of the fragmented gDNA sample was blocked by the hairpin's 3'phosphate (conditions b–d, FIGS. 42A-B) and for conditions c–d (FIGS. 42A-B) also by the 5'OH on the genomic DNA (FIG. 41B). Since ligation to the 3'end of the hairpin was blocked for conditions b–d (FIGS. 42A-B), Uracil DNA glycosylase (UDG) and DNA glycosylase-lyase Endonuclease VIII was not used to generate a nick in the hairpin adapter and the subsequent clean-up of this reaction was also not performed. Elimination of Uracil DNA glycosylase (UDG) and DNA glycosylase-lyase Endonuclease VIII and the associated clean-up operation can allow for a simpler workflow and also can result in overall faster library preparation (FIG. 41A and FIG. 41B).

The hairpin-ligated DNA mixture was cleaned up using magnetic beads and the DNA was heat denatured to separate the 2 genomic strands before proceeding to copy strand synthesis. During the copy strand synthesis operation, the 3' phosphate block on the hairpin adapters was removed and the 5' ends of the gDNA were 5'phosphorylated by the action of PNK enzyme in the reaction buffer. Furthermore, in this workflow, the copy strand is extended from the longer stem of the hairpin adapter, as there is no cutting back of the stem with the action of Uracil DNA glycosylase (UDG) and DNA glycosylase-lyase Endonuclease VIII (FIG. 41B).

Following copy strand synthesis, the DNA mixture was cleaned up using magnetic beads, Illumina adapters were ligated for sequencing and the DNA sample was then purified using magnetic beads.

Next, the adapter-ligated DNA was then treated with TET enzyme. The resulting DNA sample was combined with diluted Fe (II) solution along with oxidation enzymes and incubated at 37° C. for 1 hour in a thermocycler before adding the Stop reagent. The TET converted DNA was cleaned up using magnetic beads before proceeding to the deamination operation. In the deamination reaction, the DNA mixture was incubated in a reaction mixture containing APOBEC and UvrD helicase. The deaminated DNA was cleaned up using magnetic beads. PCR amplification was performed on the deaminated DNA for library preparation and the library DNA was purified using magnetic beads.

Figure 45A:
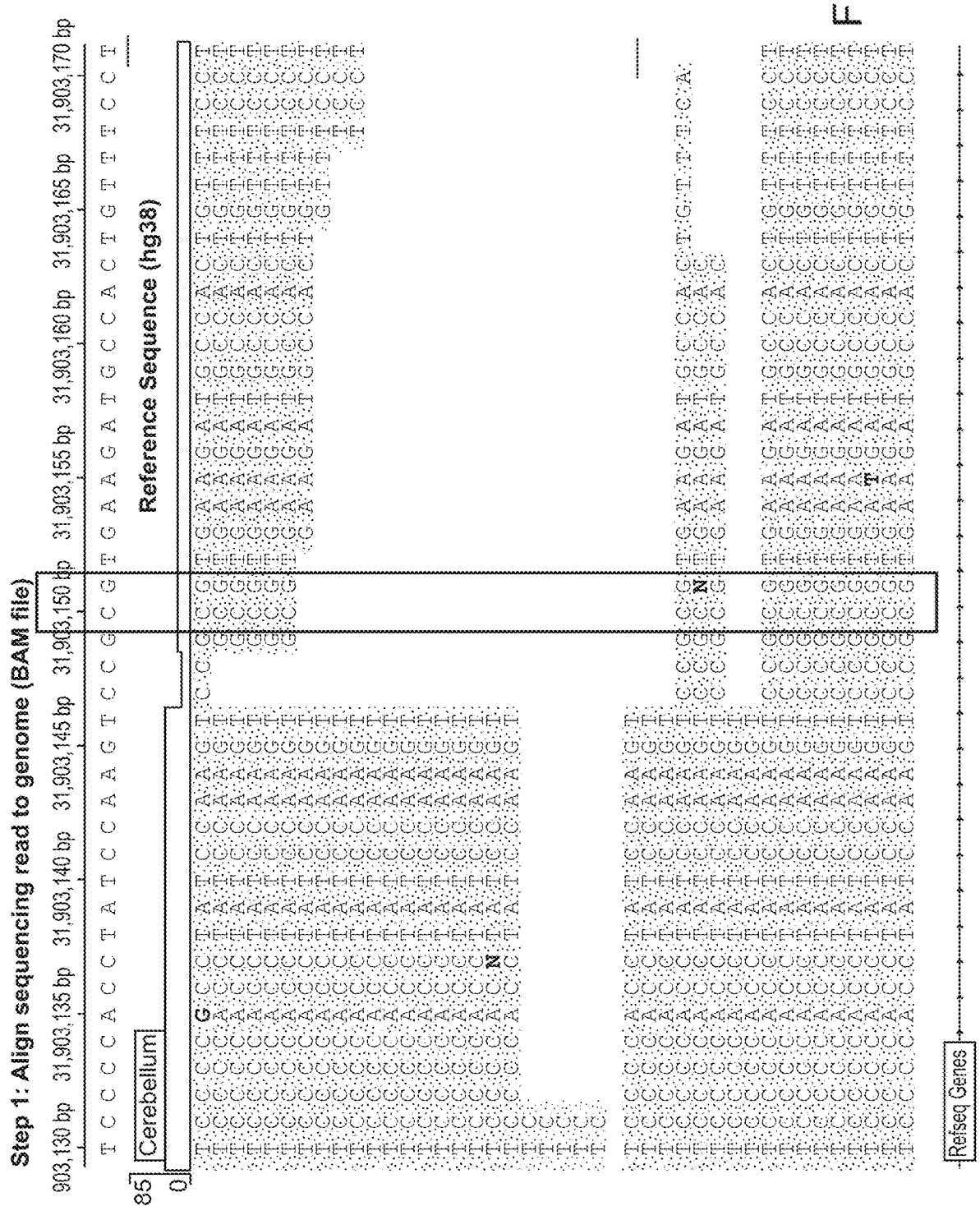
FIGS. 45A-C depicts an overview of the operations involved in the identification and quantification of methylation information at a strand level in a sample genome.
Figures 45B, 45C:
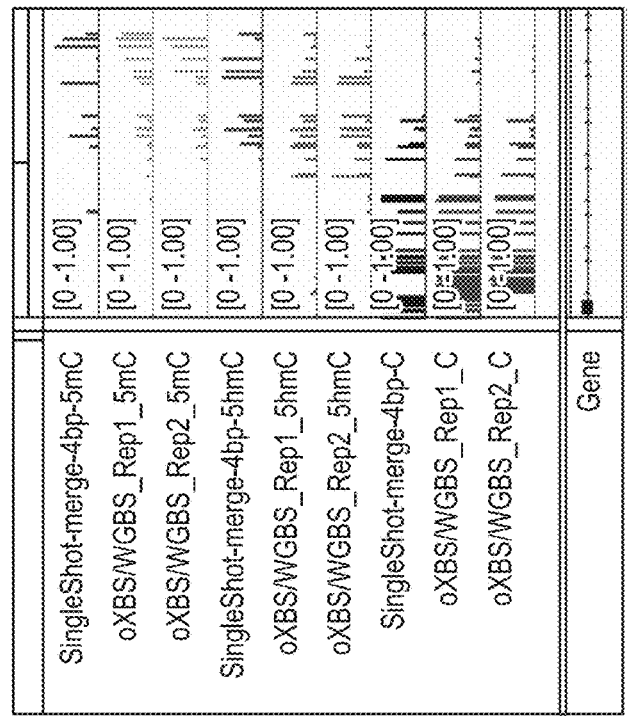

Example 17: Quantification and Base Calling of Methylation on the Forward and Reverse Strand in the Genome FIG. 45A-C presents an overview of the operations for 6-base calling (A, T, G, C, plus methylation and hydroxymethylation) via 4-base alignment. In the first operation, (A) alignment of genome sequencing reads to the reference genome is conducted, followed by (B) decoding of epigenetic code information at CpG site positions (an example CpG site indicated by the yellow box here) and (C) quantification of the epigenetic reads evaluated in the operation described herein (e.g., methylation or hydroxymethylation).

Figure 46A:
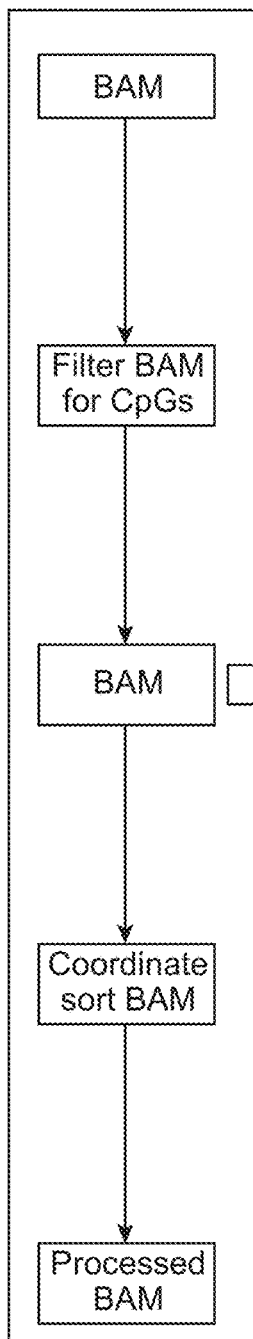
FIGS. 46A-C provides further workflows involved in the identification and quantification of methylation information at a strand level in a sample genome.
Figure 46B:
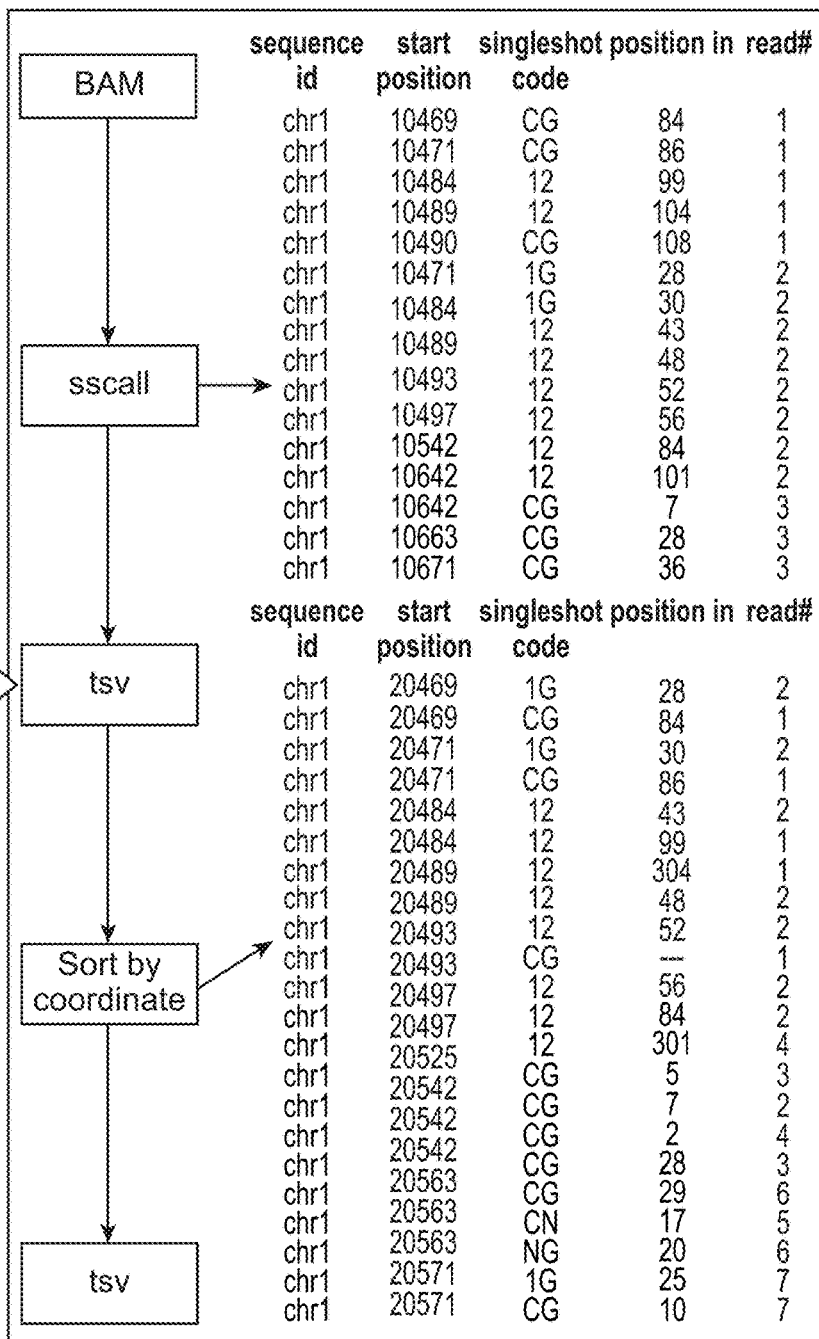
Figure 46C:

FIGS. 46A-C present more details on the operations involved in stranded calling of methylation information in a sample genome. In the first operation, sequencing reads from the sample genome were aligned to the reference genome (HG38). The orientation of the alignment of the reads to the reference genome was used to ascertain the strand (forward or reverse) of the sample genome that the reads are obtained from. For example, the reference genome was aligned in the forward orientation and if the read aligned with the same orientation as the reference genome, it is classified as a forward strand, whereas if the read aligned in the reverse complementary orientation, then the read was classified as being obtained from the reverse strand of the genome. A BAM file was created containing the positions of alignment to the reference genome (but does not store the reference genome sequence). The BAM alignment file was filtered for CpG sites and non-CpG sites (FIG. 46A). In order to find the location of the "CpG" sites, the start and end coordinates of the read were used to query an "interval tree", a data structure that will give back the positions of the CpGs in that sequence. The filtered BAM file was then sorted by genome coordinates resulting in a processed BAM file (FIG. 46A).

Figure 47:
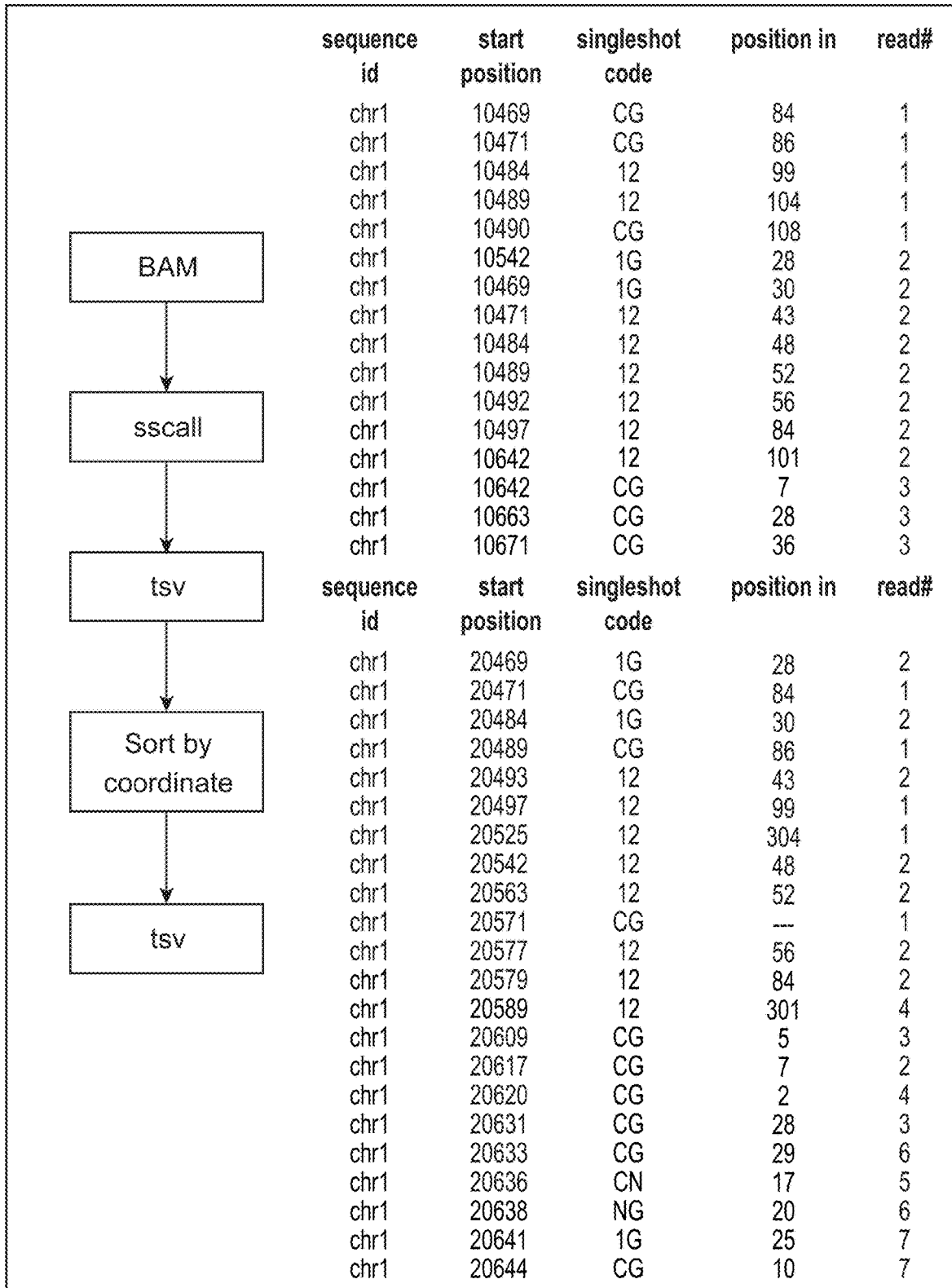
FIG. 47 depicts the representation of epigenetic code and strand information in the intermediate representation file.

The CpG sites identified in the operations described herein were analyzed further to identify epigenetic codes at a base level in the sample genome (FIG. 46B). The bioinformatics workflow in this operation extracts out epigenetic (methylation or hydroxymethylation) information corresponding to the bases in the sequencing read into an intermediate representation file which was then processed to quantify epigenetic information at the corresponding base positions. For example, in FIGS. 45A-B, the box around position 31,903,150 bp marks an example position of a CpG site for further analysis of methylation information. The processed BAM file was processed by the ssCALL program to extract the epigenetic code for every CpG site in every read. The resulting tsv file was sorted by genome coordinates again to generate an intermediate representation tsv file (FIG. 46B). The rows in the epigenetic code in the Intermediate Representation file contained information pertaining to sequence ID, a start position, epigenetic code corresponding to the position, and the read identifier. The Intermediate Representation file also contained information pertaining to the strand information ascertained from the orientation of the alignment of the sample sequence reads to the reference genome. Forward strand is designated by a (+) and reverse strand by (−). (FIG. 47).

The resulting epigenetic code file in the intermediate representation file was transformed into a quantification file containing counts of epigenetic states at the base positions in the genome. thereby allowing measurement of the frequency of the epigenetic states across the genome (FIG. 46C). The proportion of counts that are decoded as containing unmethylated, methylated, or hydroxymethylated states were used to generate a linear frequency map of these epigenetic states at the positions or chromosomal segments in the genome of interest (FIG. 46C).

Figure 48:
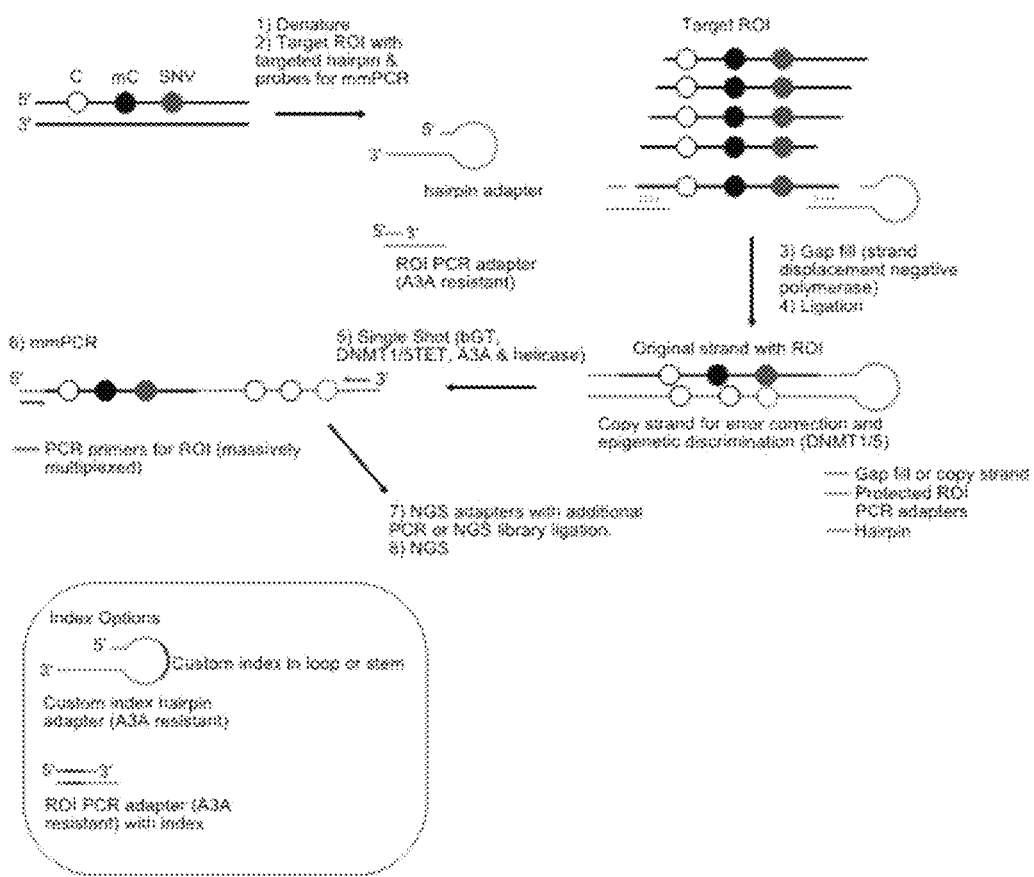
FIG. 48 depicts the representation of an example workflow for the measurement of epigenetic information in a targeted region of interest in the genome.

Example 18: Measurement of Epigenetic Information in One or More Targeted Genomic Regions of Interest In an embodiment, the methods and compositions described herein can be used to measure epigenetic information in a targeted region of interest in the genome (FIG. 48). For example, in such an embodiment, the starting DNA material (double stranded DNA) is first denatured (e.g. using temperature denaturation). In order to target a region of interest (ROI), a 4 base oligo is designed to target the 3' end of the ROI. The 4b oligo is attached to an Illumina custom index that can index individually captured strands. A second pair of targeting oligos are designed to target the 5' end of the ROT, thereby creating PCR handles for use in a later operation where the construct is deaminated. The oligo is a staggered duplex, is designed to contain an index, and has a targeting sequence that primes the 5' end of the ROI. Having primed the ROI at the 5' and 3' ends of ssDNA, the "gaps" are filled using a strand-displacement negative polymerase (such as T4 for example), followed by ligation (T4 ligase for example), thereby creating a copy strand whilst not displacing the hairpin or PCR handles, which is used as the template for the two-base sequence in the following operations. The epigenetic base mC is copied over from the original strand to the copied strand, and the 5hmC is protected from deamination by treatment with bGT enzyme. The construct is treated with TET (in the presence or absence of bGT) to make mC convert to fC, caC or ghmC (bases that are resistant to deamination). The hairpin is opened up using a combination of APOBEC3A and the helicase UvrD. The PCR handles are used to amplify the ROI. When targeting multiple regions, the method can be combined with a massively multiplex PCR. In one example, the method is adapted to include an additional PCR operation in which Illumina sequencing adapters are added to the PCR handles. In a different example, the original PCR operation is modified to contain extended primers that contain the PCR handle and also the Illumina adapters.

In a second embodiment, the methods and compositions described herein can be used to measure epigenetic information in a targeted region of interest in the genome. In this embodiment (FIG. 49), the starting DNA material is first denatured (e.g. using temperature denaturation). In order to target a region of interest (ROI), a 4 base oligo primer is designed that contains an additional sequence, e.g., an index, to be used in a PCR operation. The annealed 4 base primer is protected from deamination, for example, through the use of an APOBEC3A resistant base (e.g. hmC, fC or caC). The annealed 4 base primer is extended with a polymerase (e.g., Klenow polymerase). A hairpin is added by first A-tailing, and then using a hairpin with a T-overhang and ligating the hairpin to the construct, in order to generate the construct for two-base sequencing. The epigenetic base mC is copied over from the original strand to the copied strand, and the 5hmC is protected from deamination by treatment with bGT enzyme. The construct is treated with TET (in the presence or absence of bGT) to oxidise mC to fC, caC or ghmC. (bases that are resistant to deamination). The hairpin is opened up using a combination of APOBEC3A and the helicase UvrD. The APOBEC3A PCR handle is used to amplify the ROI in combination with a 3 base (A, T, and G) targeting oligo (the 3 base targeting oligo is used to target the ROI as the ROT, outside of a CpG region, may be deaminated at this stage of the workflow). When targeting multiple regions, the method can be combined with a massively multiplex PCR. In one example, the method is adapted to include an additional PCR operation in which Illumina sequencing adapters are added to the PCR handles. In a different example, the original PCR operation is modified to contain extended primers that contain the PCR handle and the Illumina adapters.

In a third embodiment, the methods and compositions described herein can be used to measure epigenetic information in a targeted region of interest in the genome. In this embodiment (FIG. 50), the starting DNA material (double stranded DNA) is first end-repaired and A-tailed. This material is adapted with hairpin using "TA" ligation whereby the hairpin contains a T-overhang that primes and is used to ligate hairpin on either side of the DNA. The hairpin contains a U that can be cut using a digestion enzyme (e.g., the enzymes Uracil DNA Glycosylase (UDG) and Endonuclease VIII may be used). A probe (4 base oligo) is used to prime to the 3' end of the said DNA construct such that it now flanks the hairpin on the opposite side of the ROI. The oligo is protected from APOBEC3A deamination, for example by containing a APOBEC3A resistant base (e.g. hmC, fC or caC). The 5' end of the oligo is made exonuclease resistant by containing modified bases (e.g. phosphorothioates derivatives). In one embodiment, the oligo may contain an index. The priming oligo is extended with a strand displacement negative polymerase that does not displace the hairpin. The copy strand is then ligated to the hairpin. The potential mismatch at the 3' end is trimmed with a ssDNA specific exonuclease, and the complementary sequence is built with a polymerase using APOBEC3A resistant bases such as fC or caC to generate the construct for two-base sequencing. The epigenetic base mC can now be copied over form the original strand to the copied strand, and the 5hmC can be protected from deamination by treatment with bGT enzyme. The construct is treated with TET (in the presence or absence of bGT) to oxidise mC to generate fC, caC, or ghmC which are resistant to deamination. The hairpin is opened up using a combination of APOBEC3A and the helicase UvrD. The ROI can now be amplified using the deamination resistant PCR handles. When targeting multiple regions, the method can be combined with a massively multiplex PCR, where multiple primers are used. In one example, the method is adapted to include an additional PCR operation in which Illumina sequencing adapters are added to the PCR handles. In a different example, the original PCR operation is modified to contain extended primers that contain the PCR handle and the Illumina adapters.

While preferred embodiments of the present inventive compositions and methods have been shown and described herein, it will be obvious to those skilled in the art that such embodiments are provided by way of example only. It is not intended that the inventive compositions and methods be limited by the specific examples provided within the specification. While the inventive compositions and methods have been described with reference to the aforementioned specification, the descriptions and illustrations of the embodiments herein are not meant to be construed in a limiting sense. Numerous variations, changes, and substitutions will now occur to those skilled in the art without departing from the inventive compositions and methods. Furthermore, it shall be understood that all aspects of the inventive compositions and methods are not limited to the specific depictions, configurations or relative proportions set forth herein which depend upon a variety of conditions and variables. It should be understood that various alternatives to the embodiments of the inventive compositions and methods described herein may be employed in practicing the inventive compositions and methods. It is therefore contemplated that the inventive compositions and methods shall also cover any such alternatives, modifications, variations or equivalents. It is intended that the following claims define the scope of the inventive compositions and methods and that methods and structures within the scope of these claims and their equivalents be covered thereby.

What is claimed is:
1. A method, comprising:
(a) generating a double-stranded polynucleotide comprising: (i) a first base that is a substrate for a deaminase that is unprotected, and (ii) a second base that is a substrate for a deaminase that is protected,
(b) contacting the double-stranded polynucleotide with a helicase and said deaminase to yield a nucleic acid molecule comprising a nucleic acid sequence comprising a deaminated base and said second base, wherein a base of said double-stranded polynucleotide is deaminated to yield said deaminated base, wherein said deaminated base is different from said second base;
(c) sequencing nucleotides of said nucleic acid sequence or a complement thereof to obtain sequencing data; and
(d) processing said sequencing data to identify and distinguish said first base and said second base.
2. The method of claim 1, wherein said nucleic acid molecule comprises sequences of both strands of said double-stranded polynucleotide, and said sequencing comprises sequencing said sequences of both strands.

3. The method of claim 1, wherein strands of said double-stranded polynucleotide are linked covalently via a hairpin.

4. The method of claim 1, further comprising, prior to (a), providing a polynucleotide and generating said double-stranded polynucleotide from said polynucleotide.

5. The method of claim 4, further comprising, prior to (a), conducting one or more chemical reactions or one or more enzymatic reactions on said polynucleotide to generate said double-stranded polynucleotide.

6. The method of claim 5, further comprising conducting a nucleic acid extension reaction using said polynucleotide.

7. The method of claim 5, further comprising contacting said polynucleotide with an entity having DNA methyltransferase activity.

8. The method of claim 7, wherein said entity having DNA methyltransferase activity is selected from DNA (cytosine-5)-methyltransferase 1 (DNMT1) or DNA (cytosine-5)-methyltransferase 5 (DNMT5).

9. The method of claim 5, further comprising contacting said polynucleotide with an oxidizing agent.

10. The method of claim 9, wherein said oxidizing agent is a methylcytosine dioxygenase.

11. The method of claim 10, wherein said methylcytosine dioxygenase is a ten-eleven translocation (TET) enzyme.

12. The method of claim 5, further contacting said polynucleotide with an glycosylation agent.

13. The method of claim 5, wherein said polynucleotide comprises a methylated base.

14. The method of claim 13, further comprising conducting an oxidation reaction and a glycosylation reaction to generate said double-stranded polynucleotide.

15. The method of claim 14, wherein (c) comprises processing said sequencing data to identify said methylated base as methylated.

16. The method of claim 15, wherein (c) comprises processing said sequencing data to identify said methylated base as methylated with an accuracy of at least about 95%.

17. The method of claim 5, wherein said polynucleotide comprises a methyl cytosine base or a hydroxymethyl cytosine base.

18. The method of claim 17, further comprising conducting a methyltransferase reaction, an oxidation reaction and a glycosylation reaction to generate said double-stranded polynucleotide.

19. The method of claim 18, wherein (c) comprises processing said sequencing data to identify said methyl cytosine base as methyl cytosine or said hydroxymethyl cytosine base as hydroxymethyl cytosine.

20. The method of claim 18, wherein (c) comprises processing said sequencing data to identify said methyl cytosine base as methyl cytosine or said hydroxymethyl cytosine base as hydroxymethyl cytosine with an accuracy of at least about 95%.

21. The method of claim 1, wherein said base is a cytosine base, a methyl cytosine base or a hydroxymethyl cytosine base, and wherein (c) comprises identifying said cytosine base, said methyl cytosine, or said hydroxymethyl cytosine as comprising cytosine.

22. The method of claim 21, wherein (c) comprises processing said sequencing data to identify said cytosine base, said methyl cytosine, or said hydroxymethyl cytosine as comprising cytosine with an accuracy of at least about 95%.

23. The method of claim 1, wherein said deaminase is an apolipoprotein B mRNA editing catalytic polypeptide-like (APOBEC) enzyme or fragment thereof.

24. The method of claim 1, wherein said helicase comprises an amino acid sequence that is at least 90% homologous to UvrD helicase, *Geobacillus sterothermophilus* Bad protein, a PcrA helicase or fragment thereof.

25. The method of claim 24, wherein said helicase is a UvrD helicase, *Geobacillus sterothermophilus* Bad protein, a PcrA helicase or fragment thereof.

26. The method of claim 1, further comprising using the sequencing data to diagnose a condition in a subject.

27. The method of claim 26, wherein the condition is a cancer or a neurodegenerative condition.

* * * * *